(12) United States Patent
Robins et al.

(10) Patent No.: US 10,221,461 B2
(45) Date of Patent: Mar. 5, 2019

(54) IMMUNOCOMPETENCE ASSESSMENT BY ADAPTIVE IMMUNE RECEPTOR DIVERSITY AND CLONALITY CHARACTERIZATION

(71) Applicants: Adaptive Biotechnologies Corp., Seattle, WA (US); Memorial Sloan-Kettering Cancer Center, New York, NY (US)

(72) Inventors: Harlan S. Robins, Seattle, WA (US); Julie Rubinstein, Seattle, WA (US); Ryan Emerson, Seattle, WA (US); Jianda Yuan, New York, NY (US)

(73) Assignees: ADAPTIVE BIOTECHNOLOGIES CORP., Seattle, WA (US); MEMORIAL SLOAN-KETTERING CANCER CENTER, New York, NY (US)

( * ) Notice: Subject to any disclaimer, the term of this patent is extended or adjusted under 35 U.S.C. 154(b) by 11 days.

(21) Appl. No.: 15/637,871

(22) Filed: Jun. 29, 2017

(65) Prior Publication Data
US 2018/0030543 A1   Feb. 1, 2018

Related U.S. Application Data

(63) Continuation of application No. 14/432,738, filed as application No. PCT/US2013/062925 on Oct. 1, 2013.

(60) Provisional application No. 61/708,534, filed on Oct. 1, 2012.

(51) Int. Cl.
| | |
|---|---|
| *C12Q 1/6886* | (2018.01) |
| *C12Q 1/6851* | (2018.01) |
| *C12Q 1/6883* | (2018.01) |
| *G06F 19/22* | (2011.01) |
| *G06F 19/12* | (2011.01) |

(52) U.S. Cl.
CPC ......... *C12Q 1/6886* (2013.01); *C12Q 1/6851* (2013.01); *C12Q 1/6883* (2013.01); *G06F 19/22* (2013.01); *C12Q 2600/106* (2013.01); *C12Q 2600/156* (2013.01); *C12Q 2600/16* (2013.01); *G06F 19/12* (2013.01)

(58) Field of Classification Search
None
See application file for complete search history.

(56) References Cited

U.S. PATENT DOCUMENTS

| | | |
|---|---|---|
| 3,270,960 A | 9/1966 | Phillips |
| 3,773,919 A | 11/1973 | Boswell et al. |
| 4,474,754 A | 10/1984 | Shimizu et al. |
| 4,683,195 A | 7/1987 | Mullis et al. |
| 4,683,202 A | 7/1987 | Mullis |
| 4,751,188 A | 6/1988 | Valet |
| 4,800,159 A | 1/1989 | Mullis et al. |
| 4,876,189 A | 10/1989 | Schetters |
| 4,942,124 A | 7/1990 | Church |
| 4,965,188 A | 10/1990 | Mullis et al. |
| 5,075,217 A | 12/1991 | Weber |
| 5,126,022 A | 6/1992 | Soane et al. |
| 5,149,625 A | 9/1992 | Church et al. |
| 5,168,038 A | 12/1992 | Tecott et al. |
| 5,189,147 A | 2/1993 | Saito et al. |
| 5,210,015 A | 5/1993 | Gelfand et al. |
| 5,213,960 A | 5/1993 | Chang |
| 5,231,012 A | 7/1993 | Mosmann et al. |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,364,759 A | 11/1994 | Caskey et al. |
| 5,399,491 A | 3/1995 | Kacian et al. |
| 5,418,134 A | 5/1995 | Morley |
| 5,449,752 A | 9/1995 | Fujii et al. |
| 5,498,392 A | 3/1996 | Wilding et al. |
| 5,506,126 A | 4/1996 | Seed et al. |
| 5,587,128 A | 12/1996 | Wilding et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,698,396 A | 12/1997 | Pfreundschuh |
| 5,699,798 A | 12/1997 | Hochman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,854,033 A | 12/1998 | Lizardi |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

US 8,642,750, 02/2014, Faham et al. (withdrawn)

(Continued)

*Primary Examiner* — Laura B Goddard
(74) *Attorney, Agent, or Firm* — Cooley LLP

(57) ABSTRACT

Disclosed are methods for determining the immunological status of the adaptive immune system of a subject by identifying and quantifying rearranged DNA (and/or subsequently transcribed RNA) sequences encoding T cell receptor (TCR) and/or immunoglobulin (IG) polypeptides, in a lymphoid DNA-containing sample from the subject TCR and/or IG sequence diversity and sequence distribution permit immunocompetence and immune repertoire assessment and reflect the degree of T cell or B cell clonality and clerical expansion in the sample. Methods for stratifying patient populations on the basis of immunocompetence including likelihood of responding to immunotherapy are also described.

16 Claims, 14 Drawing Sheets

(56) References Cited

U.S. PATENT DOCUMENTS

| | | |
|---|---|---|
| 5,858,195 A | 1/1999 | Ramsey |
| 5,925,517 A | 7/1999 | Tyagi et al. |
| 5,935,793 A | 8/1999 | Wong |
| 5,969,108 A | 10/1999 | McCafferty et al. |
| 5,981,176 A | 11/1999 | Wallace |
| 5,981,179 A | 11/1999 | Lorinez et al. |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,087,096 A | 7/2000 | Dau et al. |
| 6,090,592 A | 7/2000 | Adams et al. |
| 6,091,000 A | 7/2000 | Haynes |
| 6,143,496 A | 11/2000 | Brown et al. |
| 6,172,214 B1 | 1/2001 | Brenner |
| 6,174,670 B1 | 1/2001 | Wittwer et al. |
| 6,258,540 B1 | 7/2001 | Lo et al. |
| 6,258,568 B1 | 7/2001 | Nyren |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,605,272 B2 | 8/2003 | Novak et al. |
| 6,613,525 B2 | 9/2003 | Nelson et al. |
| 6,667,159 B1 | 12/2003 | Walt |
| 6,753,147 B2 | 6/2004 | Vogelstein et al. |
| 6,787,308 B2 | 9/2004 | Balasubramanian et al. |
| 6,794,499 B2 | 9/2004 | Wengel et al. |
| 6,806,079 B1 | 10/2004 | McCafferty et al. |
| 6,858,412 B2 | 2/2005 | Willis et al. |
| 6,919,434 B1 | 7/2005 | Goto et al. |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,181,590 B2 | 11/2015 | Robins et al. |
| 9,217,176 B2 | 12/2015 | Faham et al. |
| 9,228,232 B2 | 1/2016 | Faham et al. |
| 9,416,420 B2 | 8/2016 | Faham et al. |
| 9,512,487 B2 | 12/2016 | Faham et al. |
| 9,809,813 B2 | 11/2017 | Robins et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0033490 A1 | 2/2004 | Laird et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0214779 A1 | 10/2004 | Ma et al. |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |

(56) References Cited

U.S. PATENT DOCUMENTS

| | | |
|---|---|---|
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0285984 A1 * | 11/2010 | Wettstein ............ C12Q 1/6883 506/9 |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0183863 A1 | 7/2011 | Wagner et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2013/0005584 A1 | 1/2013 | Faham |
| 2013/0017957 A1 | 1/2013 | Faham et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0094376 A1 | 4/2014 | Han |
| 2014/0127699 A1 | 5/2014 | Han |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0167080 A1 | 6/2015 | Moorhead et al. |
| 2015/0203897 A1 | 7/2015 | Robins et al. |
| 2015/0218656 A1 | 8/2015 | Kirsch et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0299785 A1 | 10/2015 | Livingston et al. |
| 2016/0002731 A1 | 1/2016 | Robins et al. |
| 2016/0115532 A1 | 4/2016 | Faham |
| 2016/0201133 A1 | 7/2016 | Faham et al. |
| 2016/0251721 A1 | 9/2016 | Robins et al. |
| 2016/0251728 A1 | 9/2016 | Faham et al. |
| 2016/0258025 A1 | 9/2016 | Klinger et al. |
| 2016/0340729 A1 | 11/2016 | Emerson et al. |
| 2017/0335386 A1 | 11/2017 | Livingston et al. |
| 2017/0349954 A1 | 12/2017 | Faham et al. |
| 2017/0362653 A1 | 12/2017 | Robins et al. |
| 2018/0073015 A1 | 3/2018 | Robins et al. |
| 2018/0080090 A1 | 3/2018 | Faham et al. |
| 2018/0087109 A1 | 3/2018 | Klinger et al. |
| 2018/0112278 A1 | 4/2018 | Faham et al. |

FOREIGN PATENT DOCUMENTS

| | | |
|---|---|---|
| CN | 103097888 A | 5/2013 |
| EP | 0303459 A2 | 2/1989 |
| EP | 0799897 A1 | 10/1997 |
| EP | 1544308 A1 | 6/2005 |

(56) References Cited

FOREIGN PATENT DOCUMENTS

| | | |
|---|---|---|
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2012-508011 A | 4/2012 |
| JP | 2013-524848 A | 6/2013 |
| JP | 2013-524849 A | 6/2013 |
| WO | WO 1993/001838 A1 | 2/1993 |
| WO | WO 1995/028481 A1 | 10/1995 |
| WO | WO 1997/013877 A1 | 4/1997 |
| WO | WO 1997/018330 A1 | 5/1997 |
| WO | WO 1997/046706 A1 | 12/1997 |
| WO | WO 1998/001738 A2 | 1/1998 |
| WO | WO 1998/044151 A1 | 10/1998 |
| WO | WO 1999/019717 A1 | 4/1999 |
| WO | WO 1999/020798 A1 | 4/1999 |
| WO | WO 2002/024322 A2 | 3/2002 |
| WO | WO 2003/044225 A2 | 5/2003 |
| WO | WO 2003/052101 A1 | 6/2003 |
| WO | WO 2003/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 6/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/151416 A1 | 12/2010 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/142213 A2 | 10/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/055561 A1 | 4/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2016/086029 A1 | 6/2016 |

OTHER PUBLICATIONS

Sensi et al (J Experimental Medicine, 1993, 178:1231-1246).*
Fang et al (Journal of Investigative Dermatology, 2008, 128:2596-2605).*
Curran et al (PNAS, 2010, 107:4275-4280).*
Hamid et al (J Translational medicine, 2011, 9:204, internet pp. 1-16).*
Tarhini et al (J Clinical Oncology, 2012, 30 (suppl; abstract 8533), presented Jun. 2, 2012).*
Abath et al. "Single-tubed nested PCR using immobilized internal primers", *Biotechniques*, 33(6): 1210-1212, 1214 (2002).
Abbott, et al. "Design and use of signature primers to detect carry-over of amplified material", *J Virol Methods*, 46(1):51-59, Abstract Only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).
Akatsuka, Y. et al., "Rapid screening of T-cell receptor (TCR) variable gene usage by multiplex PCR: Application for assessment of clonal composition", *Tissue Antigens*, 53(2):122-134 (1999).
Alatrakchi et al. "T-cell clonal expansion in patients with B-cell lymphoproliferative disorders", *Journal of Immunotherapy*, 21(5):363-370 (1998).
Alexandre, D. et al. "*H. sapiens* rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.

(56) References Cited

OTHER PUBLICATIONS

Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Al-Lazikani, B. et al., "Standard Conformations for the Canonical Structures of Immunoglobulins," *J. Mol. Biol.*, 273:927-948 (1997).
Altin et al. "The role of CD45 and CD45-associated molecules in T cell activation", *Immunology and Cell Biology*, 75: 430-445 (1997).
Altman, et al. "Phenotypic analysis of antigen-specific T lymphocytes", *The Journal of Immunology*, 187(1):7-9 (2011).
Altschul, et al. "Basic local alignment search tool", *J Mol Biol.*, 215(3):403-410 (1990).
Andreasson, et al. "The human IgE-encoding transcriptome to assess antibody repertoires and repertoire evolution", *J Mol Biol.*, 362(2):212-227 (2006). Epub Aug. 14, 2006.
Arnaout. "Specificity and overlap in gene segment-defined antibody repertoires", *BMC Genomics*, 6: 148 (2005).
Arden, et al. "Human T-cell receptor variable gene segment families", *Immunogenetics*, 42(6):455-500, Abstract Only (1995).
Armand, P. et al., "Detection of circulating tumour DNA in patients with aggressive B-cell non-Hodgkin lymphoma", *Brit. J. Haematol.*, vol. 163, pp. 123-126 (2013).
Arstila, T.P., et al., "A direct estimate of the human αβ T cell receptor diversity," *Science*, 286(5441): 958-961 (1999).
Aslanzadeh. "Preventing PCR amplification carryover contamination in a clinical laboratory", *Ann Clin Lab Sci.*, 34(4):389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).
Ateya, et al. "The good, the bad, and the tiny: a review of microflow cytometry", *Anal Bioanal Chem.*, 391(5): 1485-1498 (2008). doi: 10.1007/s00216-007-1827-5. Epub Jan. 29, 2008.
Babrzadeh et al. "Development on High-throughput Sequencing Technology: emPCR Titration and Barcode Design",*Stanford School of Medicine*, 2 pages (2011).
Bagnara, et al. "IgV gene intraclonal diversification and clonal evolution in B-cell chronic lymphocytic leukaemia", *British Journal of Haematology*, 133(1):50-58 (2006).
Bahloul, M. et al., "Clinical impact of molecular diagnostics in low-grade lymphoma," Best Practice & Research Clinical Haematology, 18(1):97-111 (2005).
Baldauf, "Phylogeny for the faint of heart: a tutorial," Trends in Genetics, 19(6): 345-351 (2003).
Barbas, et al. "Assembly of combinatorial antibody libraries on phage surfaces: the gene III site", *PNAS*, 88(18): 7978-7982, Abstract Only (1991).
Barker, et al. "A second type II restriction endonuclease from Thermus aquaticus with an unusual sequence specificity", *Nucleic Acids Res.*, 12(14): 5567-5581 (1984).
Batzoglou, S. "The many faces of sequence alignment", *Briefings in Bioinformatics*, 6:6-22 (2005).
Baum and McCune et al. "Direct measurement of T-cell receptor repertoire diversity with AmpliCot", *Nat Methods*, 3(11): 895-901 (2006).
Becker-André and Hahlbrock. "Absolute mRNA quantification using the polymerase chain reaction (PCR). A novel approach by a PCR aided transcript titration assay (PATTY)", *Nucleic Acids Res.*, 17(22): 9437-9446 (1989).
Becton-Dickinson, CD marker handbook. bdbiosciences.com/go/mousecdmarkers, p. 1-47 (2010).
Becton-Dickinson T-Cell Research Tools, "Novel multicolor flow cytometry tools for the study of CD4+T-cell differentiation and plasticity", 16 pages (2009).

Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", *Blood*, 83(8):2238-2247 (1994).
Ben-Ezra, et al. Effect of fixation on the amplification of nucleic acids from paraffin-embedded material by the polymerase chain reaction, *The Journal of Histochemistry and Cytochemistry*, 39(3): 351-354 (1991).
Béné and Kaeda, "How and why minimal residual disease studies are necessary in leukemia: a review from WP10 and WP12 of the European LeukaemiaNet", *Haematologica*, 94(8):1135-1150 (2009).
Benecke. "DNA typing in forensic medicine and in criminal investigations: a current survey", *Naturwissenschaften*, 84(5): 181-188 (1997).
Benichou, J. et al., "Rep-Seq: uncovering the immunological repertoire through next-generation sequencing", *Immunology*, 135(3): 183-191 (2011).
Benichou, J. et al., "The restricted DH gene reading frame usage in the expressed human antibody repertoire is selected based upon its amino acid content", J Immunol., 190(11): 5567-77, 29 pages (2013).
Bentley, et al. "Accurate whole human genome sequencing using reversible terminator chemistry", *Nature*, 456(7218) :53-59 (2008). doi: 10.1038/nature07517.
Bereczki, et al. "Optimization of PCR amplification for B- and T-cell clonality analysis on formalin-fixed and paraffin-embedded samples", *Pathology Oncology Research*, 13(3): 209-214 (2007). Epub Oct. 7, 2007.
Berger, et al. "The clonotypic T cell receptor is a source of tumor-associated antigens in cutaneous T cell lymphoma", *Annals of the New York Academy of Sciences*, 941:106-122, Abstract Only (2001).
Berget, et al. "Detection of clonality in follicular lymphoma using formalin-fixed, paraffin-embedded tissue samples and Biomed-2 immunoglobulin primers", J Clin Pathol., 64(1):37-41 (2011). doi: 10.1136/jcp.2010/081109. Epub Oct. 28, 2010.
Bernard et al. "Color multiplexing hybridization probes using the apolipoprotein E locus as a model system for genotyping", Anal Biochem., 273(2):221-228 (1999).
Bernardin, F. et al., "Estimate of the total Number of CD8+ clonal expansions in healthy adults using a new DNA heteroduplex-tracking assay for CDR3 repertoire analysis", *Journal of Immunological Methods*, 274(1-2):159-175 (2003).
Berquam-Vrieze, K. et al., "Cell of origin strongly influences genetic selection in a mouse model of T-ALL", *Blood*, 118:4646-4656 (2011).
Bertness, et al. "T-Cell Receptor Gene Rearrangements as Clinical Markers of Human T-Cell Lymphomas", *The New England Journal of Medicine*, 313:534-538 (1985).
Berzofsky, et al. "Progress on new vaccine strategies for the immunotherapy and prevention of cancer", *J Clin Invest.*, 113(11): 1515-1525 (2004).
Biagi, et al. "Responses to human CD40 ligand/human interleukin-2 autologous cell vaccine in patients with B-cell chronic lymphocytic leukemia", *Clin Cancer Res.*, 11(19 Pt 1): 6916-6923 (2005).
Biggerstaff, et al. "Enumeration of leukocyte infiltration in solid tumors by confocal laser scanning microscopy", *BMC Immunol.*, 7:16, 13 pages (2006).
Blow, N., "PCR's next frontier," *Nature Methods*, 4(10):869-875 (2007).
Brochet et al. "IMGT/V-QUEST: the highly customized and integrated system for IG and TR standardized V-J and V-D-J sequence analysis", *Nucleic Acids Research*, vol. 36, Web Server issue W503-W508 (2008).
Bolotin, D.A. et al., "Next generation sequencing for TCR repertoire profiling: Platform-specific features and correction algorithms", *Eur. J. Immunol.*, 42:3073-3083 (2012).
Bonarius, H.P.J. et al. "Monitoring the T-Cell Receptor Repertoire at Single-Clone Resolution", *PLOS One*, 1(e55):1-10 (2006).
Bonner et al. "Fluorescence activated cell sorting", Rev Sci Instrum., 43(3):404-409, Abstract Only (1972).

(56) References Cited

OTHER PUBLICATIONS

Boria, et al. "Primer sets for cloning the human repertoire of T cell receptor variable regions", *BMC Immunology*, 9:50, 9 pages (2008).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", *Molecular Immunology*, 45: 2437-2445 (2008).
Bousso. "Generation of MHC-peptide tetramers: a new opportunity for dissecting T-cell immune responses", Microbes Infect., 2(4):425-429, Abstract Only (2000).
Boyce, et al. "Human regulatory T-cell isolation and measurement of function", *BD Biosciences*, pp. 1-20 (2010).
Boyd, S.D. et al., "Individual Variation in the Germline Ig Gene Repertoire Inferred from Variable Region Gene Rearrangements", *The Journal of Immunology*, 184(12): 6986-6992 (2010). Epub 2010.
Boyd, S.D. et al., "Measurement and Clinical Monitoring of Human Lymphocyte Clonality by Massively Parallel V-D-J Pyrosequencing," *Science Translational Medicine*, 1:12ra23, 40 pages, including Supplementary Materials (2009).
Bradfield, et al. "Graft-versus-leukemia effect in acute lymphoblastic leukemia: the importance of tumor burden and early detection", Leukemia, 18(6): 1156-1158 (2004).
Bravo and Irizarry. "Model-Based Quality Assessment and Base-Calling for Second-Generation Sequencing Data", Biometrics, 66(3): 665-674 (2010).
Brehm-Stecher and Johnson. "Single-cell microbiology: tools, technologies, and applications", *Microbiology and Molecular Biology Reviews*, 68(3):538-559 (2004).
Brenan, C. et al., "High throughput, nanoliter quantitative PCR," *Drug Discovery Today: Technologies*, 2(3):247-253 (2005).
Brenner, et al. "In vitro cloning of complex mixtures of DNA on microbeads: physical separation of differentially expressed cDNAs", *PNAS*, 97(4): 1665-1670 (2000).
Brentjens, et al. "CD19-targeted T cells rapidly induce molecular remissions in adults with chemotherapy-refractory acute lymphoblastic leukemia", Sci Transl Med., 5(177): 177ra38 (2013). doi: 10.1126/scitranslmed.3005930.
Brisco, et al. "Determining the repertoire of IGH gene rearrangements to develop molecular markers for minimal residual disease in B-lineage acute lymphoblastic leukemia", *J Mol Diagn.*, 11(3):194-200 (2009).
Brisco, et al. "Outcome prediction in childhood acute lymphoblastic leukaemia by molecular quantification of residual disease at the end of induction", Lancet, 343:196-200 (1994).
Brockman et al, "Quality scores and SNP detection in sequencing-by-synthesis systems," Genome Research, 18: 763-770 (2008).
Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.
Brody, et al., "Immunotransplant for mantle cell lymphoma: Phase I/II study preliminary results", *Journal of Clinical Oncology*, ASCO Annual Meeting Abstracts Part 1, Suppl; abstr 2509: vol. 29, No. 15, 1 page (2011).
Brody, et al. "Lymphoma immunotherapy: vaccines, adoptive cell transfer and immunotransplant", *Immunotherapy*, 1(5): 809-824 (2009). doi: 10.2217/imt.09.50.
Brown, et al. "Current techniques for single-cell lysis", *J. R. Soc. Interface*, 5:S131-S138 (2008).
Brownie et al. "The elimination of primer-dimer accumulation in PCR", Nucleic Acids Research, 25(16): 3235-3241 (1997).
Brüggemann, et al. "Clinical significance of minimal residual disease quantification in adult patients with standard-risk acute lymphoblastic leukemia", *Blood*, 107(3):1116-1123 (2006). Epub Sep. 29, 2005.

Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).
Brüggemann, et al. "Standardized MRD quantification in European ALL trials: proceedings of the Second International Symposium on MRD assessment in Kiel, Germany, Sep. 18-20, 2008", *Leukemia*, 24(3):521-535 (2010). doi: 10.1038/leu.2009.268. Epub Dec. 24, 2009.
Buck, G.A. et al. "Design Strategies and Performance of Custom DNA Sequencing Primers", *Biotechniques*, 27(3):528-536 (1999).
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Butkus, B. "Hutch Team Uses ddPCR to Quantify T-Cell Response in Tumors; Adaptive Biotech Eyes Market", *PCR insider*, Dec. 12, 2013, 3 pages http://www.genomeweb.com/print/1323296.
Bystrykh. "Generalized DNA Barcode Design Based on Hamming Codes", *PLoS ONE*, 7(5): e36852, 1-8 (2012).
Campana, D., "Progress of Minimal Residual Disease Studies in Childhood Acute Leukemia," Curr Hematol Malig Rep, 5:169-176 (2010).
Campana. "Minimal residual disease in acute lymphoblastic leukemia", *Semin Hematol.*,46(1):100-106 (2009).
Campana, et al. "Role of minimal residual disease monitoring in adult and pediatric acute lymphoblastic leukemia", *Hematol Oncol Clin North Am.*, 23(5): 1083-1098 (2009). doi: 10.1016/j.hoc.2009.07.010.
Campbell et al. "Subclonal phylogenetic structures in cancer revealed by ultra-deep sequencing," *PNAS*, 105(35):13081-13086 (2008).
Caporaso, J.G. et al. "Global patterns of 16S rRNA diversity at a depth of millions of sequences per sample", *PNAS*, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", *Blood*, 113(15): 3553-3557 (2009). doi: 10.1182/blood-2008-08-174839. Epub Feb. 6, 2009.
Carlson et al. "Profiling the repertoire of TCRB usage in induced and natural Treg cells", *The Journal of Immunology*, 186: 62.5, Abstract (2011).
Carlson, et al. "Immune Profiling Suggests an IGH Signaling-Dependent Subtype of Aggressive B-ALL", *Blood*, 120: 1428, Abstract (2012).
Carlson, et al. "Deep sequencing of the human TCRγ and TCRβ repertoires provides evidence that TCRβ rearranges after αβ, γγδT cell commitment". Presented at the ASHG 2011 Conference. Oct. 2011. Poster. 1 page.
Carlson, et al. "Detection of tumor tagging clones in multiple myeloma via high throughput sequencing is robust to significant levels of SHM", Presented for the 2014 ASH Annual Meeting. Poster. 1 page. Dec. 5-9, 2014.
Carlson, C.S. et al. "Using synthetic templates to design an unbiased multiplex PCR assay", *Nature Communications*, 4:2680, pp. 1-9 (2013).
Casali, et al. "Human monoclonals from antigen-specific selection of B lymphocytes and transformation by EBV", *Science*, 234(4775): 476-479, Abstract Only (1986).
Casbon et al. "A method for counting PCR template molecules with application to next-generation sequencing", *Nucleic Acids Research*, 39(12): e81, 8 pages (2011).
Catherwood, M.A. et al., "Improved clonality assessment in germinal centre/post germinal centre non-Hodgkin's lymphomas with high rates of somatic hypermutation", *J. Clin. Pathol.*, 60:524-528, Abstract (2007).
Cavé, H. et al., "Clinical Significance of minimal residual disease in childhood acute lymphoblastic leukemia," *The New England Journal of Medicine*, 339:591-598 (1998).

(56) References Cited

OTHER PUBLICATIONS

Chan et al. "Evaluation of Nanofluidics Technology for High-Throughput SNP Genotyping in a Clinical Setting", *The Journal of Molecular Diagnostics*, 13(3): 305-312 (2011).

Chattopadhyay, et al. "A live-cell assay to detect antigen-specific CD4+T cells with diverse cytokine profiles", *Nat Med.*, 11(10): 1113-1117 (2005). Epub Sep. 25, 2005.

Chen et al. "A novel approach for the analysis of T-cell reconstitution by using a T-cell receptor β-based oligonucleotide microarray in hematopoietic stem cell transplantation", *Exp Hematol.*, 35(5):831-841 (2007).

Chen et al. "Identification of racehorse and sample contamination by novel 24-plex STR system", Forensic Science International: Genetics, 4:158-167 (2010).

Chen, et al. "Microfluidic cell sorter with integrated piezoelectric actuator", *Biomed Microdevices*, 11(6): 1223-1231 (2009). doi: 10.1007/s10544-009-9341-5.

Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).

Chen, et al. "Total Gene Synthesis: Novel Single-Step and Convergent Strategies Applied to the Construction of a 779 Base Pair Bacteriorhodopsis", *Gene. J. Am. Chem Soc.*, 116: 8799-8800, Abstract Only (1994).

Chinese Patent Application No. 2013800628866, English translation of Search Report dated Apr. 11, 2017, 2 pages.

Chinese Patent Application No. 2014800254909, Search Report and English translation, dated May 25, 2017, mailed by the Chinese Patent Office on Jun. 6, 2017, 5 pages.

Chiu, et al. "Non-invasive prenatal assessment of trisomy 21 by multiplexed maternal plasma DNA sequencing: large scale validity study", *BMJ*, 342:c7401, 9 pages (2011). doi: 10.1136/bmj.c7401.

Choi, et al. "Relapse in children with acute lymphoblastic leukemia involving selection of a preexisting drug-resistant subclone", *Blood*, 110(2):632-639 (2007).

Choi, et al. "Clonal evolution in B-lineage acute lymphoblastic leukemia by contemporaneous $V_H$-$V_H$ gene replacements and $V_H$-$DJ_H$ gene rearrangements", *Blood*, 87(6):2506-2512 (1996).

Chothia, C. et al. "Canonical structures for the hypervariable regions of immunoglobulins," *J. Mol. Biol.*, 196:901-917, Abstract only (1987).

Chothia, C. et al. "Conformations of immunoglobulin hypervariable regions," *Nature*, 342:877-883 (1989).

Churchill and Waterman. "The Accuracy of DNA Sequences: Estimating Sequence Quality", *Genomics*, 14:89-98 (1992).

Chute, et al. "Detection of immunoglobulin heavy chain gene rearrangements in classic Hodgkin lymphoma using commercially available BIOMED-2 primers", *Diagn Mol Pathol.*, 17(2): 65-72 (2008). doi: 10.1097/PDM.0b013e318150d695.

Citri et al. "Comprehensive qPCR profiling of gene expression in single neuronal cells", *Nature Protocols*, 7(1): 118-127 (2012).

Ciudad, J. et al. "Detection of abnormalities in B-cell differentiation pattern is a useful tool to predict relapse in precursor-B-ALL", *British Journal of Haematology*, 104:695-705 (1999).

Cleary, et al. "Production of complex nucleic acid libraries using highly parallel in situ oligonucleotide synthesis", *Nat Methods*, 1(3): 241-248 (2004). Epub Nov. 18, 2004.

Clemente, et al. "Deep sequencing of the T-cell receptor repertoire in CD8+T-large granular lymphocyte leukemia identifies signature landscapes", *Blood*, 122(25): 4077-85 (2013). doi: 10.1182/blood-2013-05-506386. Epub Oct. 22, 2013.

Cooper, et al. "BRAF inhibition is associated with increased clonality in tumorin filtrating lymphocytes", Oncoimmunology, 2(10):e26615 (2013). Epub Oct. 15, 2013.

Costabile, et al. "Molecular approaches in the diagnosis of primary immunodeficiency diseases", *Human Mutation*, 27(12):1163-1173 (2006).

Coustan-Smith, E. et al., "Clinical importance of minimal residual disease in childhood acute lymphoblastic leukemia," *Blood*, 96(8):2691-2696 (2000).

Coustan-Smith, E. et al., "Early T-cell precursor leukaemia: a subtype of very high-risk acute lymphoblastic leukaemia," *Lancet Oncology*, 10:147-156 (2009).

Coustan-Smith, E. et al., "Prognostic importance of measuring early clearance of leukemic cells by flow cytometry in childhood acute lymphoblastic leukemia", *Blood*, 100(1):52-58 (2002).

Craig et al. "Identification of genetic variants using bar-coded multiplex sequencing", *Nature Methods*, 5(10): 887-893 (2008) and Supplemental Materials.

Cronin, et al. "Comprehensive next-generation cancer genome sequencing in the era of targeted therapy and personalized oncology", *Biomark Med*, 5(3):293-305 (2011). (Abstract only). doi: 10.2217/bmm.11.37.

Cronn et al. "Multiplex sequencing of plant chloroplast genomes using Solexa sequencing-by-synthesis technology", *Nucleic Acids Research*, 36(19):e122, 1-11 (2008).

Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", *The Journal of Immunology*, 172:1935-1944 (2004).

Curran-Everett, D., "Multiple comparisons: philosophies and illustrations", *Am J Physiol Regulatory Integrative Comp Physiol.*, 279:R1-R8 (2000).

Currier and Robinson. "Spectratype/immunoscope analysis of the expressed TCR repertoire", *Current Protocols in Immunology*, Supplement 38:10.28.1-10.28.24 (2000).

Dahl et al. "Multiplex amplification enabled by selective circularization of large sets of genomic DNA fragments", *Nucleic Acids Res.*, 33(8): e71 (2005).

Damle et al. "B-cell chronic lymphocytic leukemia cells express a surface membrane phenotype of activated, antigen-experienced B lymphocytes", *Blood*, 99(11): 4087-93 (2002).

Dash, P. et al., "Paired analysis of TCR[alpha] and TCR[beta] chains at the single-cell level in mice", *Journal of Clinical Investigation*, 121(1):288-295 (2011).

Davi, et al. "Lymphocytic progenitor cell origin and clonal evolution of human B-lineage acute lymphoblastic leukemia", *Blood*, 88(2):609-621 (1996).

Davila, et al. Efficacy and toxicity management of 19-28z CART cell therapy in B cell acute lymphoblastic leukemia, Sci Transl Med., 6(224):224ra25 (2014). doi: 10.1126/scitranslmed.3008226.

Davis, et al. "Interrogating the repertoire: broadening the scope of peptide-MHC multimer analysis", *Nat Rev Immunol.*, 11(8):551-558 (2011). doi: 10.1038/nri3020.

Davis, et al. "Staining of cell surface human CD4 with 2'-F-pyrimidine-containing RNA aptamers for flow cytometry", *Nucleic Acids Research*, 26(17):3915-3924 (1998).

De Bona et al. "Optimal spliced alignments of short sequence reads", *Bioinformatics*, 9(Suppl 10):O7, 2 pages (2008).

De Jonge, H.J.M., et al. "Evidence Based Selection of Housekeeping Genes," *PLoS One*, 9(e898):1-5 (2007).

Dean, et al. "Rapid amplification of plasmid and phage DNA using Phi 29 DNA polymerase and multiply-primed rolling circle amplification", *Genome Res.*, 11(6): 1095-1099 (2001).

Decoste et al. "Relative and Absolute Quantitative Real-Time PCR-Based Quantifications of hcnC and phlD Gene Transcripts in Natural Soil Spiked with *Pseudomonas* sp. Strain LBUM300", *Applied and Environmental Microbiology*, 77(1): 41-47 (2011).

Dedhia, et al. "Evaluation of DNA extraction methods and real time PCR optimization on formalin-fixed paraffin-embedded tissues", *Asian Pac J Cancer Prev.*, 8(1): 55-59 (2007).

Deiman, et al. "Characteristics and applications of nucleic acid sequence-based amplification (NASBA)", *Mol Biotechnol.*, 20(2): 163-179, Abstract Only (2002).

DeKosky et al. "High-throughput sequencing of the paired human immunoglobulin heavy and light chain repertoire", *Nature Biotechnology*, 31(2): 166-169 (2013).

(56) References Cited

OTHER PUBLICATIONS

Delaney, et al. "Evolution and Clinical Implications of the T cell Repertoire Following Cord Blood Transplant", Biology of Blood and Marrow Transplant, vol. 19, Issue 2, S201-S202. Published Feb. 2013.

Deng et al. "Gene profiling involved in immature CD4+T lymphocyte responsible for systemic lupus erythematosus", Molecular Immunology, 43:1497-1507 (2006).

Denkert, Carsten, et al. "Tumor-Associated Lymphocytes as an Independent Predictor of Response to Neoadjuvant Chemotherapy in Breast Cancer." Journal of Clinical Oncology (2009); 28(1): 105-113.

DeNucci, C.C. et al. "Integrin function in T-cell homing to lymphoid and nonlymphoid sites: getting there and staying there," Critical Reviews in Immunology, 29(2):87-109 (2009).

Deschoolmeester, et al. "Tumor infiltrating lymphocytes: an intriguing player in the survival of colorectal cancer patients", BMC Immunology, 11:19, 12 pages (2010). doi: 10.1186/1471-2172-11-19.

Desmarais, et al. "Deep profiling of the mouse TCRβ CDR3 region in thymus and spleen". Oct. 2010. Poster. 1 page.

Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.

Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).

Dheda, K., et al. "Validation of housekeeping genes for normalizing RNA expression in real-time PCR," Bio Techniques, 37:112-119 (2004).

Dictor et al. "Resolving T-cell receptor clonality in two and genotype in four multiplex polymerase chain reactions", Haematologica, 90(11): 1524-1532 (2005).

Diederichsen, et al. "Prognostic value of the CD4+/CD8+ ratio of tumour infiltrating lymphocytes in colorectal cancer and HLA-DR expression on tumour cells", Cancer Immunol Immunother., 52(7):423-428 (2003). Epub Apr. 15, 2003.

Diehl, et al. "BEAMing: single-molecule PCR on microparticles in water-in-oil emulsions", Nat Methods, 3(7):551-559, Abstract Only (2006).

Dik, W., et al. "New insights on human T cell development by quantitative T cell receptor gene rearrangement studies and gene expression profiling," JEM, 201(11):1715-1723 (2005).

Diluvio et al. "Identical TCRβ-chain rearrangements in streptococcal angina and skin lesions of patients with psoriasis vulgaris", J Immunol., 176(11 ): 7104-11 (2006).

Ding, et al. "Clonal evolution in relapsed acute myeloid leukaemia revealed by whole-genome sequencing", Nature, 481(7382):506-510 (2012). doi: 10.1038/nature10738.

Diviacco, et al. "A novel procedure for quantitative polymerase chain reaction by coamplification of competitive templates", Gene, 122(2):313-320 (1992).

Do and Batzoglou. "What is the expectation maximization algorithm? ", Nature Biotechnology, 26(8): 897-899 (2008).

Dobosy, J. et al. "RNase H-dependent PCR (rhPCR): improved specificity and single nucleotide polymorphism detection using blocked cleavable primers", BMC Biotechnology, 11(80):1-18 (2011).

Dohm, et al. "Substantial biases in ultra-short read data sets from high throughput DNA sequencing", Nucleic Acids Research, 36:e105, 10 pages (2008).

Dou, et al. "Analysis of T cell receptor $V_\beta$ gene usage during the course of disease in patients with chronic hepatitis B", Journal of Biomedical Science, 5(6):428-434 (1998).

Dressman, et al. "Transforming single DNA molecules into fluorescent magnetic particles for detection and enumeration of genetic variations", PNAS, 100(15):8817-8822 (2003). Epub Jul. 11, 2003.

Drmanac, et al. "Human genome sequencing using unchained base reads on self-assembling DNA nanoarrays", Science, 327(5961):78-81 (2010). doi: 10.1126/science.1181498. Epub Nov. 5, 2009.

Droege, et al. "The Genome Sequencer FLX System—longer reads, more applications, straight forward bioinformatics and more complete data sets", J Biotechnol., 136(1-2):3-10 (2008). doi: 10.1016/j.jbiotec.2008.03.021. Epub Jun. 21, 2008.

Droese, J., et al. "Validation of BIOMED-2 multiplex PCR tubes for detection of TCRB gene rearrangements in T-cell malignancies," Leukemia, 18:1531-1538 (2004).

Drossman, et al. "High-speed separations of DNA sequencing reactions by capillary electrophoresis", Anal Chem., 62(9): 900-903 (1990).

Du et al. "TCR spectratyping revealed T lymphocytes associated with graft-versus-host disease after allogeneic hematopoietic stem cell transplantation", Leukemia & Lymphoma, 48(8):1618-1627 (2007).

Duby, A.D. et al., "Human T-cell receptor aberrantly rearranged beta-chain J1.5-Dx-J2.1 gene," PNAS, GenBank accession No. M13574.1, bases 1 to 100, 4 pages (1986).

Dudgeon, et al. "The evolution of thymic lymphomas in p53 knockout mice", Genes Dev., 28(23): 2613-20 (2014). doi: 10.1101/gad.252148.114.

Dunn, et al. "Focus on TILs: Prognostic significance of tumor infiltrating lymphocytes in human glioma", Cancer Immun., 7:12, 16 pages (2007).

Dziubianau, M., et al., "TCR repertoire analysis by next generation sequencing allows complex differential diagnosis of T cell-related pathology." Am J Transplant (2013); 13(11): 2842-2854. doi: 10.1111/ajt.12431. Epub Sep. 10, 2013.

Eason et al. "Characterization of synthetic DNA bar codes in Saccharomyces cerevisiae gene-deletion strains," PNAS, 101(30): 11046-11051 (2004).

Edd et al. "Controlled encapsulation of single cells into monodisperse picoliter drops", Lab Chip, 8(8):1262-1264 (2008).

Edwards and Gibbs, "Multiplex PCR: advantages, development, and applications," Genome Research, 3:565-575 (1994).

Eichler, et al. "Haplotype and interspersion analysis of the FMR1 CGG repeat identifies two different mutational pathways for the origin of the fragile X syndrome", Hum Mol Genet., 5(3):319-330 (1996).

Eichler, et al. "Length of uninterrupted CGG repeats determines instability in the FMR1 gene", Nat Genet., 8(1):88-94, Abstract Only (1994).

Eid et al. "Real-time DNA sequencing from single polymerase molecules", Science, 323(5910):133-138 (2009). doi: 10.1126/science.1162986. Epub Nov. 20, 2008.

Eis, et al. "An invasive cleavage assay for direct quantitation of specific RNAs", Nat Biotechnol., 19(7):673-676, Abstract Only (2001).

Eisenstein. "Personalized, sequencing-based immune profiling spurs startups", Nat Biotechnol., 31(3):184-186 (2013). doi: 10.1038/nbt0313-184b.

Elkord et al. "T regulatory cells in cancer: recent advances and therapeutic potential", Expert Opinion on Biological Therapy, 10(11): 1573-1586 (2010).

Elnifro, E.M., et al. "Multiplex PCR: Optimization and Application in Diagnostic Virology", Clinical Microbiology Reviews, 13(4):559-570 (2000).

Emerson, et al. "Correlation of TCR diversity with immune reconstitution after cord blood transplant", Presented at the American Society of Clinical Oncology's annual meeting. May, 2012. Poster. 1 page.

Emerson et al. "Defining the Alloreactive T Cell Repertoire Using High-Throughput Sequencing of Mixed Lymphocyte Reaction Culture", PLoS One, 9(11): e111943 (2014).

Emerson, R.O. et al. "High-throughput sequencing of T-cell receptors reveals a homogeneous repertoire of tumour-infiltrating lymphocytes in ovarian cancer", Journal of Pathology, 231: 433-440 (2013).

(56) References Cited

OTHER PUBLICATIONS

Emerson, et al. "CD4+0 and CD8+ T cell β antigen receptors have different and predictable V and J gene usage and CDR3 lengths", Presented at the Annual Meeting of the American Association of Immunologists 2012 in Boston, MA May 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, et al. TCR repertoire diversity assessed with immunosequencing is associated with patient mortality following cord blood transplant. Presented for the 2014 ASH Annual Meeting. Poster. 1 page. Dec. 5-9, 2014.
Estorninho, et al. "A novel approach to tracking antigen-experienced CD4 T cells into functional compartments via tandem deep and shallow TCR clonotyping", J Immunol., 191(11): 5430-5440 (2013). doi: 10.4049/jimmunol.I300622. Epub Oct. 25, 2013.
Erlich, et al. "Alta-Cyclic: a self-optimizing base caller for next-generation sequencing", Nat Methods., 5(8): 679-682 (2008). doi: 10.1038/nmeth.1230. Epub Jul. 6, 2008.
European Application No. 09764927.1, Notice of Opposition dated Oct. 14, 2014, Reference# 547-7.
European Application No. 09764927.1, Notice of Opposition dated Oct. 14, 2014, Reference# BR0-0001EP.
European Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", Lung Cancer, 59(1): 32-40 (2008).
European Patent Application No. 13195379.6, European Search Report and Opinion dated Mar. 13, 2014, 6 pages.
European Patent Application No. 11777704.5, European Search Report dated Jul. 26, 2013, 6 pages.
European Patent Application No. 16183402.3, Extended European Search Report dated Feb. 21, 2017, 8 pages.
European Patent Application No. 12854963.1, Extended European Search Report dated Jun. 10, 2015, 5 pages.
European Patent Application No. 15735285.7, Extended European Search Report dated Jul. 19, 2017, 7 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
Ewing and Green, "Base-calling of automated sequencer traces using Phred. I. Accuracy Assessment," Genome Research, 8: 175-185 (1998).
Faham, M. et al. "Deep-sequencing approach for minimal residual disease detection in acute lymphoblastic leukemia", Blood, 120(26): 5173-5180 (2012).
Felsenstein, et al. "Evolutionary Trees from DNA Sequences: A Maximum Likelihood Approach", J Mol Evol, 17:368-376 (1981).
Ferradini et al. "Analysis of T Cell Receptor Variability in Tumor-infiltrating Lymphocytes from a Human Regressive Melanoma", J. Clin. Invest., pp. 1183-1190 (1993).
Ferrero, et al. "Multiple myeloma shows no. intra-disease clustering of immunoglobulin heavy chain genes", Haematologica, 97(6): 849-853 (2012). doi: 10.3324/haematol.2011.052852. Epub Dec. 29, 2011.
Fisher et al. "The Relation Between the Number of Species and the Number of Individuals in a Random Sample of an Animal Population", Journal of Animal Ecology, 12(1): 42-58 (1943).
Flaherty et al. "Ultrasensitive detection of rare mutations using next-generation targeted resequencing", Nucleic Acids Research, 40(1): e2, 12 pages (2012).
Flicek and Birney, "Sense from sequence reads: methods for alignment and assembly," Nature Methods Supplement, 6(11s): S6-S12 (2009).
Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", Leukemia, 22:771-782 (2008).
Frampton, et al. "Development and validation of a clinical cancer genomic profiling test based on massively parallel DNA sequencing", Nat Biotechnol., 31(11): 1023-1031 (2013). doi: 10.1038/nbt.2696. Epub Oct. 20, 2013.
Frank. "BARCRAWL and BARTAB: software tools for the design and implementation of barcoded primers for highly multiplexed DNA sequencing," BMC Bioinformatics, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", Biotechniques, 6(1): 112-125 (1999).
Freeman, J.D., et al. "Profiling the T-Cell Receptor Beta-Chain Repertoire by Massively Parallel Sequencing", Genome Research, 19(10):1817-1824 (2009). Epub Jun. 18, 2009.
Fridman, et al. "Prognostic and predictive impact of intra- and peritumoral immune infiltrates", Cancer Research, 71(17): 5601-5605 (2011). doi: 10.1158/0008-5472.CAN-11-1316. Epub Aug. 16, 2011.
Fritz et al. "Alterations in the spinal cord T cell repertoire during relapsing experimental autoimmune encephalomyelitis," J Immunol, 164:6662-6668 (2000).
Fu et al. "Counting individual DNA molecules by the stochastic attachment of diverse labels", PNAS, 108(22): 9026-9031 and Supporting Materials, 8 pages (2011).
Fuller, et al. "The challenges of sequencing by synthesis", Nat Biotechnol., 7(11): 1013-1023 (2009) (Abstract only). doi: 10.1038/nbt.1585. Epub Nov. 6, 2009.
Furmanski, et al. "Public T cell receptor β-chains are not advantaged during positive selection", The Journal of Immunology, 180(2): 1029-1039 (2008).
García-Castillo and Núñez, et al. "Detection of clonal immunoglobulin and T-cell receptor gene recombination in hematological malignancies: monitoring minimal residual disease", Cardiovascular & Haematological Disorders-Drug Targets, 9:124-135 (2009).
Gauss, et al. "Mechanistic constraints on diversity in human V(D)J recombination", Mol Cell Biol., 16(1):258-269 (1996).
Gawad, et al. "Massive evolution of the immunoglobulin heavy chain locus in children with B precursor acute lymphoblastic leukemia", Blood, 120(22):4407-4417 (2012). doi: 10.1182/blood-2012-05-429811. Epub Aug. 28, 2012.
Gerlinger and Swanton. "How Darwinian models inform therapeutic failure initiated by clonal heterogeneity in cancer medicine", British Journal of Cancer, 103(8):1139-1143 (2010). doi: 10.1038/sj.bjc.6605912. Epub Sep. 28, 2010.
Gerlinger, M. et al. "Ultra deep T cell receptor sequencing reveals the complexity and intratumour heterogeneity of T cell clones in renal cell carcinomas", Journal of Pathology, 231:424-432 (2013).
Germano, et al. "Clonality profile in relapsed precursor-B-ALL children by GeneScan and sequencing analyses. Consequences on minimal residual disease monitoring", Leukemia, 17(8):1573-1582 (2003).
Giannoni, et al. Allelic exclusion and peripheral reconstitution by TCR transgenic T cells arising from transduced human hematopoietic stem/progenitor cells, Mol Ther., 21(5):1044-1054 (2013). doi: 10.1038/mt.2013.8. Epub Feb. 5, 2013.
GIGA—Roche 454 FLX technology how it works. Fiche technique du Centre Interdisciplinaire de Genoproteomique Appliquee (Universite de Liege, Belgique). Accessed Oct. 15, 2014.
Gilbert, et al. "The isolation of nucleic acids from fixed, paraffin-embedded tissues-which methods are useful when?", PLoS One, 2(6):e537, 12 pages (2007).
Giuggio, et al. "Evolution of the intrahepatic T cell repertoire during chronic hepatitis C virus infection", Viral Immunology, 18(1):179-189 (2005).
Gloor et al. "Microbiome profiling by Illumine sequencing of combinatorial sequence-tagged PCR products," PLoS ONE, 5(10): e15406, 15 pages (2010).

(56) References Cited

OTHER PUBLICATIONS

Godelaine, et al. "Polyclonal CTL responses observed in melanoma patients vaccinated with dendritic cells pulsed with a MAGE-3.A1 peptide", *J Immunol.*, 171(9):4893-4897 (2003).
Golembowski, et al. "Clonal evolution in a primary cutaneous follicle center B cell lymphoma revealed by single cell analysis in sequential biopsies", *Immunobiology*, 201(5):631-644 (2000).
Gomes, et al. "Single-tube nested PCR using immobilized internal primers for the identification of dengue virus serotypes", *J Virol Methods.*, 145(1):76-9 (2007). Epub Jun. 15, 2007.
Gonzalez, et al. "Incomplete DJH rearrangements of the IgH gene are frequent in multiple myeloma patients: immunobiological characteristics and clinical implications", *Leukemia*, 17:1398-1403 (2003).
Gonzalez et al., "Incomplete DJH rearrangements as a novel tumor target for minimal residual disease quantitation in multiple myeloma using real-time PCR", *Leukemia*, 17:1051-1057 (2003).
Gonzalez, S.F., et al. "Trafficking of B Cell Antigen in Lymph Nodes", *Ann. Rev. Immunol.*, 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", *J Immunol.*, 152(10):5109-5119 (1994).
Gottenberg, et al. "Markers of B-lymphocyte activation are elevated in patients with early rheumatoid arthritis and correlated with disease activity in the ESPOIR cohort", *Arthritis Res Ther.*, 11(4):R114 (2009). doi: 10.1186/ar2773. Epub Jul. 23, 2009.
Gratama and Kern. "Flow cytometric enumeration of antigen-specific T lymphocytes", *Cytometry A*, 58(1): 79-86 (2004).
Gratama, et al. "Measuring antigen-specific immune responses", 2008 update. *Cytometry A.*, 73(11): 971-974 (2008). doi: 10.1002/cyto.a.20655.
Green, et al. "Clonal diversity of Ig and T-cell-receptor gene rearrangements identifies a subset of childhood B-precursor acute lymphoblastic leukemia with increased risk of relapse", *Blood*, 92(3):952-958 (1998).
Greenberg, et al. "Profile of immunoglobulin heavy chain variable gene repertoires and highly selective detection of malignant clonotypes in acute lymphoblastic leukemia" *J Leukoc Biol*, 57(6):856-864 (1995).
Greenman, et al. "Patterns of somatic mutation in human cancer genomes", *Nature*, 446(7132): 153-158 (2007).
Gribben, JG. "Stem cell transplantation in chronic lymphocytic leukemia", *Biol. Blood Marrow Transplant.*, 15(1 Suppl): 53-58 (2009). doi: 10.1016/j.bbmt.2008.10.022.
Grupp, et al. "Chimeric antigen receptor-modified T cells for acute lymphoid leukemia", N Engl J Med., 368(16):1509-1518 (2013). doi: 10.1056/NEJMoa1215134. Epub Mar. 25, 2013.
Grupp, et al. "Adoptive transfer of autologous T cells improves T-cell repertoire diversity and long-term B-cell function in pediatric patients with neuroblastoma", Clin Cancer Res., 18(24):6732-6741 (2012). doi: 10.1158/1078-0432.CCR-12-1432. Epub Oct. 23, 2012.
Gulliksen, et al. "Real-time nucleic acid sequence-based amplification in nanoliter volumes", *Anal Chem.*, 76(1): 9-14, Abstract Only (2004).
Gunderson et al. "Decoding Randomly Ordered DNA Arrays", *Genome Research*, 14: 870-877 (2004).
Guo, et al. "Sequence changes at the V-D junction of the $V_H1$ heavy chain of anti-phosphocholine antibodies alter binding to and protection against *Streptococcus pneumoniae*", *Int Immunol.*, 9(5):665-677 (1997).
Gupta, Pushpendra K. "Single-molecule DNA sequencing technologies for future genomics research", *Trends Biotechnol.*, 26(11): 602-611 (2008). doi: 10.1016/j.tibtech.2008.07.003. Epub Aug. 21, 2008.

Gurrieri, et al. "Chronic lymphocytic leukemia B cells can undergo somatic hypermutation and intraclonal immunoglobulin $V_HDJ_H$ gene diversification", *J Exp Med.*, 196(5):629-639 (2002).
Hadrup, et al. "Parallel detection of antigen-specific T-cell responses by multidimensional encoding of MHC multimers", *Nat Methods*, 6(7): 520-526 (2009) (Abstract Only). doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for suboptimal specimens", *Leukemia & Lymphoma*, 48(7): 1338-1343 (2007).
Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.
Han et al. "Immunorepertoire analysis by multiplex PCR amplification and high throughput sequencing", *The Journal of Immunology*, 182:42.6, 1 page (2009).
Hanahan, et al. "Hallmarks of cancer: the next generation", *Cell*, 144(5): 646-674 (2011). doi: 10.1016/j.cell.2011.02.013.
Harismendy et al. "Evaluation of next generation sequencing platforms for population targeted sequencing studies", *Genome Biology*, 10:R32, 13 pages (2009).
Harris et al. "Single-Molecule DNA Sequencing of a Viral Genome", *Science*, 320: 106-109 (2008).
Hathcock, et al. "ATM influences the efficiency of TCRβ rearrangement, subsequent TCRβ-dependent T cell development, and generation of the pre-selection TCRβ CDR3 repertoire", PLoS One, 84):e62188 (2013). doi: 10.1371/journal.pone.0062188. Print 2013.
Hawkins, et al. "Whole genome amplification—applications and advances", *Curr Opin Biotechnol.*, 13(1): 65-67 (2002).
He, et al. "IgH gene rearrangements as plasma biomarkers in Non-Hodgkin's lymphoma patients", *Oncotarget*, 2(3): 178-185 (2011).
Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_I=10&hq_v=2357e2f0b3. Accessed Apr. 6, 2011.
Heger. "Roche's 454 Eyes Immune Repertoire Sequencing as Key Application for Long-Read Platform". Feb. 2, 2010. 4 pages. http://www.genomeweb.com/print/932624.
Henegariu, O. et al., "Multiplex PCR: Critical Parameters and Step-By-Step Protocol," Biotechniques, Informa HealthCare, 23(3):504-511 (1997).
Hensel et al. "Simultaneous identification of bacterial virulence genes by negative selection", *Science*, 269(5222): 400-403 (1995).
Hill, et al. "Using ecological diversity measures with bacterial communities", *FEMS Microbiol Ecol.*, 43(1):1-11 (2003). doi: 10.1111/j.1574-6941.2003.tb01040.x.
Hirohata, et al. "Regulation of human B cell function by sulfasalazine and its metabolites", *Int Immunopharmacol.*, 2(5): 631-640, Abstract Only (2002).
Hodges, E. et al. "Diagnostic role of tests for T cell receptor (TCR) genes", *J Clin Pathol.*, 56(1): 1-11 (2003).
Holder and Lewis. "Phylogeny estimation: traditional and bayesian approaches", Nat Rev Genet., 4(4): 275-84 (2009).
Holt. "Q &A: BC cancer agency's Robert Holt on sequencing the immune repertoire in immune reconstitution," *Genome Web* (www.genomeweb.com) Jun. 30, 2009.
Holt and Jones. "The new paradigm of flow cell sequencing", *Genome Research*, 18:839-846 (2008).
Hoogenboom, et al. "Multi-subunit proteins on the surface of filamentous phage: methodologies for displaying antibody (Fab) heavy and light chains", *Nucleic Acids Res.*, 19(15): 4133-4137 (1991).
Hoogendoorn, et al. "Primary allogeneic T-cell responses against mantle cell lymphoma antigen-presenting cells for adoptive immunotherapy after stem cell transplantation", *Clin Cancer Res.*, 11(14): 5310-5318 (2005).
Hoos, et al. "Improved endpoints for cancer immunotherapy trials", *J Natl Cancer Inst.*, 102(18): 1388-1397 (2010). doi: 10.1093/jnci/djq310. Epub Sep. 8, 2010.

(56) References Cited

OTHER PUBLICATIONS

Hoover and Lubkowski. "DNAWorks: an automated method for designing oligonucleotides for PCR-based gene synthesis", *Nucleic Acids Res.*, 30(10): e43, 7 pages (2002).

Hosono, et al. "Unbiased whole-genome amplification directly from clinical samples", *Genome Res.*, 13(5): 954-964 (2003). Epub Apr. 14, 2003.

Hoven, et al. "Detection and isolation of antigen-specific B cells by the fluorescence activated cell sorter (FACS)", *J Immunol Methods*, 117(2): 275-284, Abstract Only, 2 pages (1989).

Howe, et al. "T cell receptor clonotype analysis of T cell responses: Diagnostic application of a clonotypic database", *Blood*, 102:Abstract 3918 (2003).

Huang, et al. "Isolation of cell-free DNA from maternal plasma using manual and automated systems", *Methods Mol Biol.*, 444: 203-208, Abstract Only (2008). doi: 10.1007/978-1-59745-066-9_15.

Huh, et al. "Microfluidics for flow cytometric analysis of cells and particles", *Physiol Meas.*, 26(3): R73-98, Abstract Only (2005). Epub Feb. 1, 2005.

Huijsmans, et al. "Comparative analysis of four methods to extract DNA from paraffin-embedded tissues: effect on downstream molecular applications", *BMC Res Notes*, 3:239, 9 pages (2010). doi: 10.1186/1756-0500-3-239.

Huse, et al. "Generation of a large combinatorial library of the immunoglobulin repertoire in phage lambda", *Science*, 246(4935): 1275-1281, Abstract Only (1989).

Huse et al. "Accuracy and quality of massively parallel DNA pyrosequencing", *Genome Biology*, 8: R143 (2007).

Hwang, H.Y. et al. "Identification of a Commonly used CDR3 Region of Infiltrating T Cells Expressing Vβ13 and Vβ15 Derived from Psoriasis Patients", *The Journal of Investigative Dermatology*, 120(3):359-364 (2003).

Iancu, et al. "Profile of a serial killer: cellular and molecular approaches to study individual cytotoxic T-cells following therapeutic vaccination", *J Biomed Biotechnol.*, 2011: 452606 (2011). doi: 10.1155/2011/452606. Epub Nov. 14, 2010.

Illumina. Genome analyzer pipeline software version 1.0 user guide. Part #1004759, 176 pages (2008).

Illumina. Data Sheet: Sequencing. Genomic Sequencing. Pub. No. 770.2008-016 Reference states: "Current as of Jan. 30, 2009", 6 pages, Copyright 2010.

Illumina. Data Sheet, "TruSeq™ exome enrichment kit", 5 pages (2011).

Illumina Systems & Software, Technology Spotlight, DNA Sequencing with Solexa® Technology, Illumina, Inc., Pub. No. 770-2007-002, 4 pages (2007).

Illumina. "Technical Note: Systems and Software. Calling sequencing SNPs", 3 pages (2010).

Illumina. TruSeq Sample Preparation Kit and Data Sheet. Illumina, Inc., San Diego, CA, 4 pages (2011).

Ishii et al. "Isolation and expression profiling of genes upregulated in the peripheral blood cells of systemic lupus erythematosus patients," *DNA Research*, 12:429-439 (2005).

Jabara et al. "Accurate sampling and deep sequencing of the HIV-1 protease gene using a Primer ID", *PNAS*, 108(50): 20166-20171 (2011).

Jacobi et al. "Activated memory B cell subsets correlate with disease activity in systemic lupus erythematosus: delineation by expression of CD27, IgD, and CD95", *Arthritis & Rheumatism*, 58(6):1762-1773 (2008).

Jacobi et al. "Correlation between circulating CD27$^{high}$ plasma cells and disease activity in patients with systemic lupus erythematosus" *Arthritis & Rheumatism*, 48(5):1332-1342 (2003).

Jaffe, et al. "Classification of lymphoid neoplasms: the microscope as a tool for disease discovery", *Blood*, 112(12): 4384-4399 (2008). doi: 10.1182/blood-2008-07-077982.

Jalla, et al. "Enumeration of lymphocyte subsets using flow cytometry: Effect of storage before and after staining in a developing country setting", *Indian J Clin Biochem.*, 19(2): 95-99 (2004). doi: 10.1007/BF02894264.

Jena, et al. "Amplification of genes, single transcripts and cDNA libraries from one cell and direct sequence analysis of amplified products derived from one molecule", *J. Immunol. Methods*, 190:199-213 (1996).

Jochems and Schlom. "Tumor-infiltrating immune cells and prognosis: the potential link between conventional cancer therapy and immunity", *Exp Biol Med* (Maywood), 236(5): 567-579 (2011). doi: 10.1258/ebm.2011.011007. Epub Apr. 12, 2011.

Jones, et al. "Human autoimmunity after lymphocyte depletion is caused by homeostatic T-cell proliferation", Proc Natl Acad Sci USA, 110(50) :20200-20205 (2013). doi: 10.1073/pnas. 1313654110. Epub Nov. 26, 2013.

Jung, et al. "Unraveling V(D)J recombination; insights into gene regulation", *Cell*, 116(2): 299-311 (2004).

Jurkat, Clone 6-1 (ATCC TIB-152) Webpage retrievable from the ATCC under http://www.lgcstandards-atcc.org/Products/ All MB-152.aspx#characteristics. Accessed Oct. 14, 2014.

Kalinina, O. et al. "Nanoliter scale PCR with TaqMan detection", *Nucleic Acids Research*, 25(10):1999-2004 (1997).

Kalos, M. et al. "T Cells with Chimeric Antigen Receptors Have Potent Antitumor Effects and Can Establish Memory in Patients with Advanced Leukemia", *Science Translational Medicine*, 3(95ra73): 1-11 (2011).

Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt. 2012.06.005. Epub Jun. 12, 2012.

Kaplinski and Remm. "MultiPLX Automatic Grouping and Evaluation of PCR Primers", *Methods in Molecular Biology*, 402(PCR Primer Design):287-303 (2004).

Kato et al. "Analysis of accumulated T cell clonotypes in patients with systemic lupus erythematosus," *Arthritis & Rheumatism*, 43(12):2712-2721 (2000).

Katz, S.C. et al. "T Cell Infiltrate Predicts Long-Term Survival Following Resection of Colorectal Cancer Liver Metastases," *Ann. Surg. Oncol.*, 16:2524-2530 (2009).

Kedzierska, et al. "Tracking phenotypically and functionally distinct T cell subsets via T cell repertoire diversity", *Mol Immunol.*, 45(3): 607-618 (2008). Epub Aug. 24, 2007.

Kehrl, J.H. et al. "Chemoattractant Receptor Signaling and Its Role in Lymphocyte Motility and Trafficking", *Current Topics in Microbiology and Immunology*, 334:107-127 (2009).

Kiianitsa, et al., "Development of Tools for T-Cell Repertoire Analysis (TCRB Spectratyping) for the Canine Model of Hematopoietic Cell Transplantation", *Blood*, ASH-Annual Meeting Abstracts, 110:Abstract 4873, 2 pages (2007).

Kim, et al. "An efficient and reliable DNA extraction method for preimplantation genetic diagnosis: a comparison of allele drop out and amplification rates using different single cell lysis methods", *Fertility and Sterility*, 92: 814-818 (2009).

Kim, et al. "Polony multiplex analysis of gene expression (PMAGE) in mouse hypertrophic cardiomyopathy", *Science*, 316(5830):1481-1484 (2007).

Kinde et al. "Detection and quantification of rare mutations with massively parallel sequencing," *PNAS*, 108(23): 9530-9535 and Supporting Information, 16 pages (2011).

Kircher, et al. "Improved base calling for the Illumina Genome Analyzer using machine learning strategies", *Genome Biol.*, 10(8): R83, 9 pages (2009). doi: 10.1186/gb-2009-10-8-r83. Epub Aug. 14, 2009.

Kirsch, et al. "Defining immunoglobulin somatic hypermutation in de novo diffuse large b-cell lymphoma patients: potential application prognosis and risk stratification", Presented for the 2014 ASH Annual Meeting. Poster. 1 page. Dec. 5-9, 2014.

Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.

(56) References Cited

OTHER PUBLICATIONS

Kita, et al. "T cell receptor clonotypes in skin lesions from patients with systemic lupus erythematosus", *Journal of Investigative Dermatology*,110(1): 41-46 (1988).
Kivioja et al. "Counting absolute numbers of molecules using unique molecular identifiers," *Nature Methods*, 9(1): 72-76 (2012).
Klarenbeek, P.L. et al. "Human T-cell memory consists mainly of unexpanded clones", *Immunology Letters*, 133: 42-48 (2010).
Klebanoff, et al. "Therapeutic cancer vaccines: are we there yet?", *Immunol Rev.*, 239(1): 27-44 (2011). doi: 10.1111/j.1600-065X.2010.00979.x.
Klenerman, et al. "Tracking T cells with tetramers: new tales from new tools", *Nat Rev Immunol.*, 2(4):263-272 (2002).
Kneba, M., et al. "Analysis of Rearranged T-cell Receptor β-Chain Genes by Polymerase Chain Reaction (PCR) DNA Sequencing and Automated High Resolution PCR Fragment Analysis", *Blood*, 86:3930-3937 (1995).
Kneba, et al. "Characterization of clone-specific rearrangement T-cell receptor gamma-chain genes in lymphomas and leukemias by the polymerase chain reaction and DNA sequencing", *Blood*, 84(2):574-581 (1994).
Kobari, et al. "T cells accumulating in the inflamed joints of a spontaneous murine model of rheumatoid arthritis become restricted to common clonotypes during disease progression", *Int Immunol.*, 16(1):131-138 (2004).
Koboldt et al., "VarScan: variant detection in massively parallel sequencing of individual and pooled samples", Bioinformatics, 25(17): 2283-2285 (2009).
Koch, et al. "Tumor infiltrating T lymphocytes in colorectal cancer: Tumor-selective activation and cytotoxic activity in situ," *Ann Surg.*, 244(6): 986-992; discussion 992-993 (2006).
Kojima et al. "PCR amplification from single DNA molecules on magnetic beads in emulsion: application for high-throughput screening of transcription factor targets", *Nucleic Acids Research*, 33: 17, e150, 9 pages (2005).
Kohlmann, et al. "Integration of next-generation sequencing into clinical practice: are we there yet?", *Semin Oncol.*, 39(1): 26-36, Abstract Only (2012). doi: 10.1053/j.seminoncol.2011.11.008.
Kotlan, Beatrix, et al. "Immunoglobulin variable regions usage by B-lymphocytes infiltrating a human breast medullary carcinoma." Immunology Letters (1999); 65(3): 143-151.
Kou, et al. "T-Cell receptor Vbeta repertoire CDR3 length diversity differs within CD45RA and CD45RO T-cell subsets in healthy and human immunodeficiency virus-infected children", *Clin Diagn Lab Immunol.*, 7(6):953-9 (2000).
Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).
Krueger, et al. "Large scale loss of data in low-diversity illumina sequencing libraries can be recovered by deferred cluster calling", *PLoS One*, 6(1): e16607, 7 pages (2011). doi: 10.1371/journal.pone.0016607.
Ku, et al. "Exome sequencing: dual role as a discovery and diagnostic tool", *Ann Neurol.*, 71(1):5-14, Abstract Only (2012). doi: 10.1002/ana.22647.
Kumar, et al. "PEG-labeled nucleotides and nanopore detection for single molecule DNA sequencing by synthesis", *Sci Rep.*, 2:684, 8 pages (2012). Epub Sep. 21, 2012.
Kwak, et al. "Induction of immune responses in patients with B-cell lymphoma against the surface-immunoglobulin idiotype expressed by their tumors", *N Engl J Med.*, 327(17):1209-1215 (1992).
Kyu et al. "Frequencies of human influenza-specific antibody secreting cells or plasmablasts post vaccination from fresh and frozen peripheral blood mononuclear cells", *Journal of Immunological Methods*, 340: 42-47 (2009).
Ladányi, A., et al. "Prognostic impact of B-cell density in cutaneous melanoma", *Cancer Immunol. Immunother*, 60(12): 1729-1738 (2011).

Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", *Blood*, vol. 120, No. 21, Abstract 788 (Conference Abstract), Entire Abstract (2012).
Ladetto, M. et al. "Real-time polymerase chain reaction in multiple myeloma: Quantitative analysis of tumor contamination of stem cell harvests", *Experimental Hematology*, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).
Landwehr-Kenzel, et al. "Novel GMP-compatible protocol employing an allogeneic B cell bank for clonal expansion of allospecific natural regulatory T cells", Am J Transplant., 14(3):594-606 (2014). doi: 10.1111/ajt.12629. Epub Jan. 27, 2014.
Langerak, et al. "Immunoglobulin/T-cell receptor clonality diagnostics", *Expert Opin. Med. Diagn.*, 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).
Laplaud et al. "Blood T-cell receptor β chain transcriptome in multiple sclerosis. Characterization of the T cells with altered CDR3 length distribution", *Brain*, 127:981-995 (2004).
Laplaud et al. "Serial blood T cell repertoire alterations in multiple sclerosis patients; correlation with clinical and MRI parameters", *Journal of Neuroimmunology*, 177(1-2):151-160 (2006).
Larimore, K., et al. "Shaping of Human Germline IgH Repertoires Revealed by Deep Sequencing", *The Journal of Immunology*, 189(6): 3221-3230 (2012).
Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).
Lazareva-Ulitsky et al, "On the quality of tree-based protein classification," Bioinformatics, 21(9): 1876-1890 (2005).
Lee, et al. "Characterization of circulating T cells specific for tumor-associated antigens in melanoma patients", *Nat Med.*, 5(6): 677-685, Abstract Only (1999).
Lee, et al. "Prognostic implications of type and density of tumour-infiltrating lymphocytes in gastric cancer", *Br J Cancer*, 99(10): 1704-1711 (2008). doi: 10.1038/sj.bjc.6604738. Epub Oct. 21, 2008.
Lefranc. "IMGT, the international ImMunoGeneTics database", *Nucleic Acids Res.*, 31(1):307-310 (2003).
Leiden, J.M. et al. "The Complete Primary Structure of the T-Cell Receptor Genes From an Alloreactive Cytotoxic Human T-Lymphocyte Clone", *Immunogenetics*, 24(1): 17-23 (1986).
Leisner, et al. "One-pot, mix-and-read peptide-MHC tetramers", *PLoS One*, 3(2):e1678, 11 pages (2008). doi: 10.1371/journal.pone.0001678.
Lennon, et al. "A scalable, fully automated process for construction of sequence-ready barcoded libraries for 454", *Genome Biol.*, 11(2):R15, 9 pages (2010). doi: 10.1186/gb-2010-11-2-r15. Epub Feb. 5, 2010.
Leary, et al. "Development of personalized tumor biomarkers using massively parallel sequencing", Sci Transl Med., 2(20): 20ra14 (2010). doi: 10.1126/scitranslmed.3000702.
Leone, et al. "Molecular beacon probes combined with amplification by NASBA enable homogeneous, real-time detection of RNA", *Nucleic Acids Research*, 26(9): 2150-2155 (1998).
Leproust, et al. "Synthesis of high-quality libraries of long (150mer) oligonucleotides by a novel depurination controlled process", *Nucleic Acids Res.*, 38(8): 2522-2540 (2010). doi: 10.1093/nar/gkq163. Epub Mar. 22, 2010.
Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).

(56) References Cited

OTHER PUBLICATIONS

Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).

Li, et al. "An improved one-tube RT-PCR protocol for analyzing single-cell gene expression in individual mammalian cells", *Anal. Bioanal. Chem.*, 397: 1853-1859 (2010).

Li, et al. "β cell-specific CD4+T cell clonotypes in peripheral blood and the pancreatic islets are distinct", *J Immunol.*, 183(11): 7585-7591 (2009). doi: 10.4049/jimmunol.0901587. Epub Nov. 16, 2009.

Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).

Li, et al. "Detailed clonality analysis of relapsing precursor B acute lymphoblastic leukemia: implications for minimal residual disease detection", *Leukemia Research*, 25:1033-1045 (2001).

Li et al, "Mapping short DNA sequencing reads and calling variants using mapping quality scores," Genome Research, 18: 1851-1858 (2008).

Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).

Liedtke, et al. "A comparison of methods for RNA extraction from lymphocytes for RT-PCR", *PCR Methods and Applications*, 4(3): 185-187 (1994).

Lin, et al. "Multiplex genotype determination at a large number of gene loci", *Proc Natl Acad Sci USA*, 93(6): 2582-2587 (1996).

Liu, et al. "CD127 expression inversely correlates with FoxP3 and suppressive function of human CD4+T reg cells", *J Exp Med.*, 203(7): 1701-1711 (2006). Epub Jul. 3, 2006.

Lo, et al. "T cell immunodominance is dictated by the positively selecting self-peptide", Elife, 3:e01457 (2014). doi: 10.7554/eLife.01457. Epub Jan. 14, 2014.

Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).

Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.

Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).

Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.

Lovisa, et al. "IGH and IGK gene rearrangements as PCR targets for pediatric Burkitt's lymphoma and mature B-ALL MRD analysis", *Lab Invest.*, 89(10):1182-1186 (2009).

Lowe, T., et al., "A computer program for selection of oligonucleotide primers for polymerase chain reactions," *Nucleic Acids Research*, 18(7):1757-1761 (1990).

Lowman, et al. "Monovalent phage display: a method for selecting variant proteins from random libraries", *Methods: A Companion to Methods in Enzymology*, 3: 205-216, Abstract Only (1991).

Lúcio, P. et al. "Flow cytometric analysis of normal B cell differentiation: a frame of reference for the detection of minimal residual disease in precursor-B-ALL", *Leukemia*, 13:419-427 (1999).

Lyamichev, et al. "Polymorphism identification and quantitative detection of genomic DNA by invasive cleavage of oligonucleotide probes", *Nat Biotechnol.*, 17(3): 292-396 (1999).

Luo et al. "Analysis of the interindividual conservation of T cell receptor α- and β-chain variable regions gene in the peripheral blood of patients with systemic lupus erythematosus", *Clinical & Experimental Immunology*, 154(3):316-324 (2008).

Mackay, et al. "Real-time PCR in virology", *Nucleic Acids Res.*, 30(6): 1292-1305 (2002).

Mahmoud, S.M.A. et al. "Tumor-Infiltrating CD8+ Lymphocytes Predict Clinical Outcome in Breast Cancer", *Journal of Clinical Oncology*, 29(15): 1949-1955 (2011).

Maldonado, et al. "Intramuscular therapeutic vaccination targeting HPV16 induces T cell responses that localize in mucosal lesions", Sci Transl Med., 6(221): 221ra13 (2014). doi: 10.1126/scitranslmed.3007323.

Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.

Manion et al., "Reducing Error in Next Generation Sequencing Data with NextGENe Software's Condensation Tool™", Mar. 2009, pp. 1-3.

Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.

Mar et al. "Inferring steady state single-cell gene expression distributions from analysis of mesoscopic samples", *Genome Biology*, 7(12): R119, 12 pages (2006).

Mardis. "Next-generation DNA sequencing methods", *Annu. Rev. Genomics Hum. Genet.*, 9:387-402 (2008). doi: 10.1146/annurev.genom.9.081307.164359.

Marelli-Berg, F.M., et al. "Memory T-cell trafficking: new directions for busy commuters", *Immunology*, 130:158-165 (2010).

Margulies, et al. "Genome sequencing in microfabricated high-density picolitre reactors", *Nature*, 437(7057):376-380 (2005). Epub Jul. 31, 2005.

Mariani, S. et al., "Comprehensive assessment of the TCRBV repertoire in small T-cell samples by means of an improved and convenient multiplex PCR method," *Experimental Hematology*, 37(6):728-738 (2009).

Markoulatos, P. et al., "Multiplex Polymerase Chain Reaction: A Practical Approach", *Journal of Clinical Laboratory Analysis*, 16:47-51 (2002).

Marrero, et al. "High-throughput sequencing of islet-infiltrating memory CD4+ T cells reveals a similar pattern of TCR Vβ usage in prediabetic and diabetic NOD mice", PLoS One, 8(10):e76546 (2013). doi: 10.1371/journal.pone.0076546. eCollection 2013.

Martin-Jimenez, et al. "Molecular characterization of heavy chain immunoglobulin gene rearrangements in Waldenströ's macroglobulinemia and IgM monoclonal gammopathy of undetermined significance", *Haematologica*, 92(5): 635-642 (2007).

Mary et al. "Analysis of gene expression at the single-cell level using microdroplet-based microfluidic technology", *Biomicrofluidics*, 5: 024109-1-024109-10 (2011).

Maryanski, J.L. et al., "A quantitative, single-cell PCR analysis of an antigen-specific TCR repertoire 8 selected during an in vivo CD8 response: direct evidence for a wide range of clone sizes with uniform tissue distribution", *Molecular Immunology*, 36:745-753 (1999).

Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).

Mato et al. "Correlation of clonal T cell expansion with disease activity in systemic lupus erythematosus", *Int Immunol.*, 9(4):547-554 (1997).

Matolcsy, et al. "Clonal evolution of B cells in transformation from low- to high-grade lymphoma", *Eur. J. Immunol.*,29(4):1253-1264 (1999).

Matsubara, et al. "Microchamber array based DNA quantification and specific sequence detection from a single copy via PCR in nanoliter volumes", *Biosens Bioelectron*, 20(8): 1482-1490, Abstract Only (2005).

Matsumoto et al. "CDR3 spectratyping analysis of the TCR repertoire in Myasthenia Gravis", *The Journal of Immunology*, 176:5100-5107 (2006).

(56) References Cited

OTHER PUBLICATIONS

Matsumoto et al. "Complementarity-determining region 3 spectratyping analysis of the TCR repertoire in multiple sclerosis", *The Journal of Immunology*, 170:4846-4853 (2003).

Mazor et al. "Antibody internalization studied using a novel IgG binding toxin fusion", *Journal of Immunological Methods*, 321: 41-59 (2007).

Mazumder, et al., "Detection of multiple myeloma cells in peripheral blood using high-throughput sequencing assay" *Blood*, vol. 120, No. 21, Abstract 321 (Conference Abstract), Entire Abstract (2012).

McCloskey et al. "Encoding PCR products with batch-stamps and barcodes," *Biochem. Genet.*, 45: 761-767 (2007).

McGoldrick, et al. "Cytomegalovirus-specific T cells are primed early after cord blood transplant but fail to control virus in vivo", *Blood*, 121(14): 2796-803 (2013). doi: 10.1182/blood-2012-09-453720. Epub Feb. 14, 2013.

Mei et al. "Blood-borne human plasma cells in steady state are derived from mucosal immune responses", *Blood*, 113(11): 2461-2469 (2009).

Meijer et al. "Isolation of Human Antibody Repertoires with Preservation of the Natural Heavy and Light Chain Pairing", *J. Mol. Biol.*, 358: 764-772 (2006).

Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.

Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).

Meier, et al. "The influence of different stimulation conditions on the assessment of antigen-induced CD154 expression on CD4+T cells", *Cytometry A.*, (11):1035-1042 (2008). doi: 10.1002/cyto.a.20640.

Meleshko, et al. "Rearrangements of IgH, TCRD and TCRG genes as clonality marker of childhood acute lymphoblastic leukemia", *Experimental Oncology*, 27(4):319-324 (2005).

Menezes et al. "A public T cell clonotype within a heterogeneous autoreactive repertoire is dominant in driving EAE", *J Clin Invest*, 117(8):2176-2185 (2007).

Merriam-Webster, 2 pages, (definition of "e.g.," accessed Apr. 25, 2014).

Merriam-Webster, 4 pages (definition of "substantial," accessed Apr. 25, 2014).

Metzker, "Sequencing Technologies—The Next Generation", *Nature Reviews, Genetics*, 11:31-46 (2010).

Meyer et al. "Targeted high-throughput sequencing of tagged nucleic acid samples", *Nucleic Acids Research*, 35(15): e97, 5 pages (2007).

Miceli and Parnes. "The roles of CD4 and CD8 in T cell activation", *Seminars in Immunology*, 3(3): 133-141 (1991). Abstract only.

Michálek, et al. "Detection and long-term in vivo monitoring of individual tumor-specific T cell clones in patients with metastatic melanoma", *J Immunol.*, 178(11):6789-6795 (2007).

Michálek, et al. "Identification and monitoring of graft-versus-host specific T-cell clone in stem cell transplantation", *The Lancet*, 361(9364): 1183-1185 (2003).

Miller, et al., "Assembly algorithms for next-generation sequencing data", *Genomics*, 95(6): 315-327 (2010).

Miltenyi, et al. "High gradient magnetic cell separation with MACS", *Cytometry*, 11(2): 231-238 (1990).

Miner et al. "Molecular barcodes detect redundancy and contamination in hairpin-bisulfite PCR", *Nucleic Acids Research*, 32(17): e135, 4 pages (2004).

Miqueu, P. et al. "Statistical analysis of CDR3 length distributions for the assessment of T and B cell repertoire biases", *Molecular Immunology*, 44:1057-1064 (2007).

Mitra, et al. "Fluorescent in situ sequencing on polymerase colonies", *Anal Biochem.*, 320(1): 55-65, Abstract Only (2003).

Mittelstadl, et al. "Thymocyte responsiveness to endogenous glucocorticoids is required for immunological fitness", *J Clin Invest.*, 122(7):2384-94 (2012). doi: 10.1172/JCI63067. Epub Jun. 1, 2002.

Miyashita, et al. "N-Methyl substituted 2',4'-BNANC: a highly nuclease-resistant nucleic acid analogue with high-affinity RNA selective hybridization", *Chem Commun* (Camb), (36): 3765-3767, Abstract Only (2007). Epub Jul. 9, 2007.

Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).

Molloy, et al. "Soluble T cell receptors: novel immunotherapies", *Curr Opin Pharmacol.*, 5(4): 438-443 (2005) (Abstract Only).

Monod, M.Y. et al. "IMGT/JunctionAnalysis: the first tool for the analysis of the immunoglobulin and T cell receptor complex V-J and V-D-J JUNCTIONs", *Bioinformatics*, 20(Suppl 1):i379-385 (2004).

Moody, et al. "Antigen-specific B cell detection reagents: use and quality control", *Cytometry A.*, 73(11): 1086-1092 (2008). doi: 10.1002/cyto.a.20599.

Morgan, et al. "Cancer regression in patients after transfer of genetically engineered lymphocytes", *Science*, 314(5796): 126-129 (2006). Epub Aug. 31, 2006.

Morozova et al. "Applications of New Sequencing Technologies for Transcriptome Analysis", *Annu. Rev. Genomics Hum. Genet.*, 10: 135-151 (2009).

Morris, H., et al., "Tracking donor-reactive T cells: Evidence for clonal deletion in tolerant kidney transplant patients." Sci Transl Med. (2015); 7(272): 272ra10.

Morrissy et al. "Next-generation tag sequencing for cancer gene expression profiling", *Genome Research*, 19: 1825-1835 (2009).

Moss, et al. "The human T cell receptor in health and disease", *Annu. Rev. Immunol.*, 10:71-96 (1992).

Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.

Mueller, et al. "Human Treg responses allow sustained recombinant adeno-associated virus-mediated transgene expression", J Clin Invest., 123(12): 5310-5318 (2013). doi: 10.1172/JCI70314. Epub Nov. 15, 2013.

Muraro et al. "Molecular tracking of antigen-specific T cell clones in neurological immune-mediated disorders", *Brain*, 126(Pt 1):20-31 (2003).

Muraro, et al. "T cell repertoire following autologous stem cell transplantation for multiple sclerosis", J Clin Invest., 124(3): 1168-1172 (2014). doi: 10.1172/JCI71691. Epub Feb. 17, 2014.

Murugan, et al. "Statistical inference of the generation probability of T-cell receptors from sequence repertoires", *PNAS*, 109(40):16161-16166 (2012). doi: 10.1073/pnas.1212755109. Epub Sep. 17, 2012.

Naito, et al. "CD8+T cells infiltrated within cancer cell nests as a prognostic factor in human colorectal cancer", *Cancer Research*, 58(16): 3491-3494 (1998).

Nakano, et al. "Single-molecule PCR using water-in-oil emulsion", *J Biotechnol.*, 102(2): 117-124, Abstract Only (2003).

Nardi, et al. "Quantitative monitoring by polymerase colony assay of known mutations resistant to ABL kinase inhibitors", *Oncogene*, 27(6):775-782 (2008). Epub Aug. 6, 2007, 1-8.

Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov. 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Neller, et al. "High frequency of herpesvirus-specific clonotypes in the human T cell repertoire can remain stable over decades with minimal turnover", J Virol., 87(1): 697-700 (2013). doi: 10.1128/NI.02180-12. Epub Oct. 17, 2012.

(56) References Cited

OTHER PUBLICATIONS

Nelson. "CD20+ B cells: the other tumor-infiltrating lymphocytes", *The Journal of Immunology*, 185(9): 4977-4982 (2010). doi: 10.4049/jimmunol.1001323.

Newman, et al. "Identification of an antigen-specific B cell population", *J Immunol Methods*, 272(1-2): 177-187, Abstract Only (2003).

Nguyen et al. "Identification of errors introduced during high throughput sequencing of the T cell receptor repertoire" *BMC Genomics*, 12: 106, 13 pages (2011).

Nicot, N. et al. "Housekeeping gene selection for real-time RT-PCR normalization in potato during biotic and abiotic stress", *Journal of Experimental Botany*, 56(421):2907-2914 (2005).

Nie, et al. "Optical detection of single molecules", *Annu. Rev. Biophys. Biomol. Struct.*, 26: 567-596 (1997).

Nielsen, et al. "Peptide nucleic acid (PNA). A DNA mimic with a pseudopeptide backbone", *Chem. Soc. Rev.*, 26:73-78, Abstract Only (1997).

Nolan, T. et al. "Quantification of mRNA using real-time RT-PCR", *Nature Protocols*, 1(3):1559-1582 (2006).

Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Nucleis product webpage, "Exonuclease I-Shrimp alkaline phosphatase clean up of PCR products," (Published on webpage 2013) Downloaded Dec. 15, 2015.

Oble, et al. "Focus on TILs: prognostic significance of tumor infiltrating lymphocytes in human melanoma", *Cancer Immunity*, 9: 3, 20 pages (2009).

O'Brian et al., "Sorting out mix-ups. The provenance of tissue sections may be confirmed by PCR using microsatellite markers", *Am. J. Clin. Pathol.*, 106(6): 758-764 (1996). (Abstract Only).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ogle, et al. "Direct measurement of lymphocyte receptor diversity", *Nucleic Acids Research*, 31(22):e139, 6 pages (2003).

Ohtani. "Focus on TILs: prognostic significance of tumor infiltrating lymphocytes in human colorectal cancer", *Cancer Immunity*, 7: 4, 9 pages (2007).

Okajima et al. "Analysis of T cell receptor Vβ diversity in peripheral CD4+ and CD8+ T lymphocytes in patients with autoimmune thyroid diseases", *Clinical & Experimental Immunology*, 155:166-172 (2008).

Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.

Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

Packer and Muraro. "Optimized clonotypic analysis of T-cell receptor repertoire in immune reconstitution", *Experimental Hematology*, 35(3):516-521 (2007).

Pagès, Franck. Tumor-associated immune parameters for personalized patient care. Sci Transl Med., 5(214):214fs42 (2013). doi: 10.1126/scitranslmed.3007942.

Palmowski, et al. "The use of HLA class I tetramers to design a vaccination strategy for melanoma patients", *Immunol Rev.*, 188: 155-163 (2002) (Abstract Only).

Palomaki, et al. "DNA sequencing of maternal plasma reliably identifies trisomy 18 and trisomy 13 as well as Down syndrome: an international collaborative study", *Genet Med.*, 14(3): 296-305 (2012). doi: 10.1038/gim.2011.73. Epub Feb. 2, 2012.

Pan, et al. "A new FACS approach isolates hESC derived endoderm using transcription factors", *PLoS One*, 6(3): e17536, 9 pages (2011). doi: 10.1371/journal.pone.0017536.

Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).

Parameswaran et al. "A pyrosequencing-tailored nucleotide barcode design unveils opportunities for large-scale sample multiplexing", *Nucleic Acids Research*, 35(19): e130, 9 pages (2007).

Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.

Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.

Paszkiewicz et al, "De novo assembly of short sequence reads," *Briefings in Bioinformatics*, 11(5): 457-472 (2010).

Payne, et al. "Peripheral blood mononuclear cells of patients with breast cancer can be reprogrammed to enhance anti-HER-2/neu reactivity and overcome myeloid-derived suppressor cells", Breast Cancer Res Treat., 142(1):45-57 (2013). doi: 10.1007/s10549-013-2733-5. Epub Oct. 25, 2013.

Peet. "The Measurement of Species Diversity", *Annual Review of Ecology and Systematics*, 5: 285-307, Abstract Only (1974).

Petrosino, et al. "Metagenomic pyrosequencing and microbial identification", *Clin Chem.*, 55(5): 856-866 (2009). doi: 10.1373/clinchem.2008.107565. Epub Mar. 5, 2009.

PCT/US2009/006053, International Search Report dated Jun. 15, 2010, 6 pages.

PCT/US2009/006053, Written Opinion dated Jun. 15, 2010, 4 pages.

PCT/US2009/006053, International Preliminary Report on Patentability dated May 10, 2011, 5 pages.

PCT/US2010/037477, International Search Report and Written Opinion dated Sep. 24, 2010, 10 pages.

PCT/US2010/037477, International Preliminary Report on Patentability dated Jan. 4, 2012, 7 pages.

PCT/US2011/000791, International Search Report and Written Opinion dated Sep. 22, 2011, 13 pages.

PCT/US2011/000791, International Preliminary Report on Patentability dated Nov. 6, 2012, 10 pages.

PCT/US2011/049012, International Search Report and Written Opinion dated Apr. 10, 2012, 9 pages.

PCT/US2011/049012, International Preliminary Report on Patentability dated Feb. 26, 2013, 5 pages.

PCT/US2015/010904, International Search Report dated May 6, 2015, 4 pages.

PCT/US2015/010904, Written Opinion dated May 6, 2015, 4 pages.

PCT/US2015/010904, International Preliminary Report on Patentability dated Jul. 12, 2016, 14 pages.

PCT/US2012/053530, International Preliminary Report on Patentability dated Mar. 12, 2014, 7 pages.

PCT/US2012/053530, International Search Report and Written Opinion dated Feb. 26, 2013, 13 pages.

PCT/US2012/058989, International Preliminary Report on Patentability dated Apr. 15, 2014, 8 pages.

PCT/US2012/058989, International Search Report and Written Opinion dated Mar. 29, 2013, 12 pages.

PCT/US2012/068631, International Preliminary Report on Patentability dated Jun. 10, 2014, 7 pages.

PCT/US2012/068631, International Search Report and Written Opinion dated Feb. 26, 2013, 8 pages.

PCT/US2012/069187, International Preliminary Report on Patentability dated May 5, 2015, 6 pages.

PCT/US2012/069187, International Search Report and Written Opinion dated Feb. 22, 2013, 8 pages.

PCT/US2013/029181, International Search Report and Written Opinion dated May 31, 2013, 6 pages.

PCT/US2013/029181, International Preliminary Report on Patentability dated Sep. 9, 2014, 5 pages.

(56) References Cited

OTHER PUBLICATIONS

PCT/US2013/062925, International Preliminary Report on Patentability dated Apr. 16, 2015, 30 pages.
PCT/US2013/062925, International Search Report and Written Opinion dated Nov. 25, 2013, 11 pages.
PCT/US2013/062925, Second Written Opinion dated Jan. 23, 2015, 7 pages.
PCT/US2014/047909, International Preliminary Report on Patentability dated Jan. 26, 2016.
PCT/US2014/047909, International Search Report dated Nov. 17, 2014.
PCT/US2014/047909, Written Opinion dated Nov. 17, 2014, 9 pages.
PCT/US2015/062494, International Search Report and Written Opinion dated Mar. 31, 2016, 29 pages.
PCT/US2015/062494, International Preliminary Report on Patentability, dated May 30, 2017, 22 pages.
Pekin, D. et al. "Quantitative and sensitive detection of rare mutations using droplet-based microfluidics", Lab Chip, 11(3): 2156-2166 (2011).
Pels et al. "Clonal evolution as pathogenetic mechanism in relapse of primary CNS lymphoma", Neurology, 63(1):167-169 (2004).
Perkel, J. "Overcoming the Challenges of Multiplex PCR", Biocompare Editorial Article, Oct. 23, 2012, 6 Pages, can be retrieved at URL:http://www.biocompare.com/Editorial-Articles/117895-Multiplex-PCR/>.
Pira et al. "Human naive CD4 T-cell clones specific for HIV envelope persist for years in vivo in the absence of antigenic challenge", J Acquir Immune Defic Syndr., 40(2):132-139 (2005).
Plasilova et al. "Application of the Molecular Analysis of the T-Cell Receptor Repertoire in the Study of Immune-Mediated Hematologic Diseases", Hematology, 8(3): 173-181 (2003).
Pohl, G. and Shih. "Principle and applications of digital PCR", Expert Rev. Mol. Diagn., 4(1):41-47 (2004).
Polstra, et al. "Development of real-time NASBA assays with molecular beacon detection to quantify mRNA coding for HHV-8 lytic and latent genes", BMC Infect Dis., 2: 18 (2002). Epub Sep. 4, 2002.
Pop and Salzberg. "Bioinformatics challenges of new sequencing technology", NIH, Trends Genet., 24(3): 142-149 (2008).
Pourmand, et al. "Direct electrical detection of DNA synthesis", PNAS, 103(17): 6466-6470 (2006). Epub Apr. 13, 2006.
Polz and Cavanaugh. "Bias in Template-to-Product Ratios in Multitemplate PCR", Applied and Environmental Microbiology, 64(10): 3724-3730 (1998).
Porter, et al. "Chimeric antigen receptor-modified T cells in chronic lymphoid leukemia", N Engl J Med., 365(8):725-33 (2011). doi: 10.1056/NEJMoa1103849. Epub Aug. 10, 2011.
Prabakaran et al. "454 antibody sequencing—error characterization and correction", BMC Research Notes, 4: 404 (2011).
Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant., 13(11): 3010-3020 (2013). doi: 10.1111/ajt.12433. EpubSep. 18, 2013.
Qiu et al. "DNA sequence-based "bar codes" for tracking the origins of expressed sequence tags from a maize cDNA library constructed using multiple mRNA sources", Plant Physiology, 133(2): 475-481 (2003).
Qu et al. "Efficient frequency-based de novo short-read clustering for error trimming in next-generation sequencing", Genome Research, 19: 1309-1315 (2009).
Quick. SOLiD System—a next-gen DNA sequencing platform announced, Gizmag online magazine, http://www.mizmag.com/go/ 8248, pp. 1-5, Oct. 2007.
Quince et al. "Removing Noise From Pyrosequenced Amplicons", BMC Informatics, 12: 38 (2011).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", Semin Cancer Biol., 20(4): 254-260 (2010). doi: 10.1016/j.semcancer.2010. 06.002. Epub Jul. 1, 2010.
Rao, Sridhar, "B cell activation and Humoral Immunity", Jan. 22, 2009 (Jan. 22, 2009), pp. 1-9, XP055192552, Retrieved from the Internet: URL:http://www.microrao.com/micronotes/pg/humoral_immunity.pdf [retrieved on Jun. 1, 2015].
Rasmussen, T. et al. "Quantitation of minimal residual disease in multiple myeloma using an allele-specific real-time PCR assay", Experimental Hematology, 28:1039-1045 (2000).
Ray, et al. "Single cell multiplex PCR amplification of five dystrophin gene exons combined with gender determination", Molecular Human Reproduction, 7(5): 489-494 (2001).
Reddy, et al. "Monoclonal antibodies isolated without screening by analyzing the variable-gene repertoire of plasma cells", Nature Biotechnology, 28(9): 965-969 (2010). doi: 10.1038/nbt.1673. Epub Aug. 29, 2010.
Reddy and Georgiou. "Systems analysis of adaptive immunity by utilization of high-throughput technologies", Current Opinion in Biotechnology, 22(4): 584-589 (2011).
Reinartz et al. "Massively parallel signature sequencing (MPSS) as a tool for in-depth quantitative gene expression profiling in all organisms", Brief Funct Genomic Proteomic., 1(1):95-104 (2002).
Reischl and Kochanowski. "Quantitative PCR. A Survey of the Present Technology", Molecular Biotechnology, 3:55-71 (1995).
Ria, et al. "Collagen-specific T-cell repertoire in blood and synovial fluid varies with disease activity in early rheumatoid arthritis", Arthritis Res Ther., 10(6):R135, 18 pages (2008). Epub Nov. 17, 2008.
Rickinson and Moss. "Human cytotoxic T lymphocyte responses to Epstein-Barr virus infection", Annu Rev Immunol., 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", Lancet, 364:355-364 (2004).
Robert, et al. "CTLA4 blockade broadens the peripheral T-cell receptor repertoire", Clin Cancer Res., 20(9):2424-32 (2014). doi: 10.1158/1078-0432.CCR-13-2648. Epub Feb. 28, 2014.
Robins, H. et al. "Ultra-sensitive detection of rare T cell clones", Journal of Immunological Methods, 375(1-2): 14-19 (2012). Epub Sep. 10, 2011.
Robins, et al. "CD4+ and CD8+T cell β antigen receptors have different and predictable V and J gene usage and CDR3 lengths", J. Immunol., 188: 115.10, Abstract (2012).
Robins et al. "Detecting and monitoring lymphoma with high-throughput sequencing" Oncotarget, 2:287-288 (2011).
Robins, H. et al. "Digital Genomic Quantification of Tumor Infiltrating Lymphocytes", Science Translational Medicine, 5:214ra169, 19 pages, Supplementary Materials (2013).
Robins, H. et al. "Comprehensive assessment of T-cell receptor β-chain diversity in αβ T cells", Blood, 114(19):4099-4107 (and Supplemental Materials) (2009).
Robins, et al. "Effects of aging on the human adaptive immune system revealed by high-throughput DNA sequencing of T cell receptors", J Immunol., 188: 47.16, Abstract (2012).
Robins, et al. "High-throughput sequencing of T-cell receptors." Sep. 2010. Poster. 1 page.
Robins, et al. "Immune profiling with high-throughput sequencing." Presented for the ASHI 2011 conference. Oct. 2011. Poster. 1 page.

(56) References Cited

OTHER PUBLICATIONS

Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.
Robins, H. et al. "Overlap and Effective Size of the Human CD8+T Cell Receptor Repertoire", *Science Transitional Medicine*, 2(47, 47ra64):17 pages, Supplemental Materials (2010).
Robins, et al. "Overlap of the human CD8+ T cell receptor repertoire." Oct. 2010. Poster. 1 page.
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Robins, H. et al. "The Computational Detection of Functional Nucleotide Sequence Motifs in the Coding Regions of Organisms", *Exp Biol Med*, 233(6): 665-673 (2008).
Rock, E.P. et al. "CDR3 Length in Antigen-specific Immune Receptors", *J. Exp. Med.*, 179:323-328 (1994).
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Roshal, M. et al. "Immaturity Associated Antigens Are Lost During Induction for T Cell Lymphoblastic Leukemia: Implications for Minimal Residual Disease Detection", *Cytometry Part B (Clinical Cytometry)*, 78:139-146 (2010).
Rothberg, et al. "An integrated semiconductor device enabling non-optical genome sequencing", *Nature*, 475(7356): 348-352 (2011). doi: 10.1038/nature10242.
Rothberg et al. "The development and impact of 454 sequencing", *Nature Biotechnology*, 26(10): 1117-1124 (2008).
Rougemont, et al. "Probabilistic base calling of Solexa sequencing data", *BMC Bioinformatics*, 9:431, 12 pages (2008).
Rozen, S. et al. "Primer3 on the WWW for General Users and for Biologist Programmers", *Methods in Molecular Biology, Bioinformatics Methods and Protocols*, 132:365-386 (2000).
Ryan et al. "Clonal evolution of lymphoblastoid cell lines", *Laboratory Investigation*, 86(11):1193-1200 (2006). Epub Oct. 2, 2006.
Saada, R. et al. "Models for antigen receptor gene rearrangement: CDR3 length", *Immunology and Cell Biology*, 85:323-332 (2007).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santalucia, Jr., J. "Physical Principles and Visual-OMP Software for Optimal PCR Design," *Methods in Molecular Biology*, 402(PCR Primer Design):3-33, 40 pages (2007).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sartorius Stedim Biotech product brochure, "Primer removal after a PCR reaction with Vivacon® 2", (2010).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).
Schlissel, M.S. et al. "Leukemia and lymphoma: a cost of doing business for adaptive immunity", *Genes Dev.*, 20(12): 1539-1544 (2006).
Schloss, PD et al. Reducing the Effects of PCR Amplification and Sequencing Artifacts on 16S Rrna-Based Studies. PLoS One. Dec. 14, 2011, vol. 6, No. 12; e27310; DOI: 10.1371/journal.pone. 002731 0.
Schmitt et al. "Detection of ultra-rare mutations by next-generation sequencing," *PNAS*, 109(36): 14508-14513 and Supporting Information, 9 pages (2012).
Schøller et al. "Analysis of T cell receptor αβ variability in lymphocytes infiltrating melanoma primary tumours and metastatic lesions", *Cancer Immunol Immunother.* 39(4):239-248 (1994).
Schrappe, M. et al. "Late MRD response determines relapse risk overall and in subsets of childhood T-cell ALL: results of the AIEOP-BFM-ALL 2000 study", *Blood*, 118(8): 2077-2084 (2011).
Schreiber et al. "Cancer immunoediting: integrating immunity's roles in cancer suppression and promotion", *Science*, 331(6024): 1565-1570 (2011). doi: 10.1126/science.1203486.
Schwab et al. "CD8+ T-cell clones dominate brain infiltrates in Rasmussen encephalitis and persist in the periphery", *Brain*, 132:1236-1246 (2009).
Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.
Chinese Patent Application No. 201510054401.X, Search Report dated Jul. 14, 2016, 2 pages.
Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).
Sehouli et al. "Epigenetic quantification of tumor-infiltrating T-lymphocytes" *Epigenetics*, 6(2): 236-246 (2011). Epub Feb. 1, 2011.
Seitz, et al. "Reconstitution of paired T cell receptor α- and β-chains from microdissected single cells of human inflammatory tissues", *PNAS*, 103: 12057-12062 (2006).
Seo, et al. "Four-color DNA sequencing by synthesis on a chip using photocleavable fluorescent nucleotides", *PNAS*, 102(17): 5926-5931 (2005). Epub Apr. 13, 2005.
Sequenta and iRepertoire Join Forces on Blood Cancer Testing. Business Wire. Aug. 8, 2013. http://www.businesswire.com/news/home/20130808005363/en/SequentaiRepertoire-Join-Forces-Blo ...#. VGTT9W dOyUk. 2 pages.
Sfanos et al. "Human Prostate-Infiltrating CD8+ T Lymphocytes are Oligoclonal and PD-1", *The Prostate*, 69(15): 1694-1703 (2009).
Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.
Shen et al. "Comparing platforms for *C. elegans* mutant identification using high-throughput whole-genome sequencing", *PLoS One*, 3(12):e4012, 6 pages (2008).
Shendure, et al. "Accurate multiplex polony sequencing of an evolved bacterial genome", *Science*, 309(5741): 1728-1732, Abstract Only (2005). Epub Aug. 4, 2005.
Shendure, et al. "Advanced sequencing technologies: methods and goals", *Nat Rev Genet.*, 5(5): 335-344 (2004).
Shendure and Ji. "Next-generation DNA sequencing", *Nature Biotechnology*, 26(10):1135-1145 (2008).
Sherwood, A. et al. "Deep Sequencing of the Human TCRγ and TCRβ Repertoires Suggests that TCR β Rearranges After αβ and γδT Cell Commitment", Science Translational Medicine, *Sci. Transl. Med.*, 3(90): 1-7 (2011).
Sherwood, et al. "New Technologies for Measurements of Tumor Infiltrating Lymphocytes", Presented Nov. 7, 2012 Moscone Center, Exhibit Halls ABC.

(56) References Cited

OTHER PUBLICATIONS

Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.

Shino, et al. "Usefulness of immune monitoring in lung transplantation using adenosine triphosphate production in activated lymphocytes", *The Journal of Heart and Lung Transplant*, 31: 996-1002 (2012).

Shiroguchi et al. "Digital RNA sequencing minimizes sequence-dependent bias and amplification noise with optimized single-molecule barcodes", *PNAS*, 109(4): 1347-1352 (2012).

Shoemaker et al. "Quantitative phenotypic analysis of yeast deletion mutants using a highly parallel molecular bar-coding strategy," *Nature Genetics*, 14(4): 450-456 (1996).

Shumaker, et al. "Mutation detection by solid phase primer extension", *Hum Mutat.*, 7(4): 346-354, Abstract Only (1996).

Sia, et al. "Microfluidic devices fabricated in poly(dimethylsiloxane) for biological studies", *Electrophoresis*, 24(21): 3563-3576, Abstract Only (2003).

Silver, N. et al. "Selection of housekeeping genes for gene expression studies in human reticulocytes using real-time PCR", *BMC Molecular Biology*, 7(33):1-9 (2006).

Sims, et al. "Fluorogenic DNA sequencing in PDMS microreactors", *Nat Methods*, 8(7): 575-580 (2011). doi: 10.1038/nmeth.1629.

Sims, et al. "MHC-peptide tetramers for the analysis of antigen-specific T cells", *Expert Rev Vaccines*, 9(7): 765-774 (2010). doi: 10.1586/erv.10.66.

Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", *Hepatology*, 33(5):1288-1298 (2001).

Sint, D., et al. "Advances in multiplex PCR: balancing primer efficiencies and improving detection success", *Methods in Ecology and Evolution*, 3(5): 898-905 (2012).

Skulina et al. "Multiple Sclerosis: Brain-infiltrating CD8+ T cells persist as clonal expansions in the cerebrospinal fluid and blood", *PNAS*, 101(8):2428-2433 (2004).

Slightom, J.L. et al. "*Homo sapiens* germline beta T-cell receptor locus", NCBI Accession No. L36092 NCBI, 254 pages (2009) Retrieved from the Internet: <URL:http://www.ncbi.nlm.nih.gov/nuccore/L36092>.

Smith, et al. "Comparison of biosequences", *Advances in Applied Mathematics*, 2: 482-489 (1981).

Smith et al. "Rapid generation of fully human monoclonal antibodies specific to a vaccinating antigen", *Nature Protocols*, 4(3): 372-384 and Corrigenda (2009).

Smith et al. "Rapid whole-genome mutational profiling using next-generation sequencing technologies", *Genome Research*, 18: 1638-1642 (2008).

Smith et al. "Quantitative phenotyping via deep barcode sequencing", *Genome Research*, 19: 18361842 (2009).

Smith et al, "Using quality scores and longer reads improves accuracy of Solexa read mapping," *BMC Bioinformatics*, 9: 128 (2008).

Sobrino, et al. "SNPs in forensic genetics: a review on SNP typing methodologies", *Forensic Sci Int.*, 154(2-3): 181-194, Abstract Only (2005). Epub Jan. 11, 2005.

Speiser et al., "A novel approach to characterize clonality and differentiation of human melanoma-specific T cell responses: spontaneous priming and efficient boosting by vaccination." The Journal of Immunology, 177(2): 1338-1348 (2006).

Spreafico, et al. "A circulating reservoir of pathogenic-like CD4+T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].

Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).

Srinivasan et al. "Effect of fixatives and tissue processing on the content and integrity of nucleic acids", *Am J Pathol.*, 161(6): 1961-1971 (2002).

Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.

Standard Sequencing Primers, Max Planck Genome Center Cologne, Jan. 15, 2011, 2 pages, downloaded from https://genomecentre.mpipz.mpg.de/SeqOrderDB/export/sequencing-primers.html.

Stanley. Essentials of Immunology & Serology, Delmar, Thomson Learning, Chapter 7, T cells, p. 95 (2002).

Steenbergen, et al. "Distinct ongoing Ig heavy chain rearrangement processes in childhood B-precursor acute lymphoblastic leukemia", *Blood*, 82(2):581-589 (1993).

Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).

Stein and Nombela-Arrieta. "Chemokine control of lymphocyte trafficking: a general overview", *Immunology*, 116(10):1-12 (2005).

Steinmetz, O.M. et al. "Chemokines and B cells in renal inflammation and allograft rejection", *Frontiers in Bioscience (Schol. Ed.)*, 1:13-22 (2009).

Stemmer, et al. "Single-step assembly of a gene and entire plasmid from large number of oligodeoxyribonucleotides", *Gene*, 164(1): 49-53 (1995).

Steward et al. "A polymerase chain reaction study of the stability of Ig heavy-chain and T-cell receptor delta gene rearrangements between presentation and relapse of childhood B-lineage acute lymphoblastic leukemia", *Blood*, 83(5):1355-1362 (1994).

Stewart and Schwartz. "Immunoglobulin V regions and the B cell", *Blood*, 83(7): 1717-1730 (1994).

Stickler, et al. "An in vitro human cell-based assay to rank the relative immunogenicity of proteins", *Toxicol Sci.*, 77(2): 280-289 (2004). Epub Dec. 22, 2003.

Stiller et al. "Direct multiplex sequencing (DMPS)—a novel method for targeted high-throughput sequencing of ancient and highly degraded DNA", *Genome Research*, 19: 1843-849 (2009).

Straten, Per thor, et al. "T-cell clonotypes in cancer", *Journal of Translational Medicine*, 2(1): 11, 10 pages (2004).

Stratton. "Exploring the genomes of cancer cells: progress and promise", *Science*, 331(6024): 1553-1558 (2011). doi: 10.1126/science.1204040.

Striebich, et al. "Selective Accumulation of Related CD41 T Cell Clones in the Synovial Fluid of Patients with Rheumatoid Arthritis", *J Immunol.*, 161(8): 4428-4436 (1998).

Struyk et al. "T cell receptors in rheumatoid arthritis", *Arthritis & Rheumatism*, 38(5):577-589 (1995).

Sumida et al. "T cell receptor repertoire of infiltrating T cells in lips of Sjögren's syndrome patients", *J Clin Invest.*, 89:681-685 (1992).

Sumida et al. "T cell receptor Vα repertoire of infiltrating T cells in labial salivary glands from patients with Sjögren's syndrome", *J Rheumatol.*, 21:1655-1661 (1994).

Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.

Szczepanski et al. "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).

Szczepanski, T. et al. "Minimal residual disease in leukemia patients", *Lancet Oncology*, 2:409-417 (2001).

Szczepanski et al. "Why and how to quantify minimal residual disease in acute lymphoblastic leukemia?", *Leukemia*, 21(4):622-626 (2007). Epub Feb. 15, 2007.

(56) References Cited

OTHER PUBLICATIONS

Tackenberg et al. "Clonal expansions of CD4+ β helper T cells in autoimmune myasthenia gravis", *European Journal of Immunology*, 37(3):849-863 (2007).
Tajiri et al. "Cell-microarray analysis of antigen-specific B-cells: single cell analysis of antigen receptor expression and specificity", *Cytometry Part A*, 71A: 961-967 (2007).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion Is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
Taylor et al., "Intraclonal homogeneity of clonotypic immunoglobulin M and diversity of nonclinical post-switch isotypes in multiple myeloma: insights into the evolution of the myeloma clone", *Clin Cancer Res.*, 8(2): 502-513 (2002).
Ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Corrigendum: Microdroplet-based PCR enrichment for large-scale targeted sequencing", *Nature Biotechnology*, 28(2):178, 1 page (2010).
Tewhey, R. et al. "Microdroplet-based PCR enrichment for large-scale targeted sequencing," *Nature Biotechnology*, 27(11):1025-1031 (2009).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes A γ Protein Expressed on the Majority of CD3+ T Cell Receptor-α/fr Circulating Lymphocytes", *J. Exp. Med.*, 167:694-699 (1988).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated Jun. 29, 2012 for UK application No. GB1209668.1.
UK Combined Search Report and Office action dated May 27, 2011 for UK application No. GB1105068.9.
UK Search Report and office action dated Jan. 13, 2012 for UK application No. GB1120209.0.
UK Search Report and office action dated Jul. 7, 2010 for UK application No. GB1009641.0.

Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Urquhart, et al. "Rate-controlled delivery systems in drug and hormone research", *Annu Rev Pharmacol Toxicol.*, 24: 199-236, Abstract Only (1984).
Van Der Velden, V.H.J., et al. "Analysis of minimal residual disease by Ig/TCR gene rearrangements: guidelines for interpretation of real-time quantitative PCR data," *Leukemia*, 21:604-611 (2007).
Van Der Velden, V.H.J., et al. "Detection of minimal residual disease in hematologic malignancies by realtime quantitative PCR: principles, approaches, and laboratory aspects," *Leukemia*, 17:1013-1034 (2003).
Van Der Velden, V.H.J., et al. "Optimization of PCR-based minimal residual disease diagnostics for childhood acute lymphoblastic leukemia in a multi-center setting," *Leukemia*, 21:706-713 (2007).
Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al. "Design and standardization of PCR primers and protocols for detection of clonal immunoglobulin and I-cell receptor gene recombinations in suspect lymphoproliferations: Report of the BIOMED-2 Concerted Action BMHC-C198-3936", *Leukemia*, 17:2257-2317 (2003).
Van Dongen, J.J.M. et al. "Prognostic value of minimal residual disease in acute lymphoblastic leukaemia in childhood", *The Lancet*, 352:1731-1738 (1998).
Vanderborght, et al. "Dynamic T cell receptor clonotype changes in synovial tissue of patients with early rheumatoid arthritis: effects of treatment with cyclosporin A (Neoral)", *J Rheumatol.*, 29(3): 416-426 (2002).
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8+T Cell Responses to Cytomegalovirus and EBV[1]", *The Journal of Immunology*, 181:7853-7862 (2008).
Venturi, V. et al. "The molecular basis for public T-cell responses?", *Nature Reviews*, 8:231-238 (2008).
Verhagen, O.J.H.M., et al. "Application of germline IGH probes in real-time quantitative PCR for the detection of minimal residual disease in acute lymphoblastic leukemia", *Leukemia*, 14:1426-1435 (2000).
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).
Vogelstein et al. "Cancer genome landscapes", *Science*, 339(6127): 1546-1558 (2013). doi: 10.1126/science.1235122.
Vogelstein and Kinzler. "Digital PCR," *Genetics, PNAS*, 96:9236-9241 (1999).
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.
Wang, et al. "Balanced-PCR amplification allows unbiased identification of genomic copy changes in minute cell and tissue samples", *Nucleic Acids Research*, 32(9): e76, 10 pages (2004).

(56) References Cited

OTHER PUBLICATIONS

Wang, et al. "High throughput sequencing reveals a complex pattern of dynamic interrelationships among human T cell subsets", *PNAS*, 107(4): 1518-1528 (2010).
Wang, et al. "HIV integration site selection: Analysis by massively parallel pyrosequencing reveals association with epigenetic modifications", *Genome Research*, 17(8): 1186-1194 (2007). EpubJun. 1, 2007.
Wang et al. "Immunorepertoire analysis by multiplex PCR amplification and high throughput sequencing", Poster—Program 42.6, The 96th Annual Meeting of the America Association of Immunologists, Seattle, USA, May 8-12, 2009, 1 page.
Wang, X. et al. "Quantitative Measurement of Pathogen Specific Human Memory T Cell Repertoire Diversity using a CDR3 B-Specific Microarray", *BMC Genomics*, 8(329): 1-13 (2007).
Ward and Marelli-Berg. "Mechanisms of chemokine and antigen-dependent T-lymphocyte navigation", *Biochem. J.*, 418:13-27 (2009).
Warren et al. "Exhaustive T-cell repertoire sequencing of human peripheral blood samples reveals signatures of antigen selection and a directly measured repertoire size of at least 1 million clonotypes", *Genome Res.*, 21(5): 790-797 (2011). Epub Feb. 24, 2011.
Warren et al. "Profiling model T-cell metagenomes with short reads", *Bioinformatics*, 25(4):458-464 (2009).
Weinstein, J.A. et al. "High-Throughput Sequencing of the Zebrafish Antibody Repertoire", *Science*, 324(5928): 807-810 (2009).
Weinstein, J.A. et al. "High-Throughput Sequencing of the Zebrafish Antibody Repertoire", *Science*, 324(5928): 807-810, Supporting/ Supplementary Materials (2009).
Weiss et al. "Clonal Rearrangements of T-Cell Receptor Genes in Mycosis Fungoides and Dermatopathic Lymphadenopathy", *The New England Journal of Medicine*, 313(9):539-544 (1985).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).
Wells, et al. "Strategies for preimplantation genetic diagnosis of single gene disorders by DNA amplification", *Prenatal Diagnosis*, 18(13):1389-1401 (1998).
Weng, et al. "Minimal residual disease monitoring with high-throughput sequencing of T cell receptors in cutaneous T cell lymphoma", Sci Transl Med., 5(214):214ra171 (2013). doi: 10.1126/scitranslmed.3007420.
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).
Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneo detection using molecular beacons", *Nucleic Acids Res.*, 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Williams, et al. "Amplification of complex gene libraries by emulsion PCR", *Nat Methods*, 3(7): 545-550 (2006).
Wlodarski et al. "Molecular strategies for detection and quantitation of clonal cytotoxic T-cell responses in aplastic anemia and myelodysplastic syndrome", *Blood*, 108(8):2632-2641 (2006).
Wlodarski et al. "Pathologic clonal cytotoxic T-cell responses: nonrandom nature of the T-cell-receptor restriction in large granular lymphocyte leukemia", *Blood*, 106:2769-2779 (2005).
Wolda. "Similarity Indices, Sample Size and Diversity", *Oecologia* (Berl), 50:296-302 (1981).
Wolfl, et al. "Activation-induced expression of CD137 permits detection, isolation, and expansion of the full repertoire of CD8+T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+T cells without the need to know epitope specificities", *Cytometry A.*, 73(11): 1043-1049 (2008). doi: 10.1002/cyto.a.20594.
Wood, B. "9-Color and 10-Color Flow Cytometry in the Clinical Laboratory", *Arch Pathol Lab Med*, 130:680-690 (2006).
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Wrammert et al. "Rapid cloning of high-affinity human monoclonal antibodies against influenza virus", *Nature*, 453: 667-672 (2008).
Wu, et al. "High-throughput sequencing detects minimal residual disease in acute T lymphoblastic leukemia", Sci Transl Med., 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, Y-C. et al. "High-throughput immunoglobulin repertoire analysis distinguishes between human IgM memory and switched memory B-cell populations", *Blood Journal*, 116(7): 1070-1078, 22 pages (2010).
Wu et al. "Focused Evolution of HIV-1 Neutralizing Antibodies Revealed by Structures and Deep Sequencing", *Science*, 333: 1593-1602 (2011).
Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Xiong, et al. "Chemical gene synthesis: strategies, softwares, error corrections, and applications", *FEMS Microbiol Rev.*, 32(3): 522-540 (2008). doi: 10.1111/j.1574-6976.2008.00109.x. Epub Apr. 2, 2008.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, W. et al. "A Novel Universal Primer-Multiplex-PCR Method with Sequencing Gel Electrophoresis Analysis", *PLoS One*, 7(1): e22900, 10 pages (2012).
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Yao, et al. "Analysis of the CDR3 length repertoire and the diversity of TCRα chain in human peripheral blood T Lymphocytes", Cell Mol Immunol., 4(3): 215-220 (2007).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yassai, M.B. et al. "A clonotype nomenclature for T cell receptors", *Immunogenetics*, 61:493-502 (2009).
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).
York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.
Yu and Fu. "Tumor-infiltrating T lymphocytes: friends or foes?", *Lab Invest.*, 86(3): 231-245 (2006).

(56) References Cited

OTHER PUBLICATIONS

Zagnoni, et al. "Droplet Microfluidics for High-throughput Analysis of Cells and Particles", *Methods in Cell Biology*, Chapter 2, 102: 23-48 (2011).
Zaliova, et al. "Quantification of fusion transcript reveals a subgroup with distinct biological properties and predicts relapse in BCR/ABL-positive ALL: implications for residual disease monitoring", *Leukemia*,23(5):944-951 (2009).
Zehentner et al. "Minimal Disease Detection and Confirmation in Hematologic Malignancies: Combining Cell Sorting with Clonality Profiling", *Clinical Chemistry*, 52(3): 430-437 (2006).
Zeng et al. "High-performance single cell genetic analysis using microfluidic emulsion generator arrays", *Anal. Chem.*, 82(8):3183-3190 (2010).
Zhang, Minying, et al. "A New Approach to Simultaneously Quantify Both TCR α- and β-Chain Diversity after Adoptive Immunotherapy." Clinical Cancer Research (2012); 18(17): 4733-4742.
Zhong, Q. et al. "Multiplex digital PCR: breaking the one target per color barrier of quantitative PCR", Lab Chip, 11:2167-2174 (2011).
Zhou et al. "High throughput analysis of TCR-β rearrangement and gene expression in single cells", *Laboratory Investigation*, 86: 314-321 (2006).
Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.
Zhu, et al. "Immune surveillance by CD8αα+ skin-resident T cells in human herpes virus infection", Nature, 497(7450):494-7 and Corrigendum (2013). doi: 10.1038/nature12110. Epub May 8, 2013.
Zimmerman and Mannhalter. "Technical aspects of quantitative competitive PCR", *Biotechniques*, 21: 268-279 (1996).
Födinger et al., "Multiplex PCR for rapid detection of T-cell receptor-gamma chain gene rearrangements in patients with lymphoproliferative diseases." British Journal of Haematology (1996); 94(1): 136-139.
Howie, et al., "High throughput pairing of T cell receptor α and β sequences." Science Translational Medicine (2015); 7(301): 301ra131, and supplementary materials, 19 pages.
Panzara, et al., "Analysis of the T cell repertoire using the PCR and specific oligonucleotide primers." Biotechniques (1992); 12(5): 728-735.
Sotomayor et al. "In vivo blockade of CTLA-4 enhances the priming of responsive T cells but fails to prevent the induction of tumor antigen-specific tolerance." Proceedings of the National Academy of Sciences, 96(20): 11476-11481 (1999).
Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.
DeWitt, et al., "Dynamics of the Cytotoxic T Cell Response to a Model of Acute Viral Infection." *J. Virol.* (2015); 89 (8): 4517-4526.
European Patent Application No. 15864123.3, Extended European Search Report dated Mar. 19, 2018, 8 pages.
European Patent Application No. 17199432.0, Extended European Search Report dated Feb. 14, 2018, 10 pages.
Sotomayor, et al., "Conversion of tumor-specific CD4+T-cell tolerance to T-cell priming through in vivo ligation of CD40." Nature Medicine (1999); 5(7): 780-787.
Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements." Am J Pathol. (2001); 158(5): 1851-1857.
Yagi, et al., "Detection of clonotypic IGH and TCR rearrangements in the neonatal blood spots of infants and children with B-cell precursor acute lymphoblastic leukemia." Blood (2000); 96(1): 264-268.

* cited by examiner

IMMUNOCOMPETENCE ASSESSMENT BY ADAPTIVE IMMUNE RECEPTOR DIVERSITY AND CLONALITY CHARACTERIZATION

CROSS REFERENCE TO RELATED APPLICATIONS

This application is a continuation of U.S. application Ser. No. 14/432,738, filed Mar. 31, 2015, which is a national stage filing under 35 U.S.C. 371 of International Patent Application No. PCT/US2013/062925, filed Oct. 1, 2013, which claims the benefit of U.S. Provisional Application No. 61/708,534, filed Oct. 1, 2012. The entire disclosure of each above-listed application is hereby incorporated by reference in its entirety for all purposes.

STATEMENT OF GOVERNMENT INTEREST

This invention was made with government support under Grant No. RHL106868A awarded by the National Heart, Blood and Lung Institute of the National Institutes of Health. The government has certain rights in this invention.

BACKGROUND

Technical Field

The present disclosure relates generally to assessment of immunocompetence of a subject's adaptive immune system by highly sensitive, high throughput DNA sequence-based quantification of the diversity and frequency of occurrence (e.g., clonal expansion) of adaptive immune cells having a particular rearranged T cell receptor (TCR) or immunoglobulin (IG or Ig) encoding gene sequence. Information about the immunological status of a subject or a population of subjects can be used, for example, to characterize an individual or to stratify a patient population with respect to ability to mount an immune response or likelihood of responding to immunotherapy or the likelihood of developing an immune-mediated side effect in response to said therapy, or to otherwise inform a course of clinical immunotherapy management.

Description of the Related Art

The adaptive immune system protects higher organisms against infections and other pathological events that can be attributable to foreign substances, using adaptive immune receptors, the antigen-specific recognition proteins that are expressed by hematopoietic cells of the lymphoid lineage and that are capable of distinguishing self from non-self molecules in the host. These lymphocytes can be found in the circulation and tissues of a host, and their recirculation between blood and the lymphatics has been described, including their extravasation via lymph node high endothelial venules, as well as at sites of infection, inflammation, tissue injury and other clinical insults. (See, e.g., Stein et al., 2005 *Immunol.* 116:1-12; DeNucci et al., 2009 *Crit. Rev. Immunol.* 29:87-109; Marelli-Berg et al., 2010 *Immunol.* 130:158; Ward et al., 2009 *Biochem. J.* 418:13; Gonzalez et al., 2011 *Ann. Rev. Immunol.* 29:215; Kehrl et al., 2009 *Curr. Top. Microb. Immunol.* 334:107; Steinmetz et al., 2009 *Front. Biosci.* (*Schol. Ed.*) 1:13.)

Accordingly, the dynamic nature of movement by lymphocytes throughout a host organism is reflected in changes in the qualitative (e.g., antigen-specificity of the clonally expressed adaptive immune receptor (immunoglobulin or T cell receptor), T cell versus B cell, T helper ($T_h$) cell versus T regulatory ($T_{reg}$) cell, effector T cell versus memory T cell, etc.) and quantitative distribution of lymphocytes among tissues, as a function of changes in host immune status.

The adaptive immune system employs several strategies to generate a repertoire of T- and B-cell antigen receptors with sufficient diversity to recognize the universe of potential pathogens. B lymphocytes mature to express antibodies (immunoglobulins, Igs) that occur as heterodimers of a heavy (H) and light (L) chain polypeptide, while T lymphocytes express heterodimeric T cell receptors (TCR). The ability of T cells to recognize the universe of antigens associated with various cancers or infectious organisms is conferred by its T cell antigen receptor (TCR), which is a heterodimer comprising an α (alpha) chain and a β (beta) chain, or a γ (gamma) and a δ (delta) chain. The proteins that make up these chains are encoded by DNA that employs a unique mechanism for generating the tremendous diversity of the TCR. This multi-subunit immune recognition receptor associates with the CD3 complex and binds to peptides presented by the major histocompatibility complex (MEW) class I and II proteins on the surface of antigen-presenting cells (APCs). Binding of TCR to the antigenic peptide on the APC is a central event in T cell activation, which occurs at an immunological synapse at the point of contact between the T cell and the APC.

Each TCR peptide contains variable complementarity determining regions (CDRs), as well as framework regions (FRs) and a constant region. The sequence diversity of αβ T cells is largely determined by the amino acid sequence of the third complementarity-determining region (CDR3) loops of the α and β chain variable domains, which diversity is a result of recombination between variable ($V_\beta$), diversity ($D_\beta$), and joining ($J_\beta$) gene segments in the β chain locus, and between analogous $V_\alpha$ and $J_\alpha$ gene segments in the α chain locus, respectively. The existence of multiple such gene segments in the TCR α and β chain loci allows for a large number of distinct CDR3 sequences to be encoded. CDR3 sequence diversity is further increased by deletion and template-independent addition of nucleotides at the $V_\beta$-$D_\beta$, $D_\beta$-$J_\beta$, and $V_\alpha$-$J_\alpha$ junctions during the process of TCR gene rearrangement. In this respect, immunocompetence is reflected in the diversity of TCRs.

The γδ TCR is distinctive from the αβ TCR in that it encodes a receptor that interacts closely with the innate immune system. TCRγδ, is expressed early in development, has specialized anatomical distribution, has unique pathogen and small-molecule specificities, and has a broad spectrum of innate and adaptive cellular interactions. A biased pattern of TCRγ V and J segment expression is established early in ontogeny as the restricted subsets of TCRγδ cells populate the mouth, skin, gut, vagina, and lungs prenatally. Consequently, the diverse TCRγ repertoire in adult tissues is the result of extensive peripheral expansion following stimulation by environmental exposure to pathogens and toxic molecules.

Igs expressed by B cells are proteins consisting of four polypeptide chains, two heavy chains (H chains) and two light chains (L chains), forming an $H_2L_2$ structure. Each pair of H and L chains contains a hypervariable domain, consisting of a $V_L$ and a $V_H$ region, and a constant domain. The H chains of Igs are of several types, μ, δ, γ, α, and β. The diversity of Igs within an individual is mainly determined by the hypervariable domain. Similar to the TCR, the V domain of H chains is created by the combinatorial joining of the $V_H$, $D_H$, and $J_H$ gene segments. Hypervariable domain sequence diversity is further increased by deletion and template-independent addition of nucleotides at the $V_H$-$D_H$, $D_H$-$J_H$, and $V_H$-$J_H$ junctions during the process of Ig gene rearrangement. In this respect, immunocompetence is reflected in the diversity of Igs.

Quantitative characterization of adaptive immune cells based on the presence in such cells of functionally rearranged Ig and TCR encoding genes that direct productive expression of adaptive immune receptors has been achieved using biological samples from which adaptive immune cells can be readily isolated in significant numbers, such as blood, lymph or other biological fluids. In these samples, adaptive immune cells occur as particles in fluid suspension. See, e.g., US 2010/0330571; see also, e.g., Murphy, *Janeway's Immunobiology* (8th Ed.), 2011 Garland Science, NY, Appendix I, pp. 717-762.

The adaptive immune system has long been implicated as having a role in the recognition of cancer cells, and in the ensuing generation of an immune response to eliminate tumors (e.g., Murphy, *Janeway's Immunobiology* (8th Ed.), 2011 Garland Science, NY, pp. 682-697; Pandolfi et al., 2011 *Clin. Dev. Immunol.* Article ID894704; Draghiciu et al., 2011 *Clin. Dev. Immunol.* Article ID439053). Variability among the antigenic profiles presented by different cancer cells, and variability in the robustness of different individuals' anti-tumor immune responses, have led to a number of widely different clinical approaches that are generally referred to as cancer immunotherapy, by which efforts are made to induce, recruit, enhance or otherwise potentiate the adaptive immune response, in this context, by encouraging anti-tumor immunity.

Such immunotherapeutic approaches represent preferable alternatives to conventional cancer therapies, that can be non-cancer cell-specific and can involve harsh cytotoxic regimens such as radiation and chemotherapy. Cancer immunotherapy is sometimes administered to patients who also receive chemotherapy and/or radiation therapy, but because chemotherapy and radiation are particularly cytotoxic toward dividing cells, whilst immunocyte proliferation can be a cardinal feature of many immune responses, such approaches can counterproductively compromise the adaptive immune system and thus can be accompanied by difficulties in arriving at effective therapeutic regimens.

Accordingly, it would be desirable to have a detailed understanding of a patient's immunological status in order to design an effective immunotherapy regimen, in the context of cancer and also, for example, in cases of hematopoietic cell transplant or solid organ transplant (e.g., to detect and appropriately treat immunological rejection of a graft), in the treatment of microbial infections, and to optimize responses to vaccines. The presently-described embodiments address these needs and provide other related advantages.

SUMMARY OF INVENTION

According to certain embodiments of the present invention, a method is provided for determining an immunological status of a test subject, comprising obtaining nucleic acid sequence information generated from one or more samples comprising nucleic acids from lymphoid cells of said test subject, wherein said nucleic acid sequence information comprising sequences for a plurality of unique rearranged nucleic acid sequences, each of said plurality of unique rearranged nucleic acid sequences encoding an AIR polypeptide, said one or more samples obtained from said test subject at one or more time points for said one or more samples, using said nucleic acid sequence information, determining a total number of observed rearranged sequences in said sample; determining a total number of unique rearranged DNA sequences in said sample; quantifying an AIR sequence diversity score for said one or more samples based on said total number of unique rearranged DNA sequences; quantifying an AIR sequence distribution score for said one or more samples by calculating a frequency of occurrence of each unique rearranged DNA sequence as a percentage of said total number of observed rearranged sequences in said one or more samples; and determining a test subject rating score for determining said immunological status of said test subject based on said AIR sequence diversity score and said AIR sequence distribution score of said test subject.

In some embodiments, the method includes comparing said test subject rating scores for said one or more samples to a second set of control subject rating scores obtained from samples from a control subject and determining said immunological status of said test subject at said one or more time points, wherein said test subject is determined to have a immunological status at said one or more time points that is different from an immunological status of said control subject, if a difference between said test subject rating score and said control subject rating score is statistically significant and wherein said test subject is determined to have the same immunological status of said control subject if there is no statistically significant difference between said test subject rating score and said control subject rating score.

In certain embodiments, the nucleic acids comprise genomic DNA. In other embodiments, the nucleic acids comprise cDNA. In some embodiments, the nucleic acids comprise messenger RNA.

In some embodiments, the methods of the invention also include steps for quantifying an AIR sequence distribution score for said subject comprising determining a number of unique rearranged AIR sequences that have a combined frequency of occurrence of up to 50% of the total number of observed rearranged sequences in said sample; and characterizing a AIR sequence distribution score as a low score if the number of unique rearranged AIR sequences that have a combined frequency of occurrence of up to 50% of the total number of observed rearranged sequences in said sample is less than or equal to a predetermined threshold.

In one embodiment, the method includes quantifying an AIR sequence distribution score for said subject comprising determining a number of unique rearranged AIR sequences that have a combined frequency of occurrence of up to 40% of the total number of observed rearranged sequences in said sample; and characterizing a AIR sequence distribution score as a low score if the number of unique rearranged AIR sequences that have a combined frequency of occurrence of up to 40% of the total number of observed rearranged sequences in said sample is less than or equal to a predetermined threshold.

In another embodiment, the method includes quantifying an AIR sequence distribution score for said subject comprising determining a number of unique rearranged AIR sequences that have a combined frequency of occurrence of up to 30% of the total number of observed rearranged sequences in said sample; and characterizing a AIR sequence distribution score as a low score if the number of unique rearranged AIR sequences that have a combined frequency of occurrence of up to 30% of the total number of observed rearranged sequences in said sample is less than or equal to a predetermined threshold.

In yet another embodiment, the method includes quantifying an AIR sequence distribution score for said subject comprising determining a number of unique rearranged AIR sequences that have a combined frequency of occurrence of up to 20% of the total number of observed rearranged sequences in said sample; and characterizing a AIR sequence distribution score as a low score if the number of unique rearranged AIR sequences that have a combined frequency of occurrence of up to 20% of the total number of observed rearranged sequences in said sample is less than or equal to a predetermined threshold.

In other embodiments, the method comprises quantifying an AIR sequence distribution score comprising selecting at least one unique rearranged sequence having the highest frequency of occurrence at each time point compared with the frequency of occurrences for each of the remaining unique rearranged sequences in said sample and determining a profile of AIR sequence distribution for said at least one unique rearranged sequence over time in said test subject.

In another embodiment, the method comprises selecting a plurality of the most abundant unique AIR rearranged sequence having a frequency of occurrence at each time point that is statistically significantly higher than an average frequency of occurrence for the total number of unique rearranged DNA sequences and determining a profile of AIR sequence distribution for each of said most abundant unique rearranged sequences over time in said test subject.

In yet another embodiment, the method includes quantifying said AIR sequence diversity score comprises determining a total number of unique clones in said sample.

In certain embodiments, the control subject has a known immunological status. In one embodiment, the control subject is a healthy subject and has an uncompromised immunological status. In another embodiment, the control subject has a compromised immunological status.

In some embodiments, the control subject has a known outcome of response to immunotherapy. In one embodiment, the response is a positive response to immunotherapy. In an embodiment, the response is a poor response to immunotherapy.

In another embodiment, the test subject is predicted to have the same outcome of response to immunotherapy as compared to the control subject. In yet another embodiment, test subject is predicted to have a different outcome of response to immunotherapy as compared to the control subject.

In certain embodiments, the control subject has a known outcome of response to a stem cell transplant. In one embodiment, the response can be a positive response to the stem cell transplant. In another embodiment, the response is a poor response to the stem cell transplant. In yet another embodiment, the test subject is predicted to have the same outcome of response to the stem cell transplant as compared to the control subject. In other embodiments, the test subject is predicted to have a different outcome of response to the stem cell transplant as compared to the control subject.

In certain aspects, the control subject has a known outcome of response to a treatment. In some aspects, the treatment comprises an immunotherapeutic antibody, a cytokine, a hematopoietic cell transplant, an immunosuppressive agent, or a vaccine.

In other aspects, the one or more samples comprise solid tissue samples obtained from the test subject.

In one aspect, the one or more samples comprise blood samples obtained from the test subject. In certain embodiments, where the one or more samples comprise blood samples, a low AIR sequence diversity score and a low AIR sequence distribution score are characterized as a low test subject rating score and are indicative of a high TCR clonality in said test subject. In other embodiments, a low test subject rating score is predictive of a poor response to immunotherapy in said test subject. In another embodiment, a high AIR sequence diversity score and a high AIR sequence distribution score are characterized as a high test subject rating score and are indicative of a low TCR clonality. In other embodiments, a high test subject rating score is predictive of a positive response to immunotherapy in said test subject.

In other embodiments, the test subject has been treated with immunotherapy. In some embodiments, the immunotherapy comprises administration of an inhibitor of a negative regulator of the immune system. In one embodiment, the negative regulator is selected from a group consisting of CTLA-4 and PD-1. In another embodiment, the negative regulator is CTLA-4. In yet another embodiment, the negative regulator is PD-1. In certain aspects, the inhibitor is an anti-CTLA-4 antibody. In another aspect, the inhibitor is an anti-PD-1 antibody.

In yet other aspects, the one or more samples comprise solid tumor samples obtained from the test subject. In some embodiments, in solid tumor samples, a high AIR sequence diversity score and a high AIR sequence distribution score are characterized as a low test subject rating score and are indicative of a low TCR clonality in said test subject.

In one embodiment, in solid tumor samples, a low test subject rating score is predictive of a poor response to immunotherapy. In another embodiment, a low AIR sequence diversity score and a low AIR sequence distribution score are characterized as a high test subject rating score and are indicative of a high TCR clonality. In one embodiment, a high test subject rating score is predictive of a positive response to immunotherapy in said subject.

In another embodiment, the test subject has been treated with immunotherapy. In one embodiment, the immunotherapy comprises administration of an inhibitor of a negative regulator of the immune system. In some aspects, the negative regulator is selected from a group consisting of CTLA-4 and PD-1. In one embodiment, the negative regulator can be CTLA-4. In another embodiment, the negative regulator can be PD-1. In other embodiments, the inhibitor is an anti-CTLA-4 antibody. In yet other embodiments, the inhibitor is an anti-PD-1 antibody.

The method also includes determining a side effect of an immunotherapy treatment for said test subject indicated by a clonal expansion of at least one clone that has a frequency of occurrence that is statistically significantly different from a mean frequency of occurrence of a set of remaining clones in a sample obtained after said immunotherapy treatment. In one embodiment, the set of remaining clones comprise clones each having a frequency of occurrence that is in the top 50% of the total clones in said sample. In another embodiment, the set of remaining clones comprise clones each having a frequency of occurrence that is in the top 40% of the total clones in said sample. In yet another embodiment, the set of remaining clones comprise clones each having a frequency of occurrence that is in the top 30% of the total clones in said sample. In other embodiments, the set of remaining clones comprise clones each having a frequency of occurrence that is in the top 20% of the total clones in said sample. In one embodiment, the set of remaining clones comprise clones each having a frequency of occurrence that is in the top 10% of the total clones in said sample. In one aspect, the at least one clone has a frequency of occurrence that is statistically significantly different from clones each having a frequency of occurrence that is in the top quartile of frequency of occurrences in said sample. In other aspects, the clonal expansion of said at least one clone is indicative of a poor response of said test subject to said immunotherapy treatment.

In certain aspects, the method also includes amplifying nucleic acid sequences obtained from at least one of said samples comprising lymphoid cells of a test subject in a multiplexed polymerase chain reaction (PCR) assay using (1) a plurality of AIR V-segment oligonucleotide primers and (2) either a plurality of AIR J-segment oligonucleotide primers or a plurality of AIR C-segment oligonucleotide primers.

In some embodiments, the plurality of AIR V-segment oligonucleotide primers are each independently capable of specifically hybridizing to at least one polynucleotide encoding a mammalian AIR V-region polypeptide, wherein each AIR V-segment oligonucleotide primer comprises a nucleotide sequence of at least 15 contiguous nucleotides that is complementary to at least one functional AIR-encoding gene segment, wherein said plurality of AIR V-segment oligonucleotide primers specifically hybridize to substantially all functional AIR V-encoding gene segments that are present in said sample. In one embodiment, the plurality of J-segment oligonucleotide primers are each independently capable of specifically hybridizing to at least one polynucleotide encoding a mammalian AIR J-region polypeptide, wherein each J-segment primer comprises a nucleotide sequence of at least 15 contiguous nucleotides that is complementary to at least one functional AIR J-encoding gene segment, wherein said plurality of J-segment primers specifically hybridize to substantially all functional AIR J-encoding gene segments that are present in the sample. In another embodiment, the plurality of C-segment oligonucleotide primers are each independently capable of specifically hybridizing to at least one polynucleotide encoding a mammalian AIR C-region polypeptide, wherein each C-segment primer comprises a nucleotide sequence of at least 15 contiguous nucleotides that is complementary to at least one functional AIR C-encoding gene segment, wherein the plurality of C-segment primers specifically hybridize to substantially all functional AIR C-encoding or gene segments that are present in the sample.

In certain aspects, the plurality of AIR V-segment oligonucleotide primers, and (2) either said plurality of AIR J-segment oligonucleotide primers and said plurality of AIR C-segment oligonucleotide primers are capable of promoting amplification in said multiplex PCR of substantially all rearranged AIR CDR3-encoding regions in said sample to produce a plurality of amplified rearranged DNA molecules from a population of adaptive immune cells in said sample, said plurality of amplified rearranged DNA molecules being sufficient to quantify the full diversity of said AIR CDR3-encoding region in said at least one sample.

In some embodiments, each functional AIR V-encoding gene segment comprises a V gene recombination signal sequence (RSS) and each functional AIR J-encoding gene segment comprises a J gene RSS, wherein each amplified rearranged DNA molecule comprises (i) at least 10, 20, 30 or 40 contiguous nucleotides of a sense strand of said AIR V-encoding gene segment, wherein said at least 10, 20, 30 or 40 contiguous nucleotides are situated 5' to said V gene RSS and (ii) at least 10, 20 or 30 contiguous nucleotides of a sense strand of said AIR J-encoding gene segment, wherein said at least 10, 20 or 30 contiguous nucleotides are situated 3' to said J gene RSS. In one embodiment, each amplified rearranged DNA molecule in said plurality of amplified rearranged DNA molecules is less than 1500 nucleotides in length. In another embodiment, each amplified rearranged DNA molecule in said plurality of amplified rearranged DNA molecules is less than 1000 nucleotides in length. In yet another embodiment, each amplified rearranged DNA molecule in said plurality of amplified rearranged DNA molecules is less than 600 nucleotides in length. In other embodiments, each amplified rearranged DNA molecule in said plurality of amplified rearranged DNA molecules is less than 500 nucleotides in length. In one aspect, each amplified rearranged DNA molecule in said plurality of amplified rearranged DNA molecules is less than 400 nucleotides in length. In another aspect, each amplified rearranged DNA molecule in said plurality of amplified rearranged DNA molecules is less than 300 nucleotides in length. In yet another aspect, each amplified rearranged DNA molecule in said plurality of amplified rearranged DNA molecules is less than 200 nucleotides in length. In some embodiments, each amplified rearranged DNA molecule in said plurality of amplified rearranged DNA molecules is less than 100 nucleotides in length. In a preferred embodiment, each amplified rearranged DNA molecule in said plurality of amplified rearranged DNA molecules is between 50-600 nucleotides in length.

In some aspects, the method includes selecting a set of unique rearranged sequences in one of said samples having a frequency of occurrence that is statistically significantly higher compared with other unique rearranged sequences in said sample. In certain aspects, the high frequency of occurrence is determined by a pre-determined threshold percentage. In one aspect, the selected number of unique rearranged sequences in said set is determined by a pre-determined number. In other embodiments, the method includes determining from said set whether one of said high frequency unique rearranged sequences is persistent or transient, wherein a persistent unique rearranged sequence is present across two or more samples obtained from said test subject over subsequent periods of time, and wherein a transient unique rearranged sequence is present in only one sample obtained at one timepoint from said subject.

The method also includes determining a course of immunotherapy for said subject based on the presence of one or more persistent unique rearranged sequences in said two or more samples of said test subject, wherein the presence of persistent unique rearranged sequences indicates an increased likelihood that said subject has a healthy immune status. In some embodiments, the presence of said one or more persistent unique rearranged sequences in said subject is predictive of a positive response to immunotherapy treatment by said subject. The method of the invention includes determining a course of immunotherapy for said subject based on a presence of one or more transient unique rearranged sequences in said one or more samples of said test subject, wherein said presence of said one or more transient unique rearranged sequences indicates an increased likelihood that said subject has a compromised immune status. In another embodiment, the presence of said one or more transient unique rearranged sequences in said subject is predictive of a poor response to immunotherapy treatment by said subject.

In some embodiments, the method of the invention provides steps for categorizing a test subject having a low test subject rating score in said one or more samples as having a lower relative likelihood of responding to immunotherapy in comparison to a second subject having a higher rating score; and stratifying a patient population of test subjects according to relative likelihood of responding to immunotherapy. The method includes determining said test subject rating score comprises extrapolating based on a mathematical model a total AIR repertoire diversity of said test subject by sequencing said nucleic acid sequences from one of said samples and determining a test subject rating score from said total AIR repertoire diversity. In one embodiment, the mathematical model is an unseen species model.

In another embodiment, determining said test subject rating score comprises calculating a Shannon entropy score and a clonality score and determining a test subject rating score based on said Shannon entropy score and said clonality score. In one embodiment, the clonality score is a transform of the Shannon entropy score.

In other aspects of the invention, the adaptive immune receptor (AIR) polypeptide is a mammalian AIR polypeptide and is selected from a T cell receptor-gamma (TCRG) polypeptide, a T cell receptor-beta (TCRB) polypeptide, a T cell receptor-alpha (TCRA) polypeptide, a T cell receptor-delta (TCRD) polypeptide, an immunoglobulin heavy-chain (IGH) polypeptide, and an immunoglobulin light-chain (IGL) polypeptide. In some embodiments, the IGH polypeptide is selected from an IgM, an IgA polypeptide, an IgG polypeptide, an IgD polypeptide and an IgE polypeptide. The IGL polypeptide can be selected from an IGL-lambda polypeptide and an IGL-kappa polypeptide. In one embodiment, the mammalian AIR polypeptide is a human AIR polypeptide. In another embodiment, the mammalian AIR polypeptide is selected from a non-human primate AIR polypeptide, a rodent AIR polypeptide, a canine AIR polypeptide, a feline AIR polypeptide and an ungulate AIR polypeptide.

In certain embodiments, the test subject is selected from: a subject having or suspected of having a malignant condition, a subject who has received a hematopoietic cell transplant, a subject who has received a solid organ transplant, and subject having a microbial infection. In some embodiments, the malignant condition is selected from a hematologic malignancy, a melanoma, a sarcoma and a carcinoma. The malignant condition can be selected from malignant melanoma, small cell lung cancer, non-small cell lung cancer, renal cell carcinoma, pancreatic cancer, breast cancer, ovarian cancer and prostate cancer.

In other embodiments, the hematopoietic cell transplant is selected from a cord blood transplant, an autologous hematopoietic cell transplant, an allogeneic hematopoietic cell transplant, and a bone marrow transplant. In one embodiment, the hematopoietic cell transplant comprises an autologous T cell transplant.

In other aspects, the plurality of time points comprise timepoints during or after immunotherapy. In another aspect, the plurality of time points comprise timepoints prior to immunotherapy.

In other embodiments, the method includes steps for managing a treatment of said test subject who is undergoing immunotherapy based on a determination of said immunological status of said test subject. In one embodiment, the immunotherapy comprises a treatment with an immunotherapy agent that is selected from an immunotherapeutic antibody, a cytokine, a hematopoietic cell transplant, an immunosuppressive agent, and a vaccine.

In another embodiment, the immunotherapy comprises a treatment with an inhibitor of a negative regulator of an immune response. In some aspects, the negative regulator of an immune response is selected from CTLA4/CD152, LAG3/CD223, and PD-1/CD279. In an embodiment, the negative regulator of an immune response can be CTLA-4/CD152 and said inhibitor of said negative regulator of an immune response can be an anti-CTLA-4 antibody. In another embodiment, the anti-CTLA-4 antibody is selected from ipilimumab and tremelimumab. In some embodiments, the negative regulator of an immune response is PD-1/CD279 and said inhibitor of the negative regulator of an immune response is an anti-PD-1 antibody. In another embodiment, the immunotherapy comprises a treatment with an agent that targets a potentiator of an immune response. In yet another embodiment, the potentiator of an immune response is selected from 41BB/CD137, OX40/CD134 and CD40.

In other embodiments, the immunotherapy comprises a treatment of an inflammatory condition or an autoimmune disease with an inhibitor of an inflammatory pathway. In certain embodiments, the inflammatory condition or said autoimmune disease is selected from rheumatoid arthritis, psoriatic arthritis, ankylosing spondylitis, Crohn's disease and juvenile idiopathic arthritis. In one embodiment, the inflammatory pathway comprises at least one of tumor necrosis factor-alpha (TNFα), interferon-gamma (IFNγ), interleukin-1 (IL-1), interleukin-6 (IL-6), interleukin-8 (IL-8). In other embodiments, the inflammatory pathway comprises TNFα and said inhibitor of the inflammatory pathway is an agent that specifically binds to TNFα. In another embodiment, the agent that specifically binds to TNFα is selected from an anti-TNFα antibody and an artificial soluble TNFα receptor. In one embodiment, the anti-TNFα antibody is selected from adalimumab and infliximab and said artificial soluble TNFα receptor is etanercept.

In other embodiments, a computer-implemented method is provided for determining an immunological status of a test subject, comprising: storing data for a control subject obtained from a plurality of samples at various timepoints, said data comprising for each sample, nucleic acid sequence information for a plurality of unique rearranged nucleic acid sequences in said sample, an AIR sequence diversity score for said sample, a frequency of occurrence of each unique rearranged nucleic acid sequence in said sample, and a determined immunological status for said subject; determining rules by a processor for assessing an immunological status of a test subject based on said data of said control subject; inputting data for a test subject for a plurality of samples obtained at various timepoints before and after immunotherapy, said data comprising for each sample, nucleic acid sequence information for a plurality of unique rearranged nucleic acid sequences in said sample, an AIR sequence diversity score for said sample, and a frequency of occurrence of each unique rearranged nucleic acid sequence in said sample; and receiving a determination of an immunological status of said test subject. In some embodiments, the method includes determining a predicted response to immunotherapy of said test subject. In one embodiment, the data for said control subject comprises nucleic acid sequence information obtained from said control subject at a timepoint prior to immunotherapy treatment. In another embodiment, the data for said control subject comprises nucleic acid sequence information obtained from said control subject at a timepoint after immunotherapy treatment.

These and other aspects of the herein described invention embodiments will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ

DETAILED DESCRIPTION

I. Overview

Figure 1:
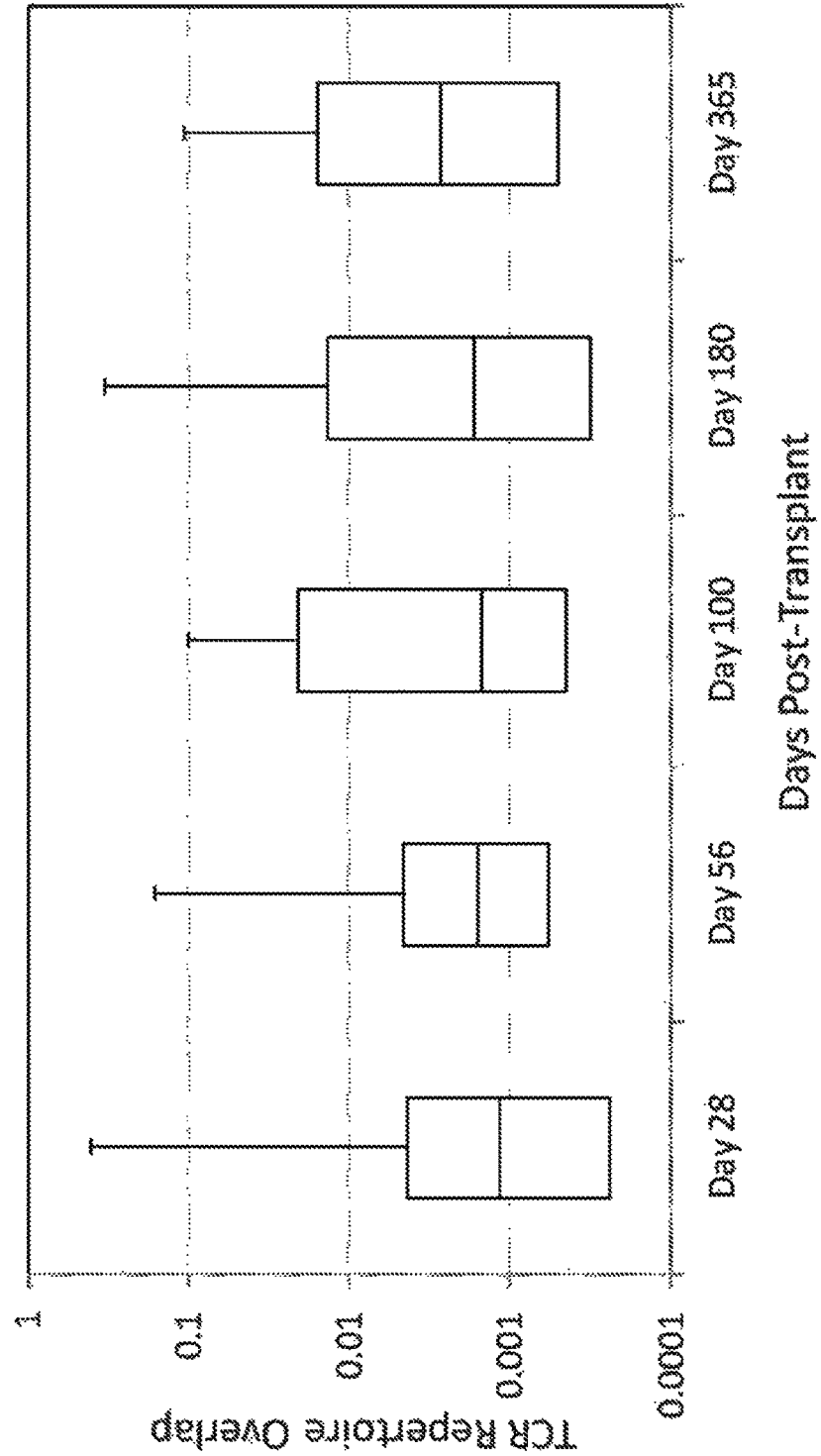
FIG. 1 illustrates TCR clones that remained over time after myeloablative treatment. Shown is the range of values for the proportion of each patient's repertoire represented by clones that were held over after stem cell transplant. The bottom quartile ranged to zero. The proportion of holdover clones was calculated as the proportion of total TCR sequencing reads corresponding to clones observed (at any level) before transplant. Values indicated some persistence of pre-transplant clones in these patients' TCR repertoires.

The present invention provides, in certain embodiments and as described herein, unexpectedly advantageous methods for determining the immunological status of a subject or of a plurality of subjects, including by qualitatively (e.g., by T cell receptor or immunoglobulin sequence diversity) and quantitatively (e.g., by TCR or IG sequence distribution) characterizing adaptive immune cell (e.g., T cell or B cell) clonality, from which immunocompetence of an individual's adaptive immune system can be assessed. The present embodiments thus provide novel methods for assessing the immunocompetence of an individual and for stratifying a population according to immune system status, where determination of both the sequence diversity of TCR and/or IG expressed by lymphoid cells in an individual, and the relative degree of T cell and/or B cell clonality in the individual, are of relevance to prognosis, diagnosis, and outcome, including likelihood of developing immune-related side effects, in a variety of clinical contexts.

The present embodiments for the first time permit high resolution, large-scale, high throughput assessment of immunocompetence by characterization at the DNA sequence level of (i) TCR and IG repertoire diversity, and (ii) TCR and IG repertoire distribution. The invention includes compositions and methods for quantitative detection of sequences of substantially all possible TCR and IG gene rearrangements that can be present in a sample containing lymphoid cell DNA.

In certain embodiments, a sample containing lymphoid cell DNA (genomic DNA, cDNA or alternatively, messenger RNA) from a subject is used as a template for multiplexed PCR amplification using a primer set that is specifically designed to be capable of amplifying substantially all possible DNA rearrangements encoding a particular TCR or IG chain. The multiplex PCR amplification products are amenable to rapid, high throughput, high quality quantitative DNA sequencing. Structural TCR or IG repertoire diversity in the sample is determined by identifying a plurality of unique rearranged DNA sequences from the DNA sequence information, and therefrom determining the total number of unique sequences in the sample.

Where desired, known estimation or extrapolation methods can be used to determine from the sequence information a repertoire diversity in the subject's entire adaptive immune system. To quantify the relative distribution of each unique sequence, quantitative sequencing methodologies described herein and practiced by those of skill in the art also permit determination of the frequency of occurrence of each particular uniquely rearranged DNA sequence amongst the total number of unique sequences. In certain embodiments, a blood sample can be obtained as the source of lymphoid cells from which lymphoid cell DNA and/or RNA can be extracted to provide PCR templates.

These and related methods will find a variety of uses as described herein. For example, the methods described herein are used to quantify the diversity and distribution of the adaptive immune receptor (AIR) repertoire within each individual subject's adaptive immune system. The methods described herein are also used to stratify a patient population according to the patient's immunocompetence status or the relative likelihood of individuals to respond to an immunotherapy or develop immune-related side effects. Quantification of AIR sequence diversity (e.g., the number of different unique AIR encoding sequences, identified by obtaining distinctive nucleotide sequence information for all rearranged DNA encoding a particular AIR polypeptide in a sample) and of AIR sequence distribution (e.g., frequency of occurrence of each unique rearranged AIR encoding DNA sequence) advantageously permits correlation of T or B cell clonality, defined with unprecedented precision, with clinically useful information.

By way of non-limiting theory, this sequence distribution can represent the degree of T cell or B cell clonality in each sample from a patient (e.g., quantitative degree of representation, or relative abundance). Any of a number of known computational tools for processing this distribution parameter can be used to generate distribution values (e.g., the frequency of occurrence of each unique sequence) and diversity values (e.g., the total number of different unique sequences). The distribution and diversity values can be used in a rating step to rate individual samples and compare them to a control sample and/or to one another.

As described herein, in patients receiving a cord blood transplant to treat hematologic malignancies, a relatively low degree of TCR repertoire diversity in patients following the cord blood transplant was shown to be a predictor of the relative likelihood of susceptibility to infection and of the immunological inability to clear the infection (e.g., poor response). On the other hand, a relatively high degree of TCR repertoire diversity in human patients following cord blood transplant to treat hematologic malignancies was shown to be a predictor of the relative likelihood of resistance to infection and of immunocompetence, i.e., the immunological ability to clear the infection.

In blood samples obtained from patients before and after immunotherapy with an inhibitor of a negative regulator of immune response (e.g., anti-CTLA4 antibody), a high TCR sequence diversity and low clonality in the blood of the patient correlated with positive clinical outcomes. On the other hand, a TCR repertoire that was characterized by a low TCR sequence diversity (high clonality) and a lower entropy of TCR sequence distribution was associated with poorer clinical outcomes that were attributable to compromised adaptive immune capability.

In solid tumor samples obtained from patients before and after immunotherapy with an inhibitor of a negative regulator of immune response (e.g., anti-PD-1 antibody), a high level of infiltrating T cell presence and high clonality (i.e., evidence of T cell migration to the tumor and clonal proliferation within the tumor) were associated with a positive response to immunotherapy. In contrast, a minimal infiltrating T cell repertoire and low clonality in solid tumors (i.e., evidence of a restricted and non-specific T cell response within the tumor) were associated with failure to respond to treatment.

The presently-disclosed embodiments will find a wide range of uses by profiling a subject's immunocompetence at a given point in time, for example, as a prognostic or diagnostic or to inform a therapeutic strategy, and for other purposes.

II. Definitions

Terms used in the claims and specification are defined as set forth below unless otherwise specified.

As used herein, adaptive immune receptor (AIR) refers to an immune cell receptor, such as a T cell receptor (TCR) or an Immunoglobulin (Ig) receptor found in mammalian cells.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly-available through the National Center for Biotechnology Information website (www.ncbi.nlm.nih.gov).

The term "sufficient amount" means an amount sufficient to produce a desired effect, e.g., an amount sufficient to modulate immune response in a cell.

The term "therapeutically effective amount" is an amount that is effective to ameliorate a symptom of a disease. A therapeutically effective amount can be a "prophylactically effective amount" as prophylaxis can be considered therapy.

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques can be used for recombinant technology, molecular biological, microbiological, chemical syntheses, chemical analyses, pharmaceutical preparation, formulation, and delivery, and treatment of patients.

Unless the context requires otherwise, throughout the present specification and claims, the word "comprise" and variations thereof, such as, "comprises" and "comprising" are to be construed in an open, inclusive sense, that is, as "including, but not limited to." By "consisting of" is meant including, and typically limited to, whatever follows the phrase "consisting of." By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and can or cannot be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%, etc. In other embodiments, the terms "about" or "approximately" when preceding a numerical value indicates the value plus or minus a range of 10%, 11%, 12%, 13% or 14%, etc. In yet other embodiments, the terms "about" or "approximately" when preceding a numerical value indicates the value plus or minus a range of 15%, 16%, 17%, 18%, 19% or 20%, etc.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

III. Quantification Methods

Various methods can be used to quantify and assess the immunocompetence of the subject. In some embodiments, the immunocompetence is assessed by measuring the subject's adaptive immune receptor (AIR) sequence diversity and AIR sequence distribution.

A. Adaptive Immune Receptor (AIR) Sequence Diversity

Diversity of unique rearranged TCR or IG encoding DNA sequences in lymphoid cells in a sample reflects the number of different T or B cell clones in a sample from a subject. Sequence diversity can be determined as the number of clones in a sample of a particular size, such as by direct counting or weighted counting in a sample. A sample can be a blood sample or a tissue sample (solid tumor sample), for example. Alternatively, the number of different clones in a subject can be estimated based on the number of clones in a subsample. In another embodiment, an arbitrary cutoff value can be assigned to estimate the number of different "effective" clones, such as counting toward diversity only those clones that account for greater than 0.01% of all T or all B cells in the sample. Other models for weighted or extrapolated diversity determinations are contemplated for use in certain related embodiments, such as entropy models, the "unseen species model" (see, e.g., Efron et al., 1976 *Biometrika* 63:435; Fisher et al., 1943 *J. Anim. Ecol.* 12:42) or other suitable models as will be known to those familiar with the art.

In some embodiments, AIR diversity can be measured by quantitative sequencing of the total AIR observed sequences in a particular sample. Compositions and methods for quantitative sequencing of rearranged adaptive immune receptor gene sequences and for adaptive immune receptor clonotype determination are described, for example, in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. aplication Ser. No. 13/217, 126, U.S. application Ser. No. 12/794,507, WO/2010/151416, WO/2011/106738 (PCT/US2011/026373), WO2012/027503 (PCT/U52011/049012), U.S. A. No. 61/550,311, and U.S. A. No. 61/569,118, herein incorporated by reference. Therein can also be found details regarding sequences of PCR amplification oligonucleotide primers and sequencing primers, sequencing of PCR amplification products, processing sequencing data, and uses of measurements of adaptive immune receptor diversity, all of which can be employed for use according to the methods described herein.

In some embodiments, a sequencing program such as Raw HiSeg™ can be used to preprocess sequence data to remove errors in the primary sequence of each read, and to compress the sequence data. A nearest neighbor algorithm can be used to collapse the data into unique sequences by merging closely related sequences, to remove both PCR and sequencing errors.

Quantitative sequencing of TCR or IG as described herein permits assignment of a diversity score or rating to a sample. In some embodiments, the diversity score or rating can be determined to be low when there are a small number of unique rearranged AIR sequences in the repertoire as compared to the total number of observed rearranged AIR sequences in a sample. The diversity score or rating can be higher when there is a large number of unique rearranged AIR sequences in the repertoire as compared to the total number of observed rearranged AIR sequences in a sample. The determination of a low or high diversity score or rating can be based on pre-determined thresholds or calculations of statistical significance, as can be determined by one of skill in the art. For example, a predetermined threshold for classifying a diversity score or rating as "low" can be, in some embodiments, a score that is not higher (with statistical significance) than that obtained from blood samples of a subject population, wherein the population can be a population determined to experience a poor outcome in response to an immunotherapeutic intervention. In other embodiments, the predetermined threshold is determined based on calculation of the top or highest 50%, 25%, 10% or 5% of diversity or rating scores determined from rearranged AIR sequences from the sample.

As a relative scale, the rating system can be varied or adjusted in view of a number of factors, including but not limited to, the sample size, method of diversity quantification (e.g., whether by direct sequencing, or by extrapolation, "hidden species," etc.), clinical signs and symptoms of the patient population from whom samples are obtained, etc. For instance, in certain non-limiting examples, members of a patient population can be categorized on the basis of relative diversity and/or distribution ratings, and in certain embodiments, arbitrary segmentation of the population can be practiced. In certain embodiments, the patient population can be stratified according to (i) the degree of sequence diversity or distribution by quartile, quintile, decile, etc., or (ii) by rating relative AIR sequence diversity and distribution entropy in 50, 40, 30, 20 or 10 percent of the total number of sequences as a correlate of clonality, or (iii) by selecting the 1, 2, 3, 4, 5, 6, 7, 8, 9, 10, 11, 12, 13, 14, 15, 16, 17, 18, 19 or 20 most abundant unique AIR sequences at each of a succession of timepoints. The categorization provides a set of parameters by which immunocompetence can be assessed.

As also noted above, using these sequence diversity calculations, it was determined that in blood samples obtained from patients having undergone hematopoietic stem cell transplantation, higher AIR sequence diversity scores correlated with higher likelihoods of favorable clinical outcomes, such as the ability to clear infections. In solid tumor samples obtained from patients undergoing immunotherapy with anti-PD-1 antibody, high levels of T cell infiltration and a low infiltrating T cell repertoire diversity were associated with a positive response to immunotherapy.

Other known methods for calculating AIR sequence diversity can be used as known to those of skill in the art. For example, the following works, which are incorporated by reference in their entireties, summarize the current theory and practice of estimating diversity indices from species abundance data, while giving detailed examples of several common embodiments of diversity index measurement. See Anne E. Magurran and Brian J. McGill. 2011. *Biological Diversity: Frontiers in Measurement and Assessment*. New York: Oxford University Press. Other examples of methods for genetic diversity estimation that can be applied to calculate a diversity score rating can be found in James F. Crow and Motoo Kimura. 2009. *An Introduction to Population Genetics Theory*. Blackburn Press.

B. Adaptive Immune Receptor (AIR) Sequence Distribution

In some embodiments, the AIR sequence distribution can be used to determine and assess a subject's immunological status (e.g., immunocompetence). AIR sequence distribution, such as TCR or IG sequence distribution, refers to the variation among the number of different T cell or B cell clones in a sample, e.g., the number of cells that express an identical TCR or IG. For example, AIR sequence distribution can be determined by quantifying the frequency of occurrence of each unique rearranged AIR encoding DNA sequence, as a percentage of the total number of observed rearranged AIR encoding DNA sequences. The quantified distribution of AIR sequences can be used, optionally along with AIR sequence diversity, to rate or rank the immunocompetence of a subject, according to certain presently-contemplated embodiments for determining immunological status.

In some embodiments, an AIR sequence distribution can be determined by, but not limited to, the following methods: (i) identifying and quantifying at least 1-20 of the most abundant unique rearranged (clonal) AIR sequences in a subject over a time interval, or (ii) by identifying and quantifying the number of unique rearranged (clonal) AIR sequences that are needed to account for a given percentage (e.g., up to 10, 20, 30, 40 or 50%) of the total number of observed rearranged sequences in a sample from a subject. Other calculations can additionally or alternatively be employed to determine AIR sequence distribution of a sample from a subject and to assign a sequence distribution value to a particular sample for purposes of rating the sample in comparison to a control or another sample with a known immunological status. These can include, for example, determining entropy (i.e., Shannon entropy as typically defined in information theory, which can be normalized to the range [0-1] by dividing by the logarithm of the number of elements in the sample set) or using other known methods to determine one or more modes of distribution (e.g., mean, skewness, kurtosis, etc.). The present methods permit determination of sequence distribution and clonality with a degree of precision not previously possible and permit a variety of prognostic, diagnostic, prescriptive and other capabilities.

C. Determining Immunological Status

According to certain embodiments, there is provided a method for determining immunological status of a test subject. In some embodiments, the method includes steps for identifying, quantifying, rating, comparing and categorizing the immunological status of the test subject.

In some embodiments, identifying DNA sequence information for each of a plurality of unique rearranged DNA sequences that encode an adaptive immune receptor (AIR) polypeptide in one or more samples containing lymphoid cell DNA obtained from a test subject at each of one or a plurality of timepoints, and determining a total number of unique rearranged AIR polypeptide encoding DNA sequences in the test subject at each of the one or a plurality of timepoints to quantify AIR sequence diversity in the subject can be performed as described above and in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. application Ser. No. 13/217,126, U.S. application Ser. No. 12/794,507, WO/2010/151416, WO/2011/106738 (PCT/US2011/026373), WO2012/027503 (PCT/US2011/049012), U.S. A. No. 61/550,311, and U.S. A. No. 61/569,118, herein incorporated by reference. These references provide description regarding sequences of PCR amplification oligonucleotide primers and sequencing primers, sequencing of PCR amplification products, processing sequencing data, and uses of measurements of adaptive immune receptor diversity.

After determining the total number of unique rearranged AIR polypeptide encoding DNA sequences in the test subject at each of said one or a plurality of timepoints, the frequency of occurrence of each unique rearranged DNA sequence can be quantified as a percentage of the total number of observed rearranged AIR polypeptide encoding DNA sequences. For example, if an AIR sequence diversity value is determined from a count of actual sequence data, that value can be used to determine AIR sequence distribution. In another example, if AIR sequence diversity data are estimated, such as by extrapolation of a subsample to the subject's full adaptive immune system, or using the "unseen species model," or by any other estimation method, then any of widely known method for capturing properties of a distribution can be employed.

1. Rating the Immunological Status of a Sample from a Subject

AIR sequence diversity and AIR sequence distribution values for each sample can be used to rate the immunological status of samples. Any of a wide variety of simple, weighted and/or sophisticated rating systems can be employed, as can depend on the diversity and distribution estimation methods that are used. Preferably and in certain non-limiting embodiments, a low rating is assigned to a test subject's sample in which a small number of unique rearranged sequences in reference to a predetermined threshold have a combined frequency of occurrence of no more than 50 percent of the total number of observed rearranged sequences. A higher test subject rating is assigned to a sample in which a higher number of unique rearranged sequences in reference to a predetermined threshold have a combined frequency of occurrence of no more than 50 percent of the total number of observed rearranged sequences. In other words, the rating is lower where a smaller number of different clones accounts for 50 percent of the total number of observed rearranged sequences, as would be the case where one or a few dominant clones or oligoclonality are present. In similar but related embodiments, a lower test subject rating is assigned to a sample in which a lower number of unique rearranged sequences have a combined frequency of occurrence of no more than 40, 30, 20 or 10 percent of the total number of observed rearranged sequences, and a higher test subject rating is assigned to a sample in which a higher number of unique rearranged sequences have, respectively, a combined frequency of occurrence of no more than 40, 30, 20 or 10 percent of the total number of observed rearranged sequences in the sample.

In some embodiments, the assigned ratings that can then be compared to control subject ratings generated from control lymphoid cell DNA samples obtained from a second subject with a known immunological status. In certain embodiments, the second subject has a known, compromised immunological status, as defined by one of skill in the art. In other embodiments, the second subject can be a healthy control individual with a known, uncompromised immunological status according to art-established criteria (e.g., Rich et al., *Clinical Immunology: Principles and Practice,* $3^{rd}$ Ed., Mosby, St. Louis). In some embodiments, the test subject can be categorized as having a compromised immunological status at each of said timepoints at which the test subject rating is lower, in a statistically significant manner, than the control subject rating, such that the immunological status of the test subject is thereby determined. As referred to herein, a "control subject" can refer to a population of control subjects each sharing a relevant clinical phenotype.

For example, and in certain preferred embodiments, a test subject can be categorized as having a compromised immunological status and/or an unhealthy immune status when a TCR or IG sequence diversity score for a sample from the test subject is, with statistical significance, two standard deviations below that of a sample from a control subject, wherein said control subject is known to have an uncompromised immunological status or a healthy immune status.

Similarly, in certain preferred embodiments a test subject can be regarded as having a compromised immunological status and/or an unhealthy immune status when a TCR or IG sequence distribution (entropy) score for a sample from the test subject is, with statistical significance, two standard deviations below that of a sample from a control subject, wherein said control subject is known to have an uncompromised immunological status or a healthy immune status. Status categorization can then inform diagnosis, prognosis and/or treatment strategies.

For instance and by way of non-limiting example, age-related decline in adaptive immune system capabilities can be detected according to the herein described methods, such that elderly patients can be immunologically profiled for purposes of predicting whether or not they would be likely to respond immunologically to a vaccine. As another non-limiting example, hematopoietic cell transplant recipients can be tested periodically post-transplant to determine whether or when adaptive immunity has been reconstituted by transplanted cells, so that prophylactic anti-infective (e.g., antibiotic, anti-viral, etc.) and/or immunosuppressive therapies (e.g., to treat graft-versus-host disease (GVHD)) can be adjusted on the basis of each patient's adaptive immune system status instead of on the basis of a fixed regimen. As another non-limiting example, the immune repertoire and immunocompetence of solid organ transplant recipients (e.g., a recipient of all or a portion of a transplanted liver, lung, kidney, pancreas, intestine, heart, or skin) can be tested periodically to determine whether and to what extent the host adaptive immune system can be involved in graft rejection. From such test results, the clinician can adjust immunosuppressive therapies as needed, for example, to palliate rejection or to reduce or avoid potentially deleterious side-effects of excessive immunosuppressive therapy.

In yet another non-limiting example, immunocompetence can be assessed as described herein in candidate immunotherapy recipients such as oncology patients, in order to predict which patients can be likely to respond positively to immunotherapy and which are unlikely to do so.

As also noted elsewhere herein, using the presently-disclosed methods, it has been determined that in tumor tissue samples obtained from patients in whom the TCR (TCRB) repertoire exhibited relatively higher TCR sequence diversity and high clonality of TCR sequence distribution (i.e., evidence of T cell migration to the tumor and clonal proliferation within the tumor) were more likely to benefit from immunotherapy designed to inhibit negative regulators of adaptive immune mechanisms (e.g., anti-PD-1 antibodies). Such patients responded beneficially to immunotherapy and had better clinical outcomes that were attributable to robust immune response within the tumor tissue as detected by the present methods (FIG. 10; FIG. 11). Thus, in the PD-1 study, it was determined that responders have many more infiltrating T cells than non-responders (i.e., there are more total infiltrating T cells present), but that those T cells are distributed quite unevenly (i.e., high clonality).

Figure 8:
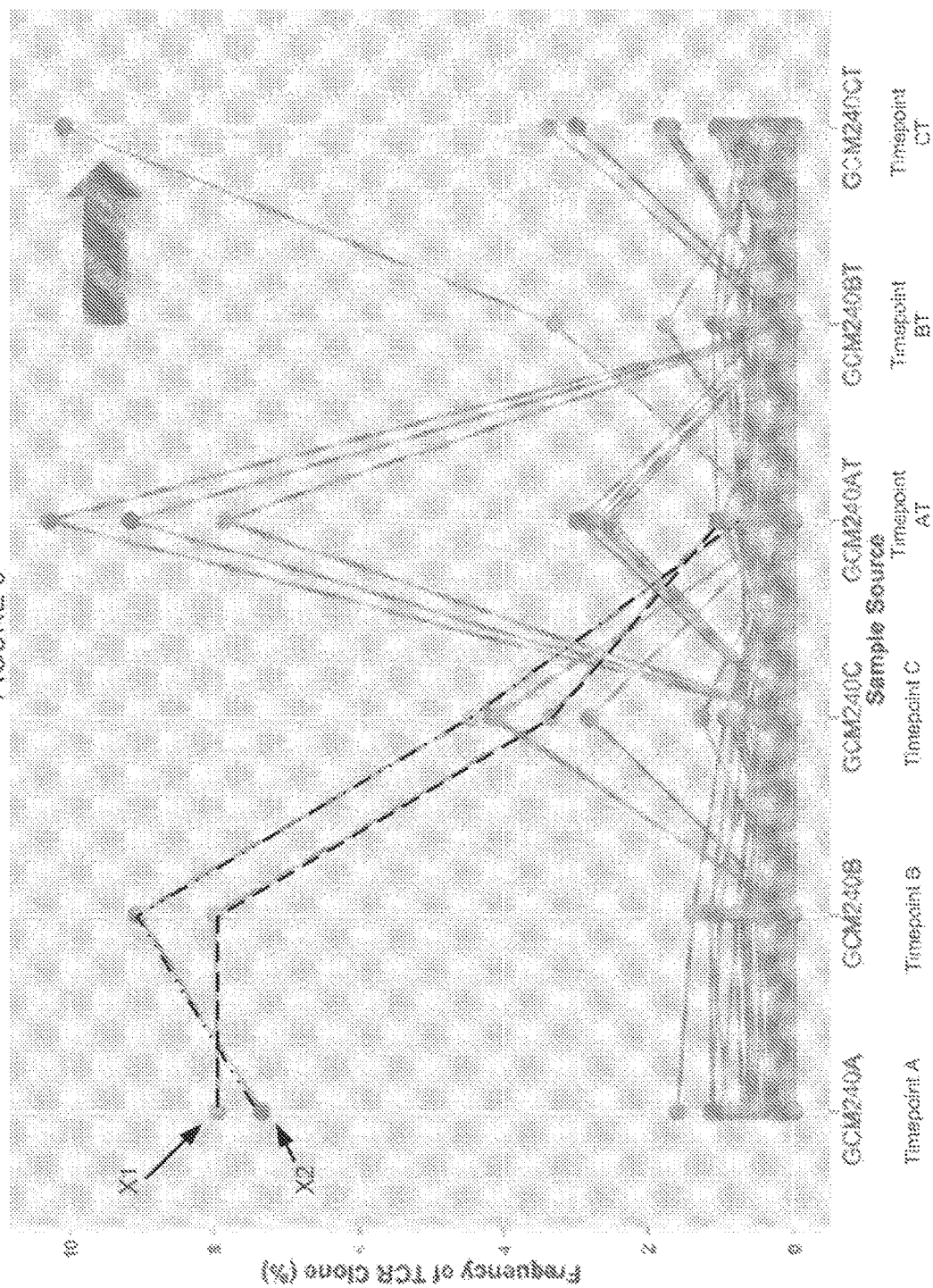
FIG. 8 shows dynamics in the relative representations of individual TCR clonal populations over time in blood samples and in solid tumor samples obtained prior to immunotherapy (treatment with ipilimumab (an anti-CTLA-4 mAb)) and post immunotherapy. Timepoints A, B, and C are timepoints taken from blood samples. Timepoint A is before immunotherapy, and timepoints B and C are two timepoints after starting the immunotherapy regimen. Timepoints AT, BT, CT are paired tumor samples (AT is before immunotherapy, and timepoints BT and CT are two timepoints after starting the immunotherapy regimen). The arrow indicates a single clone that has increased in preponderance post-therapy to account for 10% of the repertoire at timepoint CT. Two clones (X1 and X2) that each accounted for 7-9% of TCR sequences in blood at timepoints A and B subsequently declined significantly in relative abundance, while several T cell receptor sequences that initially had very low frequencies in blood increased significantly by timepoint C. The three most numerous clones in tumor samples at timepoint A decreased significantly in their subsequent relative representation, as determined at later timepoints.
Figure 9:
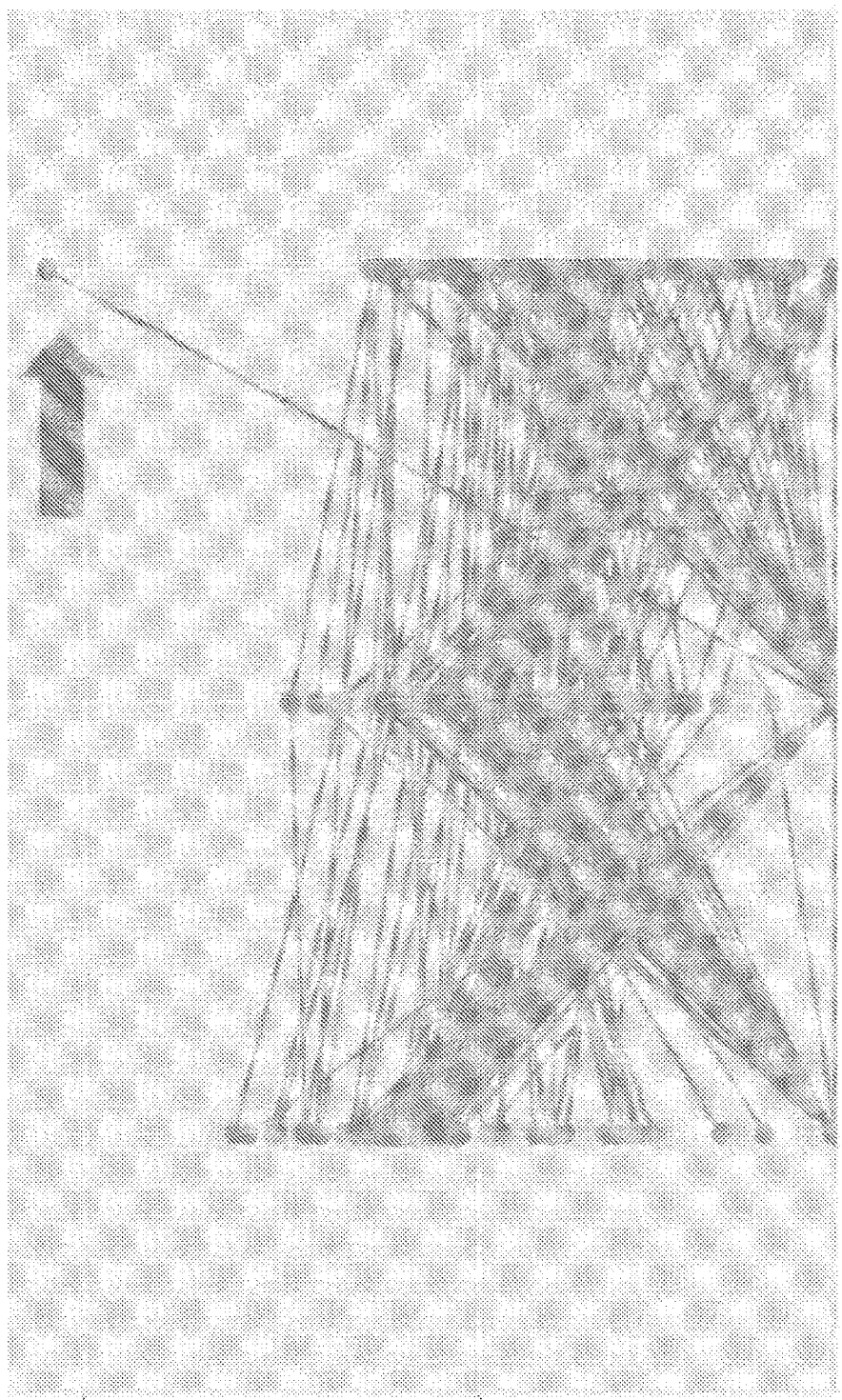
FIG. 9 shows TCR sequence diversity and distribution entropies determined in peripheral blood samples obtained prior to (timepoint A) and after (timepoints B and C) initiation of immunotherapy (treatment with ipilimumab (an anti-CTLA-4 mAb)) shows dynamics of individual TCR clonal representations over time, pre-therapy (timepoint A) and post-therapy (timepoints B and C). Arrow indicates a single clone that has increased in preponderance post-therapy to account for greater than 10% of the repertoire at timepoint C.

In a different study, it was further observed that in a subset of non-responder subjects, there was a decline in both TCRB sequence diversity and sequence distribution entropy shortly after immunotherapy (with anti-CTLA-4 antibody) was first administered, indicating differential responses to immunotherapy that can be measured by the present methods (FIG. 8; FIG. 9).

2. Amplification and Primers

According to these and related embodiments of the herein described methods, the method includes amplifying DNA extracted from or generated from the sample in a multiplexed PCR using (1) a plurality of AIR V-segment oligonucleotide primers and (2) either a plurality of AIR J-segment oligonucleotide primers or a plurality of AIR C-segment oligonucleotide primers. These primers are also described in detail in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. application. Ser. No. 13/217,126, U.S. application Ser. No. 12/794,507, WO/2010/151416, WO/2011/106738 (PCT/US2011/026373), WO2012/027503 (PCT/US2011/049012), U.S. A. No. 61/550,311, and U.S. A. No. 61/569,118. The plurality of V-segment oligonucleotide primers are each independently capable of specifically hybridizing to at least one polynucleotide encoding a mammalian AIR V-region polypeptide, wherein each V-segment primer comprises a nucleotide sequence of at least 15 contiguous nucleotides that is complementary to at least one functional AIR-encoding gene segment and wherein the plurality of V-segment primers specifically hybridize to substantially all functional AIR V-encoding gene segments that are present in the sample. The plurality of J-segment oligonucleotide primers are each independently capable of specifically hybridizing to at least one polynucleotide encoding a mammalian AIR J-region polypeptide, wherein each J-segment primer comprises a nucleotide sequence of at least 15 contiguous nucleotides that is complementary to at least one functional AIR J-encoding gene segment and wherein the plurality of J-segment primers specifically hybridize to substantially all functional AIR J-encoding or gene segments that are present in the sample. Moreover, the plurality of C-segment oligonucleotide primers are each independently capable of specifically hybridizing to at least one polynucleotide encoding a mammalian AIR C-region polypeptide, wherein each C-segment primer comprises a nucleotide sequence of at least 15 contiguous nucleotides that is complementary to at least one functional AIR C-encoding gene segment and wherein the plurality of C-segment primers specifically hybridize to substantially all functional AIR C-encoding or gene segments that are present in the sample. In some embodiments, the V-segment and J- or C-segment primers are capable of promoting amplification in said multiplex polymerase chain reaction (PCR) of substantially all rearranged AIR CDR3-encoding regions in the sample to produce said plurality of amplified rearranged DNA molecules from a population of adaptive immune cells in the sample, said plurality of amplified rearranged DNA molecules being sufficient to quantify diversity of the AIR CDR3-encoding region in the population of T cells. Alternatively, the method can simply involve sequence analysis of the aforementioned amplified DNA sequence data sufficient to characterize the sample with respect to the absolute and/or relative number of distinct clones present in the sample. As used herein, a functional AIR-encoding gene segment refers to a TCR or IG encoding gene segment that has undergone rearrangement in the DNA of a lymphoid cell and that is productively expressed, for instance, such that in preferred embodiments rearrangements that involve pseudogenes are not included, nor are rearrangements that result in an out-of-frame or prematurely terminated AIR polypeptide.

Methods of amplification, sequencing and primers are discussed in further detail herein.

3. Stratification of Patient Populations

According to certain related embodiments disclosed herein, there is provided a method for stratifying a patient population according to relative likelihood of responding to immunotherapy, comprising the following steps:

(a) identifying, in at least one sample (e.g., a solid tumor sample) containing lymphoid cell nucleic acid from each of a plurality of patients who are candidate immunotherapy recipients, nucleic sequence information for each of a plurality of unique rearranged nucleic acid sequences that encode an adaptive immune receptor (AIR) polypeptide, and therefrom determining a total number of unique rearranged AIR polypeptide encoding nucleic acid sequences in each patient to quantify AIR sequence diversity in the subject;

(b) quantifying, in each of the plurality of patients, a frequency of occurrence of each unique rearranged nucleic sequence identified in (a) as a percentage of the total number of observed rearranged AIR polypeptide encoding nucleic sequences to determine AIR sequence distribution in the subject;

(c) rating each of the plurality of patients according to the total number of unique rearranged sequences in the patient from (a) and according to the frequency of occurrence of each unique rearranged sequence in the patient from (b), giving lower clonality ratings to patients in whom the Shannon entropy (calculated from the distribution of the frequency of each unique rearranged AIR and normalized to the range [0-1] by dividing by the logarithm of the number of unique rearranged AIRs) is high (i.e., indicating an AIR repertoire with little specific clonal expansion) and giving higher clonality ratings to patients in whom the Shannon entropy (calculated from the distribution of the frequency of each unique rearranged AIR and normalized to the range [0-1] by dividing by the logarithm of the number of unique rearranged AIRs) is low (i.e., indicating an AIR repertoire with extensive specific clonal expansion); and (d) categorizing a patient having a lower clonality rating (as measured from a solid tumor sample) as having a lower relative likelihood of responding to immunotherapy than does a patient having a higher clonality rating, and thereby stratifying the patient population according to relative likelihood of responding to immunotherapy. In some embodiments, the at least one sample is a solid tumor sample.

Practicing these method steps employs compositions and methodologies similar to those described elsewhere herein.

4. Determining Immunological Status for Managing Treatment

According to certain other related embodiments, there is provided a method for determining immunological status to manage treatment of a test subject undergoing immunotherapy, comprising the following steps:

(a) identifying, in one or more samples containing lymphoid cell DNA obtained from a test subject at each of one or a plurality of timepoints prior to immunotherapy and at each of one or a plurality of timepoints during or after immunotherapy, nucleic acid sequence information for each of a plurality of unique rearranged nucleic acid sequences that encode an adaptive immune receptor (AIR) polypeptide, and therefrom determining a total number of unique rearranged AIR polypeptide encoding nucleic acid sequences in the test subject at each of said one or a plurality of timepoints to quantify AIR sequence diversity in the subject;

(b) quantifying, in each of the one or more samples, a frequency of occurrence of each unique rearranged nucleic acid sequence identified in (a) as a percentage of the total number of unique rearranged AIR polypeptide encoding nucleic acid sequences in the test subject at each of said one or a plurality of timepoints to determine AIR sequence distribution in the subject at each of said one or a plurality of timepoints;

(c) rating each of the one or more samples according to the total number of unique rearranged sequences determined in (a) and according to the frequency of occurrence of each unique rearranged sequence quantified in (b), and using the AIR frequency distribution to extrapolate the number of total unique AIR sequences in the subject at each of said one or a plurality of timepoints, to obtain a profile of AIR sequence diversity over time in the test subject, and (d) assigning an altered course of immunotherapy to the subject based on extrapolated total AIR sequence diversity, wherein high extrapolated total AIR sequence diversity indicates increased likelihood the subject has a healthy immune status and will be able to successfully clear infections and low extrapolated total AIR sequence diversity indicates increased likelihood the subject has an unhealthy immune status and will be unable to successfully clear infections.

Practicing these method steps employs compositions and methodologies similar to those described elsewhere herein.

IV. Immunotherapy and Immunocompetence

Immunocompetence can be usefully understood to include the capacity or potential of an individual's adaptive immune system to mount an effective immune response, such as an immune response that is directed to a particular tumor or to a pathogen (e.g., an infective bacteria, virus, fungus or other microbial or disease-causing agent) such that the tumor or pathogen is eradicated or neutralized. According to certain embodiments of the present disclosure, there are described methods for assessing immunocompetence, which methods can be predictive of an individual's likelihood of responding in a clinically beneficial manner to immunotherapy.

Hence and as also described elsewhere herein, an immunocompetent adaptive immune system, such as that of a clinically healthy, normal individual, or population of individuals, known by clinical criteria to be free of any risk or presence of disease or immunological disorder, will be characterized by a relatively high degree of AIR sequence diversity and high entropy of AIR sequence distribution in samples obtained from the subject's blood. Conversely, an immunoincompetent adaptive immune system (e.g., relatively poor capacity of an adaptive immune system to mount an immune response) is shown herein to be characterized by relatively low AIR sequence diversity and low entropy of AIR sequence distribution in samples obtained from the subject's blood. AIR sequence diversity and entropy of AIR sequence distribution are herein shown to be dynamic over time, and can tend to decline over time as a correlate of increasing age, increasing susceptibility to disease, decreasing likelihood of responding robustly to vaccines or to other immunotherapies, and/or other clinically relevant criteria.

In some embodiments, in solid tumor samples obtained from patients before and after immunotherapy with an inhibitor of a negative regulator of immune response, a high level of infiltrating T cells and high clonality were associated with a positive response to immunotherapy. In contrast, a low level of infiltrating T cells and low clonality in solid tumors were associated with failure to respond to treatment.

Immunotherapy can include any of a variety of interventions by which the activity levels of one or more cells of the adaptive immune system are altered (e.g., up- or down-regulated in a statistically significant manner). For example, the intervention can induce, recruit, enhance or otherwise potentiate an adaptive immune response, which in preferred embodiments will be an antigen-specific immune response. In certain embodiments, immunotherapy can comprise administration of one or more specific antibodies that recognize adaptive immune system cells to alter the immunological activity of such cells. Other immunotherapeutic approaches include the use of cytokines that similarly can directly or indirectly alter immunocyte activity; vaccines that elicit adaptive immune responses such as antigen-specific responses to tumor-associated antigens; hematopoietic cell transplants which include bone marrow transplants, cord blood transplants and autologous hematopoietic cell transplants including autologous T cell transplants (e.g., Blume and Thomas, 2000 *Biol. Blood Marrow Transpl.* 6(1):1-12); inhibitors of negative regulators of adaptive immune responses such as inhibitors of CTLA4/CD152 (e.g., ipilimumab, tremelimumab; Callahan et al., 2010 *Sem. Oncol.* 37:473), inhibitors of LAG3/CD223 (Huard et al., 1996 *Eur. J. Immunol.* 26:1180; Baixeras et al., 192 *J. Exp. Med.* 176:327; Hannier et al., 1998 *J. Immunol.* 161:4058; Huard et al., 1994 *Eur. J Immunol.* 24:3216); and other immunotherapeutic agents including in some cases immunosuppressive agents (e.g., *Goodman & Gilman's The Pharmacological Basis of Therapeutics*, (12$^{th}$ Ed., Brunton et al., Eds., McGraw Hill, NY, 2011, pages 909-1099; 1891-1990; Murphy, *Janeway's Immunobiology* (8$^{th}$ Ed.), 2011 Garland Science, NY, pp. 669-716).

Accordingly, in certain embodiments, immunotherapy can comprise treatment with an immunotherapy agent, such as an immunotherapeutic antibody, a cytokine, a hematopoietic cell transplant, an immunosuppressive agent, or a vaccine. In certain embodiments, immunotherapy comprises treatment with an inhibitor of a negative regulator of an immune response. The negative regulator of an immune response can be one or more of CTLA4/CD152, LAG3/CD223, and PD-1/CD279. For example, the negative regulator of an immune response can be CTLA-4/CD152 and the inhibitor of the negative regulator of an immune response is an anti-CTLA-4 antibody, such as ipilimumab (e.g., Lyseng-Williamson et al., 2012 *Am. J. Clin. Dermatol.* 13:349; Jeter et al., 2012 *Clin. Med. Insights Oncol.* 6:275; Waitz et al., 2012 *Canc. Res.* 72:430) or tremelimumab (e.g., Callahan et al., 2010 *Sem. Oncol.* 37:473; Ascieto et al. 2011 *J Transl. Med.* 9:196; Calabro et al., 2010 *Sem. Oncol.* 37:460; Ribas, 2010 *Sem. Oncol.* 37:450). In certain embodiments, the negative regulator of an immune response can be PD-1/CD279, and the inhibitor of the negative regulator of an immune response is an anti-PD-1 antibody. In certain embodiments, immunotherapy can comprise treatment with an agent that targets a potentiator of an immune response. The potentiator of an immune response can be 41BB/CD137 (Kwon et al., 1989 *Proc. Nat. Acad. Sci. USA* 86:1963), OX40/CD134 (GenBank Acc. No. AJ277151) or CD40 (Banchereau et al., 1994 *Ann. Rev. Immunol.* 12:881).

In certain other embodiments, immunotherapy can comprise treatment of an inflammatory condition or an autoimmune disease with an inhibitor of an inflammatory pathway. Contemplated inflammatory conditions or autoimmune diseases include rheumatoid arthritis, psoriatic arthritis, ankylosing spondylitis, Crohn's disease and juvenile idiopathic arthritis. Inflammatory mechanisms have been extensively characterized (e.g., *Goodman & Gilman's The Pharmacological Basis of Therapeutics*, (12$^{th}$ Ed., Brunton et al., Eds., McGraw Hill, NY, 2011, pages 909-1099; 1891-1990; Murphy, *Janeway's Immunobiology* (8$^{th}$ Ed.), 2011 Garland Science, NY), such that in these and related embodiments the inflammatory pathway comprises at least one of tumor necrosis factor-alpha (TNFα), interferon-gamma (IFNγ), interleukin-1 (IL-1), interleukin-6 (IL-6), interleukin-8 (IL-8). For instance, for inflammatory pathways that include TNFα, there are known inhibitors of the inflammatory pathway that specifically bind to TNFα, such as anti-TNFα antibodies (e.g., adalimumab, infliximab) and artificial soluble TNFα receptors (e.g., etanercept).

A. Exemplary Targets for Immunotherapy

The ability to quantify the immunocompetency of a patient's adaptive immune system (as defined as either diversity in the blood or clonality in a tumor tissue, in the case of solid tumors) prior to treatment with an immunomodulatory drug or treatment regimen is predictive of response to treatment and correlative to overall survival.

There are many targets in the immune cascade that can be targeted as potential treatments to cancer and other therapeutic areas. Some are expressed on the surface of T cells and are negative regulators of the immune response, and some are expressed on the surface of antigen presenting cells and are thought to upregulate the immune cascade. Below are exemplary targets in immunotherapy that are or have been used in the clinic (anti-CTLA, ipilimumab) or in active clinical trials, and are currently in use by multiple pharmaceutical manufacturers after reporting successful early data in patients. These targets and inhibitors or regulators thereof can be used in immunotherapy or treatment measures, in accordance with methods of the invention described herein.

Anti-CTLA.

Two proteins on the surface of T cells—CD28 and cytotoxic T-lymphocyte antigen 4 (CTLA-4)—play important roles in the regulation of immune activation and tolerance. CD28 provides positive modulatory signals in the early stages of an immune response, while CTLA-4 signaling inhibits T-cell activation, particularly during strong T-cell responses. CTLA-4 blockade using anti-CTLA-4 monoclonal antibody therapy has great appeal because suppression of inhibitory signals results in the generation of an antitumor T-cell response. Both clinical and preclinical data indicate that CTLA-4 blockade results in direct activation of CD4+ and CD8+ effector cells, and anti-CTLA-4 monoclonal antibody therapy has shown promise in a number of cancers, particularly melanoma. Oncologist. 2008; 13 Suppl 4:2-9. doi: 10.1634/theoncologist.13-S4-2. There are two anti-CTLA4 compounds: (i) Yervoy, or ipilimumab (Bristol Myers Squibb (BMS)) and (ii) tremelimumab (Medimmune).

PD-1.

Programmed death 1 (PD-1) and its ligands, PD-L1 and PD-L2, deliver inhibitory signals that regulate the balance between T cell activation, tolerance, and immunopathology. Immune responses to foreign and self-antigens require specific and balanced responses to clear pathogens and tumors and yet maintain tolerance to self-antigens. Induction and maintenance of T cell tolerance requires PD-1, and its ligand PD-L1 on nonhematopoietic cells can limit effector T cell responses and protect tissues from immune-mediated tissue damage. The PD-1:PD-L pathway also has been usurped by microorganisms and tumors to attenuate antimicrobial or tumor immunity and facilitate chronic infection and tumor survival. The identification of B7-1 as an additional binding partner for PD-L1, together with the discovery of an inhibitory bidirectional interaction between PD-L1 and B7-1, reveals new ways the B7:CD28 family regulates T cell activation and tolerance. Annu Rev Immunol. 2008; 26:677-704. doi: 10.1146/annurev.immunol.26.021607.090331. There are at least 5 known PD-1 compounds in development: Merck (MK-3475), or lambrolizumab; BMS (MBS-936558), or nivolumab; Medimmune (MEDI4736); Glaxo (AMP-224); Genentech (MPDL3280A).

4-1BB.

4-1BB (CD137), a member of the TNF receptor superfamily, is an activation-induced T-cell costimulatory molecule. Signaling via 4-1BB upregulates survival genes, enhances cell division, induces cytokine production, and prevents activation-induced cell death in cells. The importance of the 4-1BB pathway has been underscored in a number of diseases, including cancer. Growing evidence indicates that anti-4-1BB monoclonal antibodies possess strong antitumor properties, which in turn are the result of their powerful CD8+ T-cell activating, IFN-γ producing, and cytolytic marker-inducing capabilities. In addition, combination therapy of anti-4-1BB with other anticancer agents, such as radiation, has robust tumor-regressing abilities against nonimmunogenic or poorly immunogenic tumors. Mol Cancer Ther; 11(5); 1062-70, 2012 AACR. Two examples of 4-1BB compounds are being developed by Pfizer (PF-05082566) and BMS (BMS-663513).

CD40.

CD40 (CD154) is a costimulatory protein found on antigen presenting cells and is required for their activation. The binding of CD154 (CD40L) on Tx cells to CD40 activates antigen presenting cells and induces a variety of downstream effects. The protein receptor encoded by this gene is a member of the TNF-receptor superfamily. This receptor has been found to be essential in mediating a broad variety of immune and inflammatory responses including T cell-dependent immunoglobulin class switching, memory B cell development, and germinal center formation. Entrez Gene: CD40 molecule, TNF receptor superfamily member 5; En.wikipedia.org/wiki/CD40_(protein). Exemplary CD40 compounds include, but are not limited to, the following developed by Seattle Genetics/Genentech (dacetuzumab) and Novartis (lucatumumab).

LAG-3.

LAG-3 (CD223) is a cell surface molecule expressed on activated T cells (Huard et al. Immunogenetics 39:213-217, 1994), NK cells (Triebel et al. J Exp Med 171:1393-1405, 1990), B cells (Kisielow et al. Eur J Immunol 35:2081-2088, 2005), and plasmacytoid dendritic cells (Workman et al. J Immunol 182:1885-1891, 2009) that plays an important but incompletely understood role in the function of these lymphocyte subsets. In addition, the interaction between LAG-3 and its major ligand, Class II MHC, is thought to play a role in modulating dendritic cell function (Andreae et al. J Immunol 168:3874-3880, 2002). Recent preclinical studies have documented a role for LAG-3 in CD8 T cell exhaustion (Blackburn et al. Nat Immunol 10:29-37, 2009), and blockade of the LAG-3/Class II interaction using a LAG-3 Ig fusion protein is being evaluated in a number of clinical trials in cancer patients. Curr Top Microbiol Immunol. 2011; 344:269-78. doi: 10.1007/82_2010_114. LAG-3 is being developed as a target, by companies such as BMS.

Breadth of Targets Along the Immune Cascade.

Immune modulation can also be categorized by compound family (versus specific target) into either a member of the immunoglobulin family or the TNF family. See Nature Reviews Drug Discovery 12, 130-146 (February 2013) (doi:10.1038/nrd3877). This categorization is useful to highlight the breadth of therapeutic categories outside of cancer that these targets can hit, and for which a measure of immunocompetence can be equally as relevant.

TABLE 1

Example List of Targets for Immunotherapy

| Name | Companies | Type of biologic | Pathways | Roles | Indications | Trial phase |
|---|---|---|---|---|---|---|
| Immunoglobulin family | | | | | | |
| Tremelimumab | MedImmune/AstraZeneca | CTLA4-specific human IgG2 | CTLA4-137.1, CTLA4-137.2, B7H2 | T cell priming and activation | Solid tumours | II |
| Galiximab | Cancer and Leukemia Group B (CALGB)/Biogen Idec | B7.1-specific chimeric IgG1 | B7.1 | B cell proliferation | Lymphoma | III |
| BMS-936558 | Bristol-Myers Squibb/Medarex | PD1-specific human IgG4 | PD1-B7H1, PD1-B7DC | T cell activation and tolerance | Multiple cancers; HCV | III |
| CT-011 | CureTech | PD1-specific humanized IgG1 | PD1-B7H1, PD1-B7DC | T cell activation and tolerance | Advanced solid tumours; HCV | II |
| MK-3475 | Merck/Schering-Plough | PD1-specific IgG4 | PD1-B7H1, PD1-B7DC | T cell activation and tolerance | Advanced or metastatic solid tumours | I |
| AMP224 | Amplimmune/GlaxoSmithKline | B7DC and human IgG1 fusion protein | PD1-B7H1, PD1-B7DC | T cell activation and tolerance | Multiple cancers | I |
| BMS-936559 | Bristol-Myers Squibb | B7H1-specific human IgG4 | PD1-B7H1 | T cell activation and tolerance | Advanced or recurrent solid tumours | I |
| MPDL3280A | Genentech/Roche | B7H1-specific engineered human IgG1 | PD1-B7H1 | T cell activation and tolerance | Solid tumours | I |
| MEDI4736 | MedImmune/AstraZeneca | B7H1-specific engineered human IgG1 | PD1-B7H1 | T cell activation and tolerance | Solid tumours | I |
| MEDI-570 | MedImmune/AstraZeneca | ICOS-specific human IgG | ICOS-B7H2 | T cell-dependent B cell response | SLE | I |
| AMG 557 | Amgen | B7H 2-specific human IgG | ICOS, CD28, CTLA4 | T cell-dependent B cell response | SLE, psoriasis | I |

TABLE 1-continued

Example List of Targets for Immunotherapy

| Name | Companies | Type of biologic | Pathways | Roles | Indications | Trial phase |
|---|---|---|---|---|---|---|
| MGA271 | Macrogenics | B7H3-specific, ADCC-enhanced humanized IgG1 | B7H3 | T cell activation and tolerance | Solid tumours | I |
| IMP321 | Immutep | LAG3 and human IgG1 fusion protein | LAG3-MHCII | DC maturation and T cell activation | Multiple cancers | I/II |
| TNF family | | | | | | |
| BMS-663513 | Bristol-Myers Squibb | CD137-specific human IgG4 | CD137 | T cell activation | Solid tumours | I/II |
| PF-05082566 | Pfizer | CD137-specific human IgG | CD137 | T cell activation | Lymphoma | I |
| CDX-1127 | Celldex | CD27-specific human IgG1 | CD27 | T cell activation | Multiple cancers | I |
| Anti-OX40 | Providence Health & Services | OX40-specific mouse IgG | OX40 | CD4 T cell activation | Prostate cancer | II |
| huMAb OX4OL | Genentech/Roche | OX40L-specific human IgG1 | OX40-OX40L | CD4 T cell activation | Asthma | II |
| TRX518 | GITR Inc. | GITR-specific humanized IgG1 | GITR-GITRL | T cell activation | Solid tumours | I |
| Atacicept | ZymoGenetics/EMD Serono | TACI and human IgG1 fusion protein | TACI, BCMA and BAFFR | B cell activation and antibody production | SLE, rheumatoid arthritis, multiple sclerosis and optic neuritis | II/III |
| CP-870,893 | Pfizer | CD40-specific human IgG1 | CD40 | APC activation and B cell maturation | Multiple cancers | I |
| Lucatumumab | Novartis | CD40-specific human IgG1 | CD40 | APC activation and B cell maturation | Lymphoma and leukaemia | I/II |
| Dacetuzumab | Seattle Genetics | CD40-specific humanized IgG1 | CD40 | APC activation and B cell maturation | Lymphoma and multiple myeloma | II |

Nature Reviews Drug Discovery 12, 130-146 (February 2013) (doi:10.1038/nrd3877).

Samples and Subjects.

The subject or biological source, from which a test biological sample can be obtained, can be a human or non-human animal, or a transgenic or cloned or tissue-engineered (including through the use of stem cells) organism. In certain preferred embodiments of the invention, the subject or biological source can be known to have, or can be suspected of having or being at risk for having, cancer or another malignant condition, or an autoimmune disease, or an inflammatory condition, or a bacterial, viral, fungal or other microbial infection, or the subject or biological source can be a solid organ transplant recipient (e.g., recipient of all or a portion of a transplanted liver, lung, kidney, pancreas, intestine, heart, or skin). In some embodiments, or the subject or biological source can be a hematopoietic cell transplant recipient (e.g., recipient of a bone marrow transplant, cord blood transplant, autologous T cell transplant, etc.). In certain embodiments of the invention, the subject or biological source can be known to be free of a risk or presence of such disease. The test biological sample can be obtained from the subject or biological source at one or a plurality of timepoints, for example, at one or a plurality of timepoints prior to administration of treatment or therapy (e.g., immunotherapy) to the subject or biological source, and also at one or a plurality of timepoints during or after administration of treatment or therapy (e.g., immunotherapy) to the subject or biological source.

Certain preferred embodiments contemplate a subject or biological source that is a human subject such as a patient that has been diagnosed as having or being at risk for developing or acquiring cancer according to art-accepted clinical diagnostic criteria, such as those of the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, N.Y.); Pizzo and Poplack, *Principles and Practice of Pediatric Oncology* (Fourth edition, 2001, Lippincott, Williams and Wilkins, Philadelphia/Ovid, N.Y.); Vogelstein and Kinzler, *The Genetic Basis of Human Cancer* (Second edition, 2002, McGraw Hill Professional, New York); Dancey et al. (2009 *Semin. Oncol.* 36 Supp1.3: S46). Certain embodiments contemplate a human subject that is known to be free of a risk for having, developing or acquiring cancer by such criteria. Examples of malignant conditions that are contemplated according to certain present embodiments can include solid tumors such as melanoma, sarcoma, and carcinoma. Others can also include, for example, malignant melanoma, small cell lung cancer, non-small cell lung cancer, renal cell carcinoma, pancreatic cancer, breast cancer, ovarian cancer and prostate cancer.

Certain other embodiments contemplate a non-human subject or biological source, for example a non-human primate such as a macaque, chimpanzee, gorilla, vervet, orangutan, baboon or other non-human primate, including such non-human subjects that can be known to the art as preclinical models, including preclinical models for solid tumors and/or other cancers. Certain other embodiments contemplate a non-human subject that is a mammal, for example, a mouse, rat, rabbit, pig, sheep, horse, bovine, goat, gerbil, hamster, guinea pig or other mammal; many such mammals can be subjects that are known to the art as preclinical models for certain diseases or disorders, including lymphoid hematopoietic malignancies and/or other cancers (e.g., Li et al., 2011 *Dis. Model. Mech.* 4:311; von Euler et al., 2011 *Vet. Comp. Oncol.* 9:1; Goldstein et al., 2010 *Expert Rev. Hematol.* 3:301; Diamond et al., 2009 *J. Bone MM. Res.* 24:1150; Macor et al., 2008 *Curr. Pharm. Des.* 14:2023; Talmadge et al., 2007 *Am. J. Pathol.* 170:793; Kerbel, 2003 *Canc. Biol. Therap.* 2(4 Suppl 1):S134; Man et al., 2007 *Canc. Met. Rev.* 26:737; Cespedes et al., 2006 *Clin. Transl. Oncol.* 8:318). The range of embodiments is not intended to be so limited, however, such that there are also contemplated other embodiments in which the subject or biological source can be a non-mammalian vertebrate, for example, another higher vertebrate, or an avian, amphibian or reptilian species, or another subject or biological source.

As also noted elsewhere herein, art-accepted clinical diagnostic criteria have been established for these and other cancer types, such as those promulgated by the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, N.Y.); Pizzo and Poplack, *Principles and Practice of Pediatric Oncology* (Fourth edition, 2001, Lippincott, Williams and Wilkins, Philadelphia/Ovid, N.Y.); and Vogelstein and Kinzler, *The Genetic Basis of Human Cancer* (Second edition, 2002, McGraw Hill Professional, New York). Other non-limiting examples of typing and characterization of particular cancers are described, e.g., in Ignatiadis et al. (2008 *Pathobiol.* 75:104); Kunz (2008 *Curr. Drug Discov. Technol.* 5:9); and Auman et al. (2008 *Drug Metab. Rev.* 40:303).

Biological samples can be provided by obtaining a blood sample, biopsy specimen, excised tumor specimen such as a solid tumor specimen, tissue explant, organ culture, biological fluid or any other tissue or cell preparation from a subject or a biological source. B cells and T cells can thus be obtained from a biological sample, such as from a variety of tissue and biological fluid samples including bone marrow, thymus, lymph glands, lymph nodes, peripheral tissues and blood, and also from tumor tissues (e.g., tumor-infiltrating lymphocytes), but peripheral blood is most easily accessed. Any peripheral tissue can be sampled for the presence of B and T cells and is therefore contemplated for use in the methods described herein. Tissues and biological fluids from which adaptive immune cells can be obtained include, but are not limited to, skin, epithelial tissues, colon, spleen, a mucosal secretion, oral mucosa, intestinal mucosa, vaginal mucosa or a vaginal secretion, cervical tissue, ganglia, saliva, cerebrospinal fluid (CSF), bone marrow, cord blood, serum, serosal fluid, plasma, lymph, urine, ascites fluid, pleural fluid, pericardial fluid, peritoneal fluid, abdominal fluid, culture medium, conditioned culture medium or lavage fluid. In certain embodiments, adaptive immune cells (e.g., hematopoietic cells of lymphoid lineage such as T cells and B cells) can be isolated from an apheresis sample. Peripheral blood samples can be obtained by phlebotomy from subjects. Peripheral blood mononuclear cells (PBMC) are isolated by techniques known to those of skill in the art, e.g., by Ficoll-Hypaque® density gradient separation. In certain embodiments, whole PBMCs are used for analysis.

In certain related embodiments, preparations that comprise predominantly lymphocytes (e.g., T and B cells) or that comprise predominantly T cells or predominantly B cells, can be prepared for use as a biological sample as provided herein, according to established, art-accepted methodologies. In other related embodiments, specific subpopulations of T or B cells can be isolated prior to analysis using the methods described herein. Various methods and commercially available kits for isolating different subpopulations of T and B cells are known in the art and include, but are not limited to, subset selection immunomagnetic bead separation or flow immunocytometric cell sorting using antibodies specific for one or more of any of a variety of known T and B cell surface markers. Illustrative markers include, but are not limited to, one or a combination of CD2, CD3, CD4, CD8, CD14, CD19, CD20, CD25, CD28, CD45RO, CD45RA, CD54, CD62, CD62L, CDw137 (41BB), CD154, GITR, FoxP3, CD54, and CD28. For example, and as is known to the skilled person, cell surface markers, such as CD2, CD3, CD4, CD8, CD14, CD19, CD20, CD45RA, and CD45RO can be used to determine T, B, and monocyte lineages and subpopulations in flow cytometry. Similarly, forward light-scatter, side-scatter, and/or cell surface markers such as CD25, CD62L, CD54, CD137, CD154 can be used to determine activation state and functional properties of cells.

Illustrative combinations useful in certain of the methods described herein can include $CD8^+CD45RO^+$ (memory cytotoxic T cells), $CD4^+CD45RO^+$ (memory T helper), $CD8^+CD45RO^-$ ($CD8^+CD62L^+CD45RA^+$ (naïve-like cytotoxic T cells); $CD4^-CD25^+CD62L^{hi}GITR^+FoxP3^+$ (regulatory T cells). Illustrative antibodies for use in immunomagnetic cell separations or flow immunocytometric cell sorting include fluorescently labeled anti-human antibodies, e.g., CD4 FITC (clone M-T466, Miltenyi Biotec), CD8 PE (clone RPA-T8, BD Biosciences), CD45RO ECD (clone UCHL-1, Beckman Coulter), and CD45RO APC (clone UCHL-1, BD Biosciences). Staining of total PBMCs can be done with the appropriate combination of antibodies, followed by washing cells before analysis. Lymphocyte subsets can be isolated by fluorescence activated cell sorting (FACS), e.g., by a BD FACSAria™ cell-sorting system (BD Biosciences) and by analyzing results with FlowJo™ software (Treestar Inc.), and also by conceptually similar methods involving specific antibodies immobilized to surfaces or beads.

For nucleic acid extraction, total genomic DNA can be extracted from cells using methods known in the art and/or commercially available kits, e.g., by using the QIAamp® DNA blood Mini Kit (QIAGEN®). The approximate mass of a single haploid genome is 3 pg. Preferably, at least 25,000 to 250,000 cells, for example, at least 50,000 to 125,000 cells, or at least 75,000 to 150,000 cells, or at least 100,000 to 200,000 cells, are used for analysis, i.e., about 0.15 to 1.5 μg, or for instance, 0.6 to 1.2 μg DNA from diploid T or B cells. The number of T or B cells present in a sample can vary considerably when the sample is obtained from a patient having a lymphoid hematological malignancy such as acute T-cell lymphoblastic leukemia (T-ALL). Using peripheral blood mononuclear cells (PBMCs) from a normal healthy adult human as a source, the number of T cells can vary and can be estimated to be about 30% of total cells; the number of B cells can vary and can be estimated to be about 5-15% of total cells in a PBMC preparation.

V. Adaptive Immune Receptors (AIR)

The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MHC class I and class II ligands, which bind to the TCR, are also immunoglobulin superfamily proteins but are specialized for antigen presentation, with a highly polymorphic peptide binding site which enables them to present a diverse array of short peptide fragments at the APC cell surface.

The extracellular portions of native heterodimeric αβ and γδ TCRs consist of two polypeptides each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. CDR3 of αβ TCRs interact with the peptide presented by MHC, and CDRs 1 and 2 of αβ TCRs interact with the peptide and the MHC. The diversity of TCR sequences is generated via somatic rearrangement of linked variable (V), diversity (D), joining (J), and constant genes.

The Ig and TCR gene loci contain many different variable (V), diversity (D), and joining (J) gene segments, which are subjected to rearrangement processes during early lymphoid differentiation. Ig and TCR V, D and J gene segment sequences are known in the art and are available in public databases such as GENBANK.

The V-D-J rearrangements are mediated via a recombinase enzyme complex in which the RAG1 and RAG2 proteins play a key role by recognizing and cutting the DNA at the recombination signal sequences (RSS), which are located downstream of the V gene segments, at both sides of the D gene segments, and upstream of the J gene segments. Inappropriate RSS reduce or even completely prevent rearrangement. The recombination signal sequence (RSS) consists of two conserved sequences (heptamer, 5'-CACAGTG-3', and nonamer, 5'-ACAAAAACC-3'), separated by a spacer of either 12+/-1 bp ("12-signal") or 23+/-1 bp ("23-signal"). A number of nucleotide positions have been identified as important for recombination including the CA dinucleotide at position one and two of the heptamer, and a C at heptamer position three has also been shown to be strongly preferred as well as an A nucleotide at positions 5, 6, 7 of the nonamer. (Ramsden et al. 1994 *Nucl. Ac. Res.* 22:1785; Akamatsu et al. 1994 *J. Immunol.* 153:4520; Hesse et al. 1989 *Genes Dev.* 3:1053). Mutations of other nucleotides have minimal or inconsistent effects. The spacer, although more variable, also has an impact on recombination, and single-nucleotide replacements have been shown to significantly impact recombination efficiency (Fanning et al. 1996 *Cell. Immunol. Immumnopath.* 79:1, Larijani et cl1.1999 *Nucl. Ac. Res.* 27:2304; Nadel et al. 1998 *J. Immunol.* 161:6068; Nadel et al., 1998 *J. Exp. Med.* 187: 1495). Criteria have been described for identifying RSS polynucleotide sequences having significantly different recombination efficiencies (Ramsden et al. 1994 *Nucl. Ac. Res.* 22:1785; Akamatsu et al. 1994 *J. Immunol.* 153:4520; Hesse et. al. 1989 *Genes Dev.* 3:1053, and Lee et al., 2003 *PLoS* 1(1):E1).

The rearrangement process generally starts with a D to J rearrangement followed by a V to D-J rearrangement in the case of Ig heavy chain (IgH), TCR beta (TCRB), and TCR delta (TCRD) genes or concerns direct V to J rearrangements in case of Ig kappa (IgK), Ig lambda (IgL), TCR alpha (TCRA), and TCR gamma (TCRG) genes. The sequences between rearranging gene segments are generally deleted in the form of a circular excision product, also called TCR excision circle (TREC) or B cell receptor excision circle (BREC).

The many different combinations of V, D, and J gene segments represent the so-called combinatorial repertoire, which is estimated to be $\sim 2 \times 10^6$ for Ig molecules, $\sim 3 \times 10^6$ for TCRαβ and $\sim 5 \sim 10^3$ for TCRγδ molecules. At the junction sites of the V, D, and J gene segments, deletion and random insertion of nucleotides occurs during the rearrangement process, resulting in highly diverse junctional regions, which significantly contribute to the total repertoire of Ig and TCR molecules, estimated to be $>10^{12}$.

Mature B-lymphocytes further extend their Ig repertoire upon antigen recognition in follicle centers via somatic hypermutation, a process, leading to affinity maturation of the Ig molecules. The somatic hypermutation process focuses on the V-(D-)J exon of IgH and Ig light chain genes and concerns single nucleotide mutations and sometimes also insertions or deletions of nucleotides. Somatically-mutated Ig genes are also found in mature B-cell malignancies of follicular or post-follicular origin.

VI. Amplification Primers and Multiplex PCR

In certain preferred embodiments described herein, V-segment and J-segment primers can be employed in a PCR reaction to amplify rearranged TCR or Ig CDR3-encoding DNA regions in a test biological sample, wherein each functional TCR or Ig V-encoding gene segment comprises a V gene recombination signal sequence (RSS) and each functional TCR or Ig J-encoding gene segment comprises a J gene RSS. In these and related embodiments, each amplified rearranged DNA molecule can comprise (i) at least about 10, 20, 30 or 40 contiguous nucleotides of a sense strand of the TCR or Ig V-encoding gene segment, with the at least about 10, 20, 30 or 40 contiguous nucleotides being situated 5' to the V gene RSS and/or each amplified rearranged DNA molecule can comprise (ii) at least about 10, 20 or 30 contiguous nucleotides of a sense strand of the TCR or Ig J-encoding gene segment, with the at least about 10, 20 or 30 contiguous nucleotides being situated 3' to the J gene RSS. In certain preferred embodiments, each amplified TCR or Ig CDR3-encoding region is present in an amplified rearranged DNA molecule that is less than 600 nucleotides in length. Without wishing to be bound by theory, these design features for amplifying CDR3-encoding V-J junctional regions permit V-segment primer hybridization to substantially all functional TCR or Ig V-encoding gene segments, and also permit J-segment primer hybridization to substantially all functional TCR or Ig J-encoding segments, and also permit amplification of CDR3-encoding regions that are amenable to sequencing by the herein described high-throughput sequencing (HTS) platforms while including adequate sequence information to identify all possible V-D-J and V-J combinations.

VII. Multiplex Quantitative PCR

As described herein and in view of Robins et al., 2009 *Blood* 114, 4099; Robins et al., 2010 *Sci. Translat. Med.* 2:47ra64; Robins et al., 2011 *J. Immunol. Meth.* doi: 10.1016/j.jim.2011.09. 001; Sherwood et al. 2011 *Sci. Translat. Med.* 3:90ra61; U.S. Application Ser. No. 13/217, 126, U.S. application Ser. No. 12/794,507, WO/2010/151416, WO/2011/106738 (PCT/US2011/026373), WO2012/027503 (PCT/US2011/049012), U.S. A. No. 61/550,311, and U.S. A. No. 61/569,118, according to certain preferred embodiments the present methods involve a multiplex PCR method using a set of forward primers that specifically hybridize to the V segments and a set of reverse primers that specifically hybridize to the J segments where the multiplex PCR reaction allows amplification of all the possible VJ (and VDJ) combinations within a given population of T or B cells.

DNA or RNA can be extracted from cells in a sample, such as a sample of blood or lymph or other sample from a subject known to contain lymphoid cells, using standard methods or commercially available kits known in the art. In some embodiments, genomic DNA is used. In other embodiments, cDNA is transcribed from mRNA obtained from the cells and then used for multiplex PCR.

A multiplex PCR system can be used to amplify rearranged adaptive immune cell receptor loci from genomic DNA, preferably from a CDR3 region. In certain embodiments, the CDR3 region is amplified from a TCRα, TCRβ, TCRγ or TCRδ CDR3 region or similarly from an IgH or IgL (lambda or kappa) locus. Compositions are provided that comprise a plurality of V-segment and J-segment primers that are capable of promoting amplification in a multiplex polymerase chain reaction (PCR) of substantially all productively rearranged adaptive immune receptor CDR3-encoding regions in the sample for a given class of such receptors (e.g., TCRγ, TCRβ, IgH, etc.), to produce a multiplicity of amplified rearranged DNA molecules from a population of T cells (for TCR) or B cells (for Ig) in the sample. Preferably and in certain embodiments, primers are designed so that each amplified rearranged DNA molecule in the multiplicity of amplified rearranged DNA molecules is less than 600 nucleotides in length, thereby excluding amplification products from non-rearranged adaptive immune receptor loci.

In the human genome, there are currently believed to be about 70 TCR Vα and about 61 Jα gene segments, about 52 TCR Vβ, about 2 Dβ and about 13 Jβ gene segments, about 9 TCR Vγ and about 5 Jγ gene segments, and about 46 immunoglobulin heavy chain (IGH) $V_H$, about 23 $D_H$ and about 6 $J_H$ gene segments. Accordingly, where genomic sequences for these loci are known such that specific molecular probes for each of them can be readily produced, it is believed according to non-limiting theory that the present compositions and methods relate to substantially all (e.g., greater than 90%, 91%, 92%, 93%, 94%, 95%, 96%, 97%, 98% or 99%) of these known and readily detectable adaptive immune receptor V-, D- and J-region encoding gene segments.

The TCR and Ig genes can generate millions of distinct proteins via somatic mutation. Because of this diversity-generating mechanism, the hypervariable complementarity determining regions (CDRs) of these genes can encode sequences that can interact with millions of ligands, and these regions are linked to a constant region that can transmit a signal to the cell indicating binding of the protein's cognate ligand. The adaptive immune system employs several strategies to generate a repertoire of T- and B-cell antigen receptors with sufficient diversity to recognize the universe of potential pathogens. In αβ and γδ T cells, which primarily recognize peptide antigens presented by MHC molecules, most of this receptor diversity is contained within the third complementarity-determining region (CDR3) of the T cell receptor (TCR) α and β chains (or γ and δ chains).

The assay technology uses two pools of primers to provide for a highly multiplexed PCR reaction. The first, "forward" pool (e.g., by way of illustration and not limitation, V-segment oligonucleotide primers described herein can in certain preferred embodiments be used as "forward" primers when J-segment oligonucleotide primers are used as "reverse" primers according to commonly used PCR terminology, but the skilled person will appreciate that in certain other embodiments J-segment primers can be regarded as "forward" primers when used with V-segment "reverse" primers) includes an oligonucleotide primer that is specific to (e.g., having a nucleotide sequence complementary to a unique sequence region of) each V-region encoding segment ("V segment) in the respective TCR or Ig gene locus. In certain embodiments, primers targeting a highly conserved region are used, to simultaneously capture many V segments, thereby reducing the number of primers required in the multiplex PCR. Similarly, in certain embodiments, the "reverse" pool primers anneal to a conserved sequence in the joining ("J") segment.

Each primer can be designed so that a respective amplified DNA segment is obtained that includes a sequence portion of sufficient length to identify each J segment unambiguously based on sequence differences amongst known J-region encoding gene segments in the human genome database, and also to include a sequence portion to which a J-segment-specific primer can anneal for resequencing. This design of V- and J-segment-specific primers enables direct observation of a large fraction of the somatic rearrangements present in the adaptive immune receptor gene repertoire within an individual. This feature in turn enables rapid comparison of the TCR and/or Ig repertoires (i) in individuals having a particular disease, disorder, condition or other indication of interest (e.g., cancer, an autoimmune disease, an inflammatory disorder or other condition) with (ii) the TCR and/or Ig repertoires of control subjects who are free of such diseases, disorders conditions or indications.

In some embodiments, as used herein, the term "gene" refers to the segment of DNA involved in producing a polypeptide chain such as all or a portion of a TCR or Ig polypeptide (e.g., a CDR3-containing polypeptide); it includes regions preceding and following the coding region "leader and trailer" as well as intervening sequences (introns) between individual coding segments (exons), and can also include regulatory elements (e.g., promoters, enhancers, repressor binding sites and the like), and can also include recombination signal sequences (RSSs) as described herein.

The nucleic acids of the present embodiments, also referred to herein as polynucleotides, and including oligonucleotides, can be in the form of RNA or in the form of DNA, which DNA includes cDNA, genomic DNA, and synthetic DNA. The DNA can be double-stranded or single-stranded, and if single stranded can be the coding strand or non-coding (anti-sense) strand. A coding sequence which encodes a TCR or an immunoglobulin or a region thereof (e.g., a V region, a D segment, a J region, a C region, etc.) for use according to the present embodiments can be identical to the coding sequence known in the art for any given TCR or immunoglobulin gene regions or polypeptide domains (e.g., V-region domains, CDR3 domains, etc.), or can be a different coding sequence, which, as a result of the redundancy or degeneracy of the genetic code, encodes the same TCR or immunoglobulin region or polypeptide.

In one embodiment, the present disclosure provides a plurality of V segment primers and a plurality of J segment primers, wherein the plurality of V segment primers and the plurality of J segment primers amplify substantially all combinations of the V and J segments of a rearranged immune receptor locus. In some embodiments, the method provides amplification of substantially all of the rearranged AIR sequences in a lymphoid cell, and capable of quantifying the diversity of the TCR or IG repertoire of at least $10^6$, $10^5$, $10^4$, or $10^3$ unique rearranged AIR sequences in a sample. "Substantially all combinations" refers to at least 95%, 96%, 97%, 98%, 99% or more of all the combinations of the V and J segments of a rearranged immune receptor locus. In certain embodiments, the plurality of V segment primers and the plurality of J segment primers amplify all of the combinations of the V and J segments of a rearranged immune receptor locus.

In general, a multiplex PCR system can use at least 8, 9, 10, 11, 12, 13, 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to or is complementary to a sequence corresponding to one or more V region segments. The multiplex PCR system also uses at least 3, 4, 5, 6, or 7, and in certain embodiments, 8, 9, 10, 11, 12 or 13 reverse primers, in which each reverse primer specifically hybridizes to or is complementary to a sequence corresponding to one or more J region segments. Various combinations of V and J segment primers can be used to amplify the full diversity of TCR and IG sequences in a repertoire. For details on the multiplex PCR system, including primer oligonucleotide sequences for amplifying TCR and IG sequences, see, e.g., Robins et al., 2009 Blood 114, 4099; Robins et al., 2010 Sci. Translat. Med. 2:47ra64; Robins et al., 2011 J. Immunol. Meth. doi:10.1016/j.jim.2011.09. 001; Sherwood et al. 2011 Sci. Translat. Med. 3:90ra61; U.S. application Ser. No. 13/217,126, U.S. application Ser. No. 12/794,507, WO/2010/151416, WO/2011/106738 (PCT/US2011/026373), WO2012/027503 (PCT/US2011/049012), U.S. A. No. 61/550,311, and U.S. A. No. 61/569,118, which are each incorporated by reference in its entirety.

Oligonucleotides or polynucleotides that are capable of specifically hybridizing or annealing to a target nucleic acid sequence by nucleotide base complementarity can do so under moderate to high stringency conditions. For purposes of illustration, suitable moderate to high stringency conditions for specific PCR amplification of a target nucleic acid sequence would be between 25 and 80 PCR cycles, with each cycle consisting of a denaturation step (e.g., about 10-30 seconds (s) at greater than about 95° C.), an annealing step (e.g., about 10-30s at about 60-68° C.), and an extension step (e.g., about 10-60s at about 60-72° C.), optionally according to certain embodiments with the annealing and extension steps being combined to provide a two-step PCR. As would be recognized by the skilled person, other PCR reagents can be added or changed in the PCR reaction to increase specificity of primer annealing and amplification, such as altering the magnesium concentration, optionally adding DMSO, and/or the use of blocked primers, modified nucleotides, peptide-nucleic acids, and the like.

In certain embodiments, nucleic acid hybridization techniques can be used to assess hybridization specificity of the primers described herein. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the primers are designed not to cross an intron/exon boundary. The forward primers in certain embodiments anneal to the V segments in a region of relatively strong sequence conservation between V segments so as to maximize the conservation of sequence among these primers. Accordingly, this minimizes the potential for differential annealing properties of each primer, and so that the amplified region between V and J primers contains sufficient TCR or Ig V sequence information to identify the specific V gene segment used. In one embodiment, the J segment primers hybridize with a conserved element of the J segment, and have similar annealing strength. In one particular embodiment, the J segment primers anneal to the same conserved framework region motif.

Oligonucleotides (e.g., primers) can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

A primer is preferably a single-stranded DNA. The appropriate length of a primer depends on the intended use of the primer but typically ranges from 6 to 50 nucleotides, or in certain embodiments, from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

As described herein, primers can incorporate additional features which allow for the detection or immobilization of the primer but do not alter the basic property of the primer, that of acting as a point of initiation of DNA synthesis. For example, primers can contain an additional nucleic acid sequence at the 5' end which does not hybridize to the target nucleic acid, but which facilitates cloning, detection, or sequencing of the amplified product. The region of the primer which is sufficiently complementary to the template to hybridize is referred to herein as the hybridizing region.

As used herein, a primer is "specific" for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences which contain the target primer binding sites.

In particular embodiments, primers for use in the methods described herein comprise or consist of a nucleic acid of at least about 15 nucleotides long that has the same sequence as, or is substantially complementary to, a contiguous nucleic acid sequence of the target V or J segment. Longer primers, e.g., those of about 16, 17, 18, 19, 20, 21, 22, 23, 24, 25, 26, 27, 28, 29, 30, 31, 32, 33, 34, 35, 36, 37, 38, 39, 40, 45, or 50 nucleotides long that have the same sequence as, or sequence complementary to, a contiguous sequence of the target V or J segment, will also be of use in certain embodiments. Various mismatches (1, 2, 3, or more) to the target sequence can be contemplated in the primers, while preserving complementarity to the target V or J segment. All intermediate lengths of the aforementioned primers are contemplated for use herein. As would be recognized by the skilled person, the primers can have additional sequence added (e.g., nucleotides that cannot be the same as or complementary to the target V or J segment), such as restriction enzyme recognition sites, adaptor sequences for sequencing, bar code sequences, and the like (see e.g., primer sequences provided herein and in the sequence listing). Therefore, the length of the primers can be longer, such as 55, 56, 57, 58, 59, 60, 65, 70, 75, or 80 nucleotides in length or more, depending on the specific use or need. For example, in one embodiment, the forward and reverse primers are both modified at the 5' end with the universal forward primer sequence compatible with a DNA sequencing nucleic acid sequence.

Also contemplated for use in certain embodiments are adaptive immune receptor V-segment or J-segment oligonucleotide primer variants that can share a high degree of sequence identity to the oligonucleotide primers. Thus, in these and related embodiments, adaptive immune receptor V-segment or J-segment oligonucleotide primer variants can have substantial identity to the adaptive immune receptor V-segment or J-segment oligonucleotide primer sequences disclosed herein, for example, such oligonucleotide primer variants can comprise at least 70% sequence identity, preferably at least 75%, 80%, 85%, 90%, 91%, 92%, 93%, 94%, 95%, 96%, 97%, 98%, or 99% or higher sequence identity compared to a reference polynucleotide sequence such as the oligonucleotide primer sequences disclosed herein, using the methods described herein (e.g., BLAST analysis using standard parameters). One skilled in this art will recognize that these values can be appropriately adjusted to determine corresponding ability of an oligonucleotide primer variant to anneal to an adaptive immune receptor segment-encoding polynucleotide by taking into account codon degeneracy, reading frame positioning and the like. Typically, oligonucleotide primer variants will contain one or more substitutions, additions, deletions and/or insertions, preferably such that the annealing ability of the variant oligonucleotide is not substantially diminished relative to that of an adaptive immune receptor V-segment or J-segment oligonucleotide primer sequence that is specifically set forth herein. As also noted elsewhere herein, in preferred embodiments adaptive immune receptor V-segment and J-segment oligonucleotide primers are designed to be capable of amplifying a rearranged TCR or IGH sequence that includes the coding region for CDR3.

According to certain embodiments contemplated herein, the primers for use in the multiplex PCR methods of the present disclosure can be functionally blocked to prevent non-specific priming of non-T or B cell sequences. For example, the primers can be blocked with chemical modifications as described in U.S. patent application publication US2010/0167353. According to certain herein disclosed embodiments, the use of such blocked primers in the present multiplex PCR reactions involves primers that can have an inactive configuration wherein DNA replication (i.e., primer extension) is blocked, and an activated configuration wherein DNA replication proceeds. The inactive configuration of the primer is present when the primer is either single-stranded, or when the primer is specifically hybridized to the target DNA sequence of interest but primer extension remains blocked by a chemical moiety that is linked at or near to the 3' end of the primer.

The activated configuration of the primer is present when the primer is hybridized to the target nucleic acid sequence of interest and is subsequently acted upon by RNase H or another cleaving agent to remove the 3' blocking group, thereby allowing an enzyme (e.g., a DNA polymerase) to catalyze primer extension in an amplification reaction. Without wishing to be bound by theory, it is believed that the kinetics of the hybridization of such primers are akin to a second order reaction, and are therefore a function of the T cell or B cell gene sequence concentration in the mixture. Blocked primers minimize non-specific reactions by requiring hybridization to the target followed by cleavage before primer extension can proceed. If a primer hybridizes incorrectly to a sequence that is related to the desired target sequence but which differs by having one or more non-complementary nucleotides that result in base-pairing mismatches, cleavage of the primer is inhibited, especially when there is a mismatch that lies at or near the cleavage site. This strategy to improve the fidelity of amplification reduces the frequency of false priming at such locations, and thereby increases the specificity of the reaction. As would be recognized by the skilled person, reaction conditions, particularly the concentration of RNase H and the time allowed for hybridization and extension in each cycle, can be optimized to maximize the difference in cleavage efficiencies between highly efficient cleavage of the primer when it is correctly hybridized to its true target sequence, and poor cleavage of the primer when there is a mismatch between the primer and the template sequence to which it can be incompletely annealed.

As described in US2010/0167353, which is incorporated by reference in its entirety, a number of blocking groups are known in the art that can be placed at or near the 3' end of the oligonucleotide (e.g., a primer) to prevent extension. A primer or other oligonucleotide can be modified at the 3'-terminal nucleotide to prevent or inhibit initiation of DNA synthesis by, for example, the addition of a 3' deoxyribonucleotide residue (e.g., cordycepin), a 2',3'-dideoxyribonucleotide residue, non-nucleotide linkages or alkane-diol modifications (U.S. Pat. No. 5,554,516). Alkane diol modifications which can be used to inhibit or block primer extension have also been described by Wilk et al., (1990 *Nucleic Acids Res.* 18 (8):2065), and by Arnold et al. (U.S. Pat. No. 6,031,091). Additional examples of suitable blocking groups include 3' hydroxyl substitutions (e.g., 3'-phosphate, 3'-triphosphate or 3'-phosphate diesters with alcohols such as 3-hydroxypropyl), 2',3'-cyclic phosphate, 2' hydroxyl substitutions of a terminal RNA base (e.g., phosphate or sterically bulky groups such as triisopropyl silyl (TIPS) or tert-butyl dimethyl silyl (TBDMS)). 2'-alkyl silyl groups such as TIPS and TBDMS substituted at the 3'-end of an oligonucleotide are described by Laikhter et al., U.S. patent application Ser. No. 11/686,894, which is incorporated herein by reference. Bulky substituents can also be incorporated on the base of the 3'-terminal residue of the oligonucleotide to block primer extension.

In certain embodiments, the oligonucleotide can comprise a cleavage domain that is located upstream (e.g., 5' to) of the blocking group used to inhibit primer extension. As examples, the cleavage domain can be an RNase H cleavage domain, or the cleavage domain can be an RNase H2 cleavage domain comprising a single RNA residue, or the oligonucleotide can comprise replacement of the RNA base with one or more alternative nucleosides. Additional illustrative cleavage domains are described in US 2010/0167353, which is incorporated by reference in its entirety.

Thus, a multiplex PCR system can use 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, or more forward primers, wherein each forward primer is complementary to a single functional TCR or Ig V segment or a small family of functional TCR or Ig V segments, e.g., a TCR VP segment, or (see e.g., the TCR primers as set forth in the Sequence Listing), and, for example, 6, 7, 8, 9, 10, 11, 12, 13, 14, 15, 16, 17, 18, 19, 20 or more reverse primers, each specific to a TCR or Ig J segment, such as TCR Jβ segment (see e.g., Sequence Listing). In another embodiment, a multiplex PCR reaction can use four forward primers each specific to one or more functional TCRγ V segment and four reverse primers each specific for one or more TCRγ J segments. In another embodiment, a multiplex PCR reaction can use 84 forward primers each specific to one or more functional V segments and six reverse primers each specific for one or more J segments. Accordingly, various combinations of V and J primers can be used in a multiplex PCR reaction.

In some embodiments, the V and J segment primers are used to produce a plurality of amplicons from the multiplex PCR reaction. In certain embodiments, the amplicons range in size from 10, 20, 30, 40, 50, 75, 100, 200, 300, 400, 500, 600, 700, 800, 900, 1000, 1100, 1200, 1300, 1400, 1500 to 1600 nucleotides in length. In preferred embodiments, the amplicons have a size between 50-600 nucleotides in length.

According to non-limiting theory, these embodiments exploit current understanding in the art (also described above) that once an adaptive immune cell (e.g., a T or B lymphocyte) has rearranged its adaptive immune receptor-encoding (e.g., TCR or Ig) genes, its progeny cells possess the same adaptive immune receptor-encoding gene rearrangement, thus giving rise to a clonal population that can be uniquely identified by the presence therein of rearranged (e.g., CDR3-encoding) V- and J-gene segments that can be amplified by a specific pairwise combination of V- and J-specific oligonucleotide primers as herein disclosed.

The practice of certain embodiments of the present invention will employ, unless indicated specifically to the contrary, conventional methods in microbiology, molecular biology, biochemistry, molecular genetics, cell biology, virology and immunology techniques that are within the skill of the art, and reference to several of which is made below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, N.Y.); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II. Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

VIII. Computer System

Figure 12:
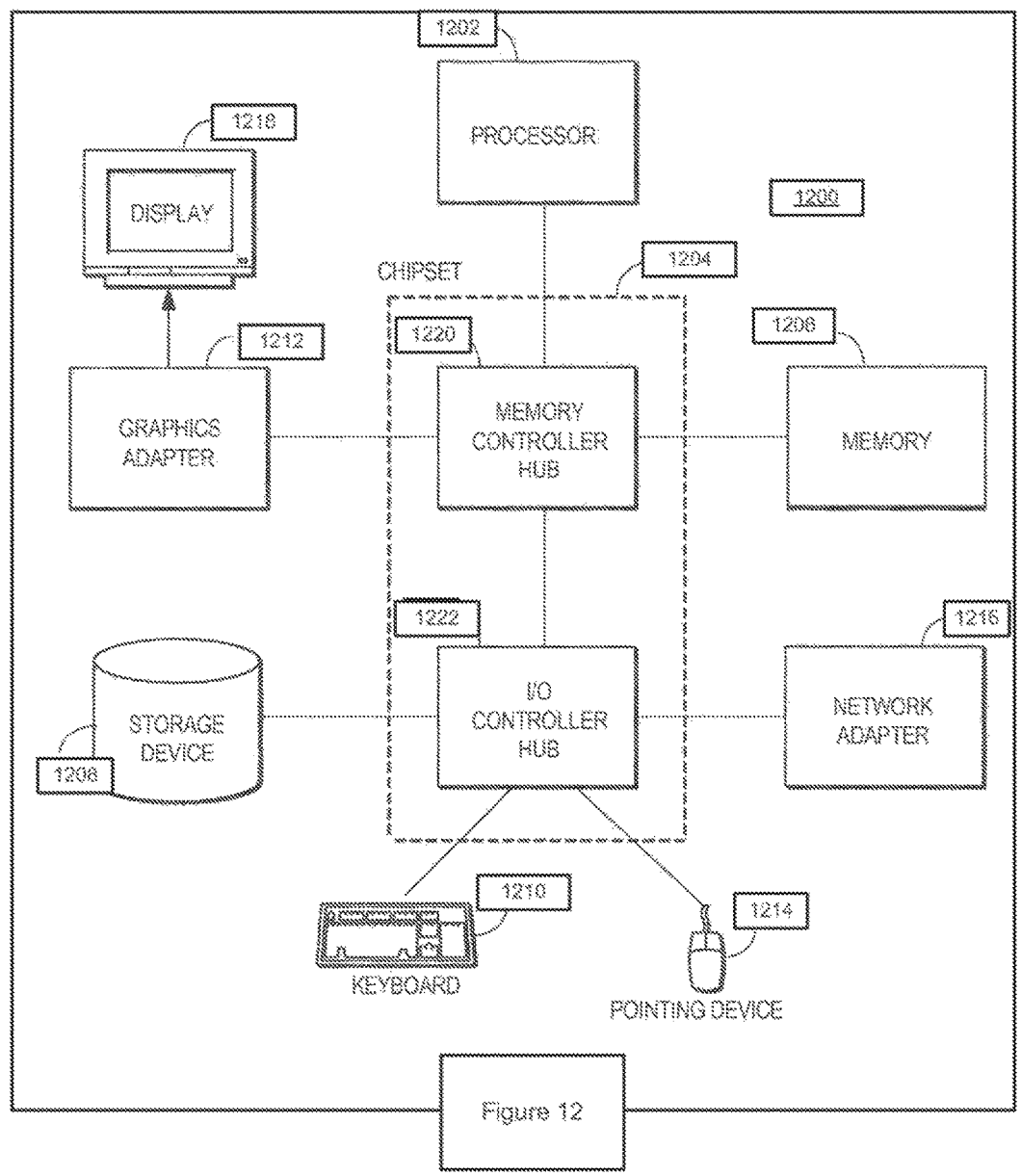
FIG. 12 is a high-level block diagram illustrating an example of a computer, according to one embodiment of the invention.

FIG. 12 is a high-level block diagram illustrating an example of a computer 1200 for use in analyzing molecular analytes, in accordance with one embodiment. Illustrated are at least one processor 1202 coupled to a chipset 1204. The chipset 1204 includes a memory controller hub 1220 and an input/output (I/O) controller hub 1222. A memory 1206 and a graphics adapter 1212 are coupled to the memory controller hub 1220, and a display device 1218 is coupled to the graphics adapter 1212. A storage device 1208, keyboard 1210, pointing device 1214, and network adapter 1216 are coupled to the I/O controller hub 122. Other embodiments of the computer 1200 have different architectures. For example, the memory 1206 is directly coupled to the processor 1202 in some embodiments.

The storage device 1208 is a non-transitory computer-readable storage medium such as a hard drive, compact disk read-only memory (CD-ROM), DVD, or a solid-state memory device. The memory 1206 holds instructions and data used by the processor 1202. The pointing device 1214 is used in combination with the keyboard 1210 to input data into the computer system 1200. The graphics adapter 1212 displays images and other information on the display device 1218. In some embodiments, the display device 1218 includes a touch screen capability for receiving user input and selections. The network adapter 1216 couples the computer system 1200 to the network. Some embodiments of the computer 1020 have different and/or other components than those shown in FIG. 12. For example, the server can be formed of multiple blade servers and lack a display device, keyboard, and other components.

The computer 1200 is adapted to execute computer program modules for providing functionality described herein. As used herein, the term "module" refers to computer program instructions and other logic used to provide the specified functionality. Thus, a module can be implemented in hardware, firmware, and/or software. In one embodiment, program modules formed of executable computer program instructions are stored on the storage device 1208, loaded into the memory 1206, and executed by the processor 1202.

In some embodiments, the computer 1200 is designed to execute a machine learning algorithm for predicting an immune response of a test subject. The system 1200 enables software to carry out actions for a computer-implemented method for determining an immunological status of a test subject.

In some embodiments, the computer-implemented method includes steps for storing data for a control subject obtained from a plurality of samples at various timepoints, said data comprising for each sample, nucleic acid sequence information for a plurality of unique rearranged nucleic acid sequences in said sample, an AIR sequence diversity score for said sample, a frequency of occurrence of each unique rearranged nucleic acid sequence in said sample, and a determined immunological status for said subject.

The computer-implemented method includes steps for determining rules by a processor for assessing an immunological status of a test subject based on said data of said control subject; inputting data for a test subject for a plurality of samples obtained at various timepoints before and after immunotherapy, said data comprising for each sample, nucleic acid sequence information for a plurality of unique rearranged nucleic acid sequences in said sample, an AIR sequence diversity score for said sample, and a frequency of occurrence of each unique rearranged nucleic acid sequence in said sample; and receiving a determination of an immunological status of said test subject.

The computer-implemented method comprises determining a predicted response to immunotherapy of said test subject. In one embodiment, the data for said control subject comprises nucleic acid sequence information obtained from said control subject at a timepoint prior to immunotherapy treatment. In another embodiment, the data for said control subject comprises nucleic acid sequence information obtained from said control subject at a timepoint after immunotherapy treatment.

EXAMPLES

Example 1: T Cell Receptor Diversity after Umbilical Cord Blood Transplant as Predictor of Mortality from Infection This example describes a clinical study in which 34 patients with high risk hematological malignancies were myeloablated and then transplanted with double umbilical cord blood (CB) units. Blood samples were collected at 0, 28, 56, 100, 180, and 360 days post transplant. At each time point, Immunoseg™ high-throughput T cell receptor (TCR) sequencing assay (Adaptive Biotechnologies Corp., Seattle, Wash.) was applied to all samples. The Immunoseg™ data were used to assay the adaptive immune system at unprecedented depth, so that T cell clonal expansion and contraction of hundreds of thousands of T cell clones were tracked over time and TCR repertoire diversity was directly measured. Using the ability to track clones, the adaptive immune system reconstitution was shown to oscillate wildly with an almost entirely new repertoire appearing at least monthly after CB transplant. The largest clones from the prior blood draw dropped to below detectable levels within weeks, contrasting with the control data where the top clones in healthy patients were not only all observed at the following time point, but remained the highest frequency clones. Also described herein is a demonstration that diversity of the T cell repertoire is a measure of immunocompetence, as a clinical application of high-throughput sequencing. Of the 34 patients, six patients died between Day 100 and Day 360 of infectious cause. At both Day 56 and Day 100, the diversity of the T cell repertoire of each of these six patients was far lower than the average of the remaining patients (P-value=0.015). By two months after transplant, TCR diversity accurately predicted risk of death due to infection.

Patients undergoing hematopoietic cell transplantation (HCT) are at increased risk of early post-transplant morbidity and mortality from infectious complications secondary to the prolonged period of pancytopenia and immune dysregulation that results from the conditioning regimen. Cord blood transplant (CBT) recipients appear to be at even greater risk of early transplant related mortality; in fact a recent study demonstrated that non-relapse mortality (NRM) is highest in double CBT (dCBT) recipients when compared to matched and mismatched unrelated donor recipients. Multiple studies have also demonstrated that immune reconstitution following CBT is significantly delayed relative to conventional donor stem cell sources (PB and BM), further contributing to the increased risk of life-threatening infectious complications in this patient population, and consequently CBT recipients have a higher incidence of opportunistic infections (OI) in the first year after transplant [6-8]. Further complicating matters is a dearth of assays that can adequately measure reconstitution of the adaptive immune system, thereby making it difficult to directly address the role of delayed immunity on CBT outcomes in the setting of many other contributing variables (e.g., age, HLA match, intensity of the regimen, concurrent immunosuppressive therapy for prevention and treatment of graft-versus-host disease (GVHD)). This Example demonstrates the ability to more accurately measure functional immune reconstitution in patients undergoing HCT and thus determine the consequent risk of mortality from infectious complications, which will positively impact direct medical decision-making aimed at reducing this risk, especially in the setting of immunosuppressive therapy for the prevention and treatment of GVHD.

In the blood of a healthy adult, an individual T cell primarily expresses one of millions of different TCRs, and a clone is the set of T cells expressing the same TCR[1,2]. Diversity of the TCR repertoire is known to be necessary for adequate protection against foreign pathogens. This is evident in humans with primary or acquired immunodeficiency diseases (e.g., SCIDS, CVID, and HIV), in aging, and following hematopoietic cell transplantation where loss of TCR diversity has been implicated in the increase in morbidity and mortality from infection that is observed in these patients.

Due to the large number of different T cell clones in the human body, estimates of diversity of the TCR repertoire have generally been extrapolated only indirectly, and with low sensitivity. As such, conventional estimates of diversity are insufficient for clinical decision making or in assessment of the health of the cellular adaptive immune system, for instance, as a guide to patient risk for infectious complications related to a level of immunocompetence, or for determining the level of immunocompetence per se. In order to address these shortcomings of prior approaches, herein is described application of a high-throughput method to sequence millions of TCRs from a single sample, allowing direct determination of the diversity of a T cell repertoire for use in directly measuring the health of the cellular adaptive immune system. This information provides a guide to clinical decision making in the setting of acquired or congenital immunosuppression.

As described herein, T cell repertoire diversity provides a direct measurement of immune reconstitution after myeloablative CBT. TCR diversity was measured in CBT recipients at time points 28, 56, and 100 days post transplant, and shown to be predictive of non-relapse mortality (NRM). Additionally, to better understand the dynamics of immune reconstitution, quantitative TCR sequence diversity and distribution data were obtained at each time point and used to track the expansion and contraction of hundreds of thousands of T cell clones simultaneously.

Methods

Study Design.

Patients undergoing a myeloablative single or double CBT were eligible for this retrospective analysis (of data collected prospectively). All patients provided signed consent to participate in the study which was approved by study's Institutional Review Board.

Patients, Treatment Regimens and Post-Transplant Supportive Care.

Patients with hematologic malignancy, aged ≤45 years old, received a myeloablative CBT if they lacked a suitably HLA-matched related or unrelated donor. The patients' underlying disease was categorized as standard or high-risk based upon previously described criteria [17]. Patients received a single or double CB graft as determined by institutional priority criteria. All CB units were HLA-typed at the intermediate resolution level for HLA-A and HLA-B and allele-level (high resolution) for HLA-DRB1, and all CB units were required to be matched to the recipient at ≥4 of the 6 HLA loci. Patients without pre-transplant blood samples stored for TCR analysis or who died before day 28 were excluded.

Myeloablative conditioning consisted of either cyclophosphamide (Cy) (total 120 mg/kg), hyperfractionated total body irradiation (TBI) over 4 days (total of 13.2 Gy), and fludarabine (Flu) (total 75 mg/m$^2$), or Treosulfan (Treo) (total 42 gm/m$^2$), Flu (total 150 mg/m$^2$), and a single fraction of 2 Gy TBI. All patients received GVHD immunoprophylaxis with cyclosporine-A (CSA) and mycophenolate mofetil (MMF) beginning on day −3. All patients received standard prophylactic antimicrobial and antifungal agents during follow-up [18] and remained at the institution for a minimum of 100 days post-transplant. Patients were seen at least once per week for clinical assessment and follow-up. Acute GVHD was graded using standard criteria based on stages of organ involvement and categorized as acute GVHD grades 0IV [16].

ImmunoSeq™ Assay and Evaluation of Immune Reconstitution Post Transplant.

Peripheral blood was collected on days 28, 56, 80-100, 180, and one and two years post transplant, as well as pre-transplant, for retrospective analysis of immune recovery utilizing the ImmunoSeq™ assay for high-throughput sequencing of TCRβ (TCRB) from genomic DNA extracted from peripheral blood mononuclear cells (PBMCs). Sequencing was performed of the CDR3 region of TCRβ genes from approximately 250,000 PBMCs from each time point in surviving patients enrolled in the trial. The TCRβ CDR3 region was defined according to the IMGT collaboration[3], beginning with the second conserved cysteine encoded by the 3' portion of the Vβ gene segment and ending with the conserved phenylalanine encoded by the 5' portion of the Jβ gene segment. The number of nucleotides between these codons determined the length and therefore the frame of the CDR3 region. TCRβ CDR3 regions were amplified and sequenced using previously described protocols (Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; U.S. application Ser. No. 13/217,126, U.S. application Ser. No. 12/794,507, WO/2010/151416, WO/2011/106738 (PCT/US2011/026373), WO2012/027503 (PCT/US2011/049012). Briefly, a multiplexed PCR method was employed to amplify all possible rearranged genomic TCRβ sequences using 52 forward primers, each specific to a TCR Vβ segment, and 13 reverse primers, each specific to a TCR Jβ segment. Sequence reads of length 60 bp were obtained using the Illumina HiSeq™ System (Illumina, Inc., San Diego, Calif.). Raw HiSeq™ sequence data were preprocessed to remove errors in the primary sequence of each read, and to compress the data. A nearest neighbor algorithm was used to collapse the data into unique sequences by merging closely related sequences, to remove both PCR and sequencing errors.

Statistical Considerations.

Due to sample size limitations (34 patients, including six NRM after day 56), the standard Cox proportional hazards model would not be informative. Given the sample size, the study was powered to robustly test the hypothesis that in blood samples from patients undergoing a myeloablative single or double CBT, a lower diversity of the patient's T cell repertoire at Day 56 (or Day 100) was predictive of death from NRM. Because the distribution of TCR repertoire size among patients was not well-characterized, a one-tailed nonparametric Mann-Whitney U test was used to determine whether patients who eventually suffered NRM had lower values of TCR repertoire diversity. All possible confounding factors could not be assessed in a multivariate model, but each possible confounding factor was analyzed separately. A two-tailed Fisher's exact test was used for binary data, and a two-tailed Mann-Whitney U test was used for continuous data.

Results

Study Cohort.

Patients (N=34) and donor characteristics are outlined in Table 2. Patients were transplanted for treatment of high risk hematologic malignancies, primarily acute lymphoblastic or myeloblastic leukemias (N=26), with 12 patients in CR1 and 14 in CR2 or greater. Table 2 summarizes the patient demographics, diagnoses, and clinical course. The treatment regimen for all patients was similar for the first 56 days post transplant. Of the 34 patients, 31 had GVHD, with six grade III-IV; accordingly all patients were prophylactically treated with corticosteroids.

TABLE 2

Cohort Characteristics of 34 patients included in the analysis

| | |
|---|---|
| Patient Age, Median Years (range) | 27 (1-58) |
| Follow-up, Median days (range) | 369 (34-1657) |
| Median Recipient Weight in Kg (range) | 75.3 (22.5-114.4) |
| Disease, No (%) | |
| AML | 16 (47) |
| ALL | 10 (29) |
| MDS/MPD | 6 (18) |
| Other | 2 (6) |
| Minimal Residual Disease (MRD) | 17 (50) |
| Transplant Type, No (%) | |
| FLU/CY/TBI 1320 cGy † | 24 (71) |
| TREO/FLU/TBI 200 cGy †† | 10 (29) |
| GVHD Prophylaxis, No (%) | |
| Cyclosporine/Mycophenolate | 34 (100) |
| Recipient CMV Serostatus, No (%) | |
| Positive | 22 (64) |
| Negative | 12 (36) |
| HLA disparity, No (%) § | |
| 4/6 | 20 (60) |
| 5/6 | 11 (31) |
| 6/6 | 3 (9) |
| Number of CB units infused per patient | |
| 1 | 2 (6) |
| 2 | 32 (94) |
| Acute GVHD | |
| Grade II or less | 25 (73) |
| Grade III-IV | 6 (18) |

In Table 2, ALL=acute lymphoblastic leukemia; AML=acute myeloid leukemia; MDS/MPD=myelodysplastic/myeloproliferative diseases; FLU=fludarabine; CY=cytoxan; TBI=total body irradiation; TREO=treosulfan; GVHD=graft-versus-host-disease; CMV=cytomegalovirus; CB=Cord blood; CR=Complete remission; MRD=Minimal residual disease. †=Fludarabine 75 mg/m$^2$, Cytoxan 120 mg/kg, TBI 1320 cGy. ††=Treosulfan 42 gm/m$^2$, Fludarabine 150 mg/m$^2$, TBI 200 cGy. § =HLA matching reflects the lowest HLA-match of the 2 units.

Sample Collection.

All patients included in this study had blood drawn pre- and post-transplant on days +28, 56, 80-100, 180, and at one year, for those surviving. Aliquots of over one million PBMCs from each blood draw were sent to Adaptive Biotechnologies (Seattle, Wash.) for deep sequencing of the TCR DNA using the ImmunoSeg™ assay. A fixed amount of DNA was input into the Immunoseg™ assay to allow for direct comparison between samples. In addition, the percent and absolute numbers of T, B and NK cells, and immunoglobulin levels were assessed for each sample.

Dynamics of Immune Reconstitution of the Cellular Adaptive Immune System.

Given the enormous number of potential rearrangements for TCR genes, it was implied that each clone had a virtually unique TCR sequence. These sequences were molecular identifiers for each clone, so that clonal expansion and contraction could be tracked over time, in addition to determining the properties of the clonal distribution at each fixed timepoint.

Overlap with Pre-Treatment Repertoire.

Using the TCR sequence as a molecular tag, hundreds of thousands of T cell clones were tracked across time. All of the 34 patients underwent a myeloablative procedure prior to transplant, so it was assumed that a very limited subset of the pre-treatment repertoire would persist after myeloablation. Surprisingly, the proportion of clones remaining after myeloablative treatment varied widely; in three of the 34 patients, 10% or more of the TCR repertoire at day 180 was derived from the pre-treatment (host) immune system.

In most patients, however, few or no pre-existing clones remained after transplant. FIG. 1 shows the proportion of TCR repertoire carried over after transplant across patients and time points. The fraction of pre-transplant clones persisting post-transplant was stable over time, as evidenced by a strong correlation between the proportion of pre-transplant clones observed at each time point post-transplant (e.g., r=0.9 between the proportion of holdovers at day 28 and day 100), and for most patients was roughly 0.001, indicating that on average about one T-cell per thousand was part of a clone observed pre-transplant. Analysis of clones using the Immunoseg™ high throughput TCR sequencing assay yielded different results than microchimerism as measured by previous methods. The process of TCR rearrangement made it unlikely that substantial clonal identity at the DNA level could be observed by chance in the absence of surviving host T cells. Therefore, these results suggested that the Immunoseg™ high quality TCR sequencing method detected microchimerism in some patients who were previously thought not to harbor any host T cells.

Tracking Clones Post Transplant.

In order to assess the stability of the reconstituting adaptive immune system over time, the persistence of TCR clones found at early time-points was investigated in later samples. Using only patients with samples collected and sequenced at 28, 56, 100, 180 and 365 days post-transplant, the top 10 TCR clones were determined by frequency in each patient at the 28, 56, 100 and 180 day time-points and the sequences of each of these clones was classified as either persistent or transient. A top-ten TCR clone that was observed (at any frequency) at a later time-point was considered persistent, and clones that were never again observed in samples from the same patient were considered transient.

Figure 2:
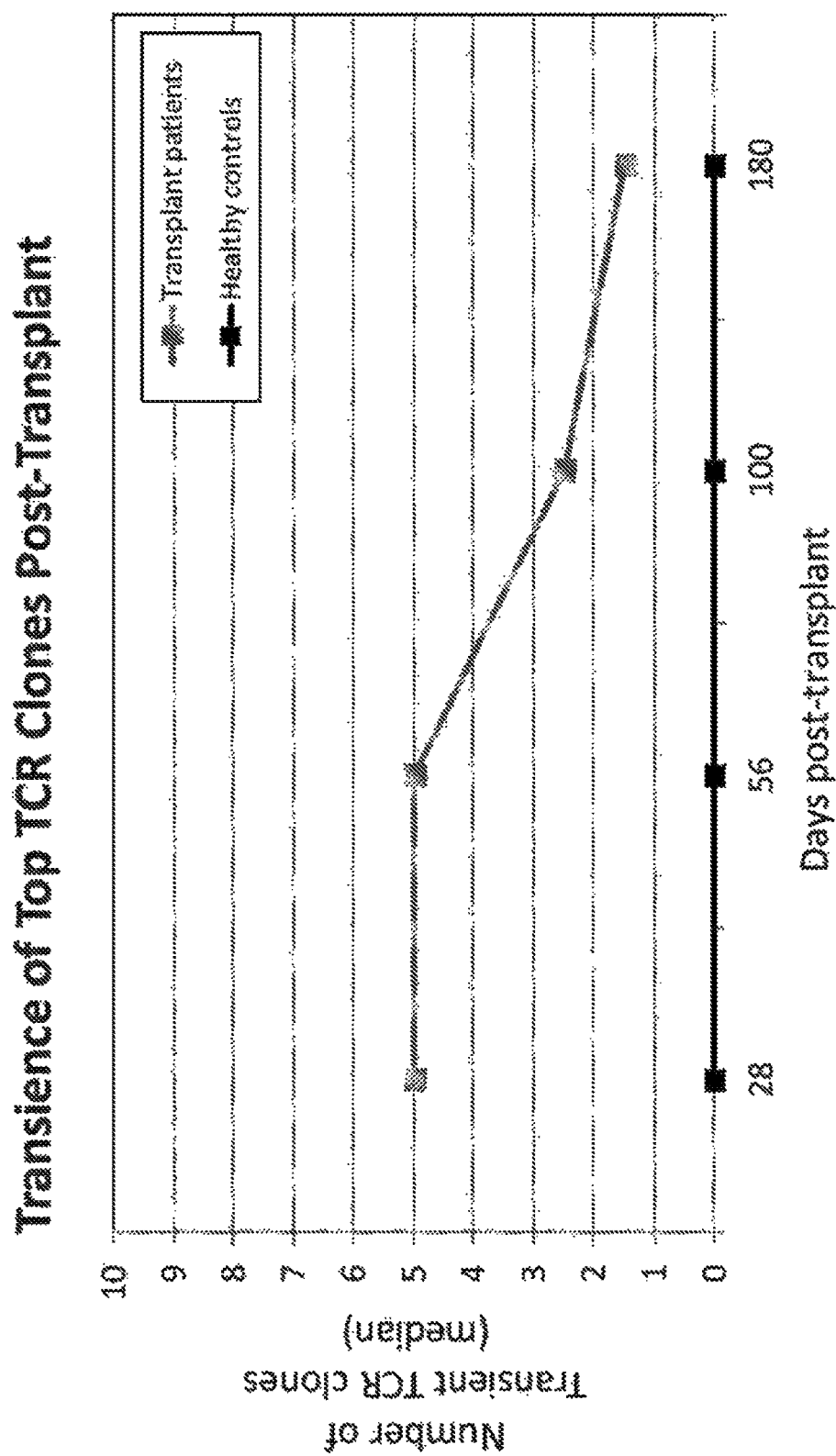
FIG. 2 shows the number of transient TCR clones observed in patients during early immune reconstitution, at 28, 56, 100 and 180 days post-transplant, as compared with healthy controls. For each sample, each of the top 10 TCR clones by frequency was classified as either persistent (observed again in the same patient at a later time point) or transient (not observed again at any level in subsequent samples from the same patient). The number of transient clones was highly variable among patients, ranging from 0 to 9, but the median number of transient clones decreased with time. Four healthy controls were also analyzed, and the number of transient TCR clones ranged from 0 to 2 with a median of 0.

FIG. 2 shows the median number of transient TCR clones in the top 10, at each time-point post-transplant. At 28 and 56 days post-transplant, dynamic and highly unstable TCR repertoires were observed in which many TCR clones that were present at high frequency in an early sample were never again observed subsequently. Starting at 100 days post-transplant, this pattern began to subside and patients' TCR repertoires became more stable. To confirm that this pattern was highly unusual, PBMC samples were sequenced from four healthy control subjects over the same length of time. The median number of transient TCR clones in the top 10 was 0 for these healthy controls at each time-point, confirming the assumption that the high prevalence of transient TCR clones following transplant was indicative of an unusually unstable TCR repertoire. It has been shown previously that a high rate of apoptosis prevailed in T cells following stem cell transplant.[4] Here, it was demonstrated that this apoptotic process was not random with respect to the T cells constituting a clone, but occurred as rapid expansion and contraction of entire clones.

Changes in T Cell Clonal Diversity Post Transplant.

The distribution of T cell clones was used to estimate the lower bound on the diversity in the full blood using an unseen species analysis (Robins et al., 2009 Blood 114, 4099). The diversity estimate was computed for each time point.

Figure 3:
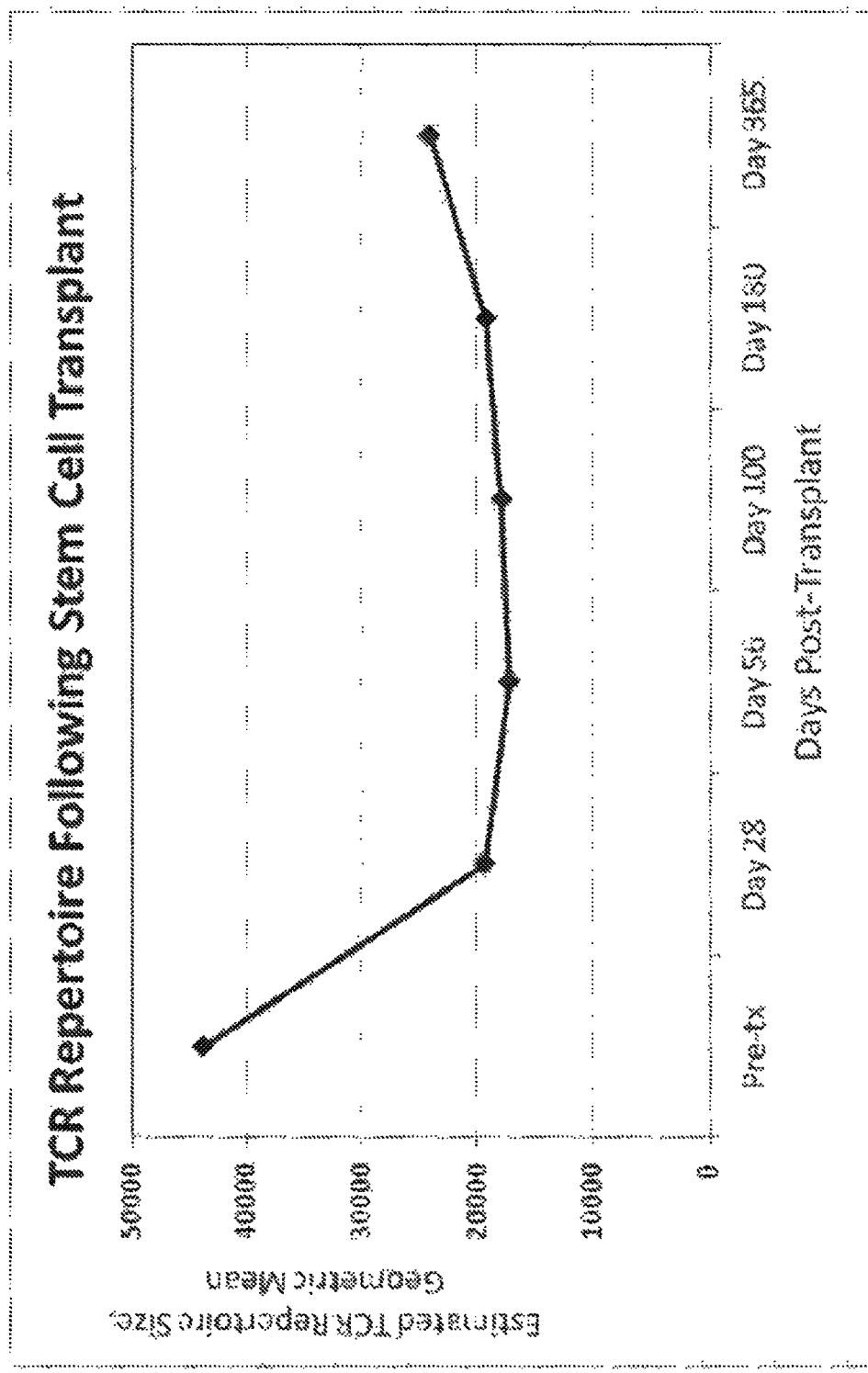
FIG. 3 illustrates TCR repertoire reconstitution after stem cell transplant, shown in TCR repertoire size across all patients following hematopoietic stem cell transplant. Samples were taken before transplant and five times after transplant (at days 28, 56, 100, 180 and 365). TCR repertoire size for each patient was estimated using high-throughput sequencing of TCR rearrangements, and the geometric mean of estimated TCR repertoire size is shown. After transplant, patients had a vastly reduced TCR repertoire that reached its minimum 56 days post-transplant, before beginning a slow recovery.

FIG. 3 presents a summary of immune reconstitution as measured by TCR repertoire during the first year post-transplant in this cohort. The geometric mean of the diversity metric is shown at each time point and is illustrative of the general course of reconstitution. Myeloablative conditioning regimens resulted in a large drop in TCR diversity from pre-transplant values. Diversity decreased from pre-transplant values to day 28, which was close to the mean time to engraftment for most patients (engraftment time ranged from 7 to 45 days with a mean of 24). In this cohort of patients, TCR diversity reached its lowest value at 56 days post-transplant before beginning a slow recovery to a substantial increase in TCR repertoire diversity by one year post-transplant. However, despite this recovery, patient TCR repertoires still had a much lower diversity than healthy repertoires by the end of the one-year study.

Some of the observed changes in TCR diversity can be explained by variations in absolute T cell counts. In the extreme, if a patient had very few T cells, the TCR diversity of such a patient was limited. At day 56, several of the patients had very low CD3 counts and, therefore, low diversity. However, the correlation between diversity and absolute CD3 counts was weak for the remaining cohort (r=0.05, FIG. 5). For example, there were patients in this cohort who had higher absolute CD3 counts but little diversity, secondary to highly oligoclonal TCR repertoire (a small number of highly expanded clones).

TCR Diversity as a Predictor of Mortality from Infection.

Figure 4:
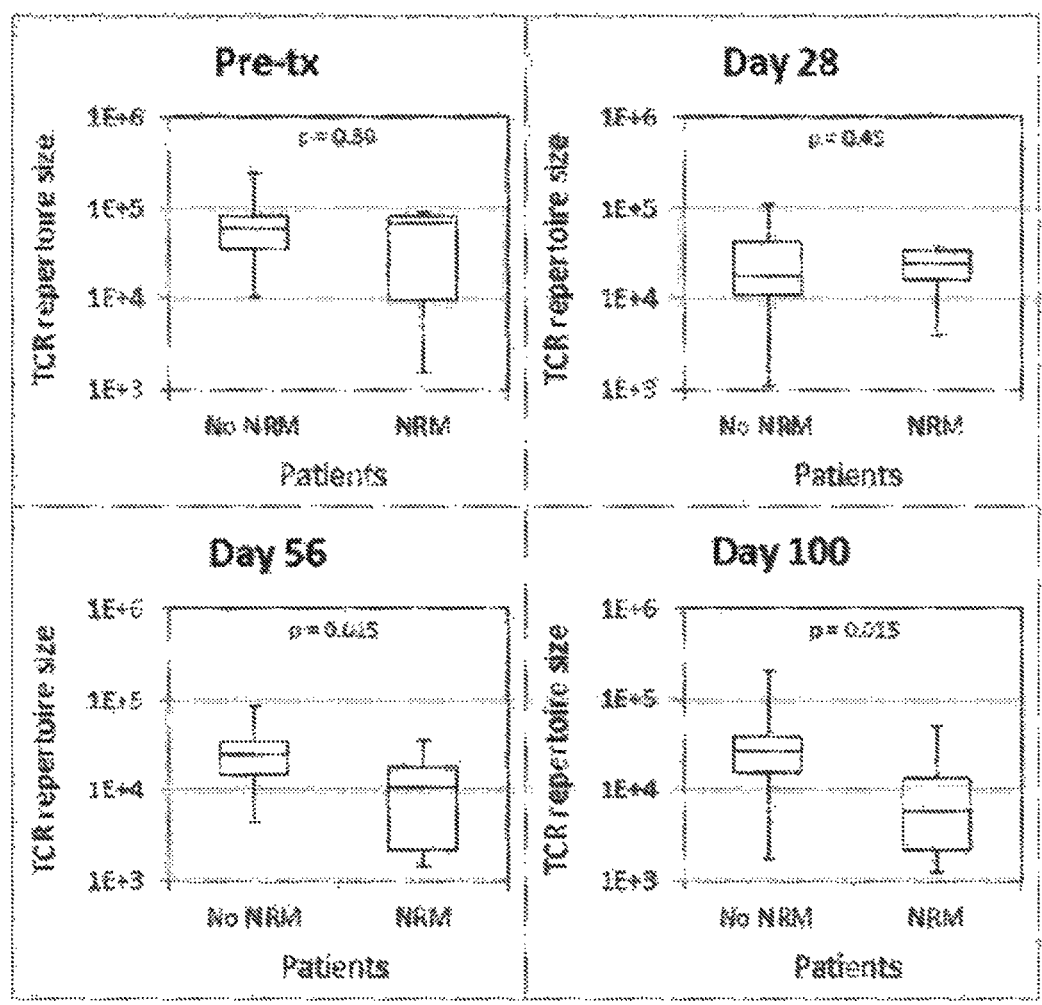
FIG. 4 shows an estimated TCR repertoire size comparison based on high-throughput sequencing of TCRβ rearrangements for all patients with and without eventual non-relapse mortality (NRM). TCR repertoire size values are shown as quartiles for both populations. Significance was assessed using a one-tailed Mann-Whitney U test. Patients who went on to suffer from non-relapse mortality had significantly lower estimated repertoire sizes at 56 and 100 days post-transplant.

Of the 34 patients in the present study, 15 died in the first year post transplant. The sole cause of death in 6 of these patients was relapsed disease, with death primarily from infectious causes in the remaining nine patients. Infectious complications post transplant were not unexpected or uncommon. However, prior to the present disclosure, there was no concrete measurement having strong predictive value to assess which patients were at increased risk of dying from life threatening infections post transplant. Such predictive capability can change the medical management of patients post stem cell transplant. Therefore, the present direct measurement of TCR diversity was analyzed for its potential as an informative predictor of the ability of the adaptive immune system to fight infection. The diversity of the T cell repertoire at early time points post transplant (Day 56 and Day 100) was indeed a strong predictor of mortality from non-relapse causes. The measurement of T cell diversity pre-transplant trended toward predictive value but did not reach statistical significance in this cohort. Day 28 data also lacked significant predictive value, presumably due to the fact that TCR repertoire diversity at this time point was likely dominated by T cells from the graft that were differentiated prior to infusion and thus did not reflect true immune reconstitution. However, patients who eventually died of non-relapse causes beyond day 100 did display significantly reduced TCR diversity as early as 56 days post-transplant (See FIG. 4). Data from those patients who died of NRM (non relapse mortality) consistently yielded a lower estimate of TCR diversity at each time point measured, but this relationship only reached statistical significance (calculated using a one-tailed Mann-Whitney U test, p=0.0153) at day 56, when patients' immune reconstitution had commenced in earnest following engraftment. A significant difference in the TCR diversity of patients who would go on to die from NRM persisted at 100 days post-transplant (p=0.0153). It is worth noting that five of the six patients who were alive at day 56 but eventually died from infectious causes survived through day 180, indicating that clinical identification of high-risk status between 28 and 56 days post transplant would allow ample time for prophylactic clinical intervention.

Other Factors as Predictors of Mortality from Infection.

Post transplant immune recovery is influenced by many factors, most significantly the use of immunosuppressive therapy (IST) for the prevention and treatment of GVHD, in particular the use of steroids. In order to determine the utility of direct measurement of TCR diversity in predicting risk of infection, the roles of possible confounding factors were evaluated, focused on differences in treatment with IST and total absolute CD3 counts. There were 27 patients who developed GVHD at a median of 23 days post transplant. These patients were initially treated with prednisone.

Figure 5:
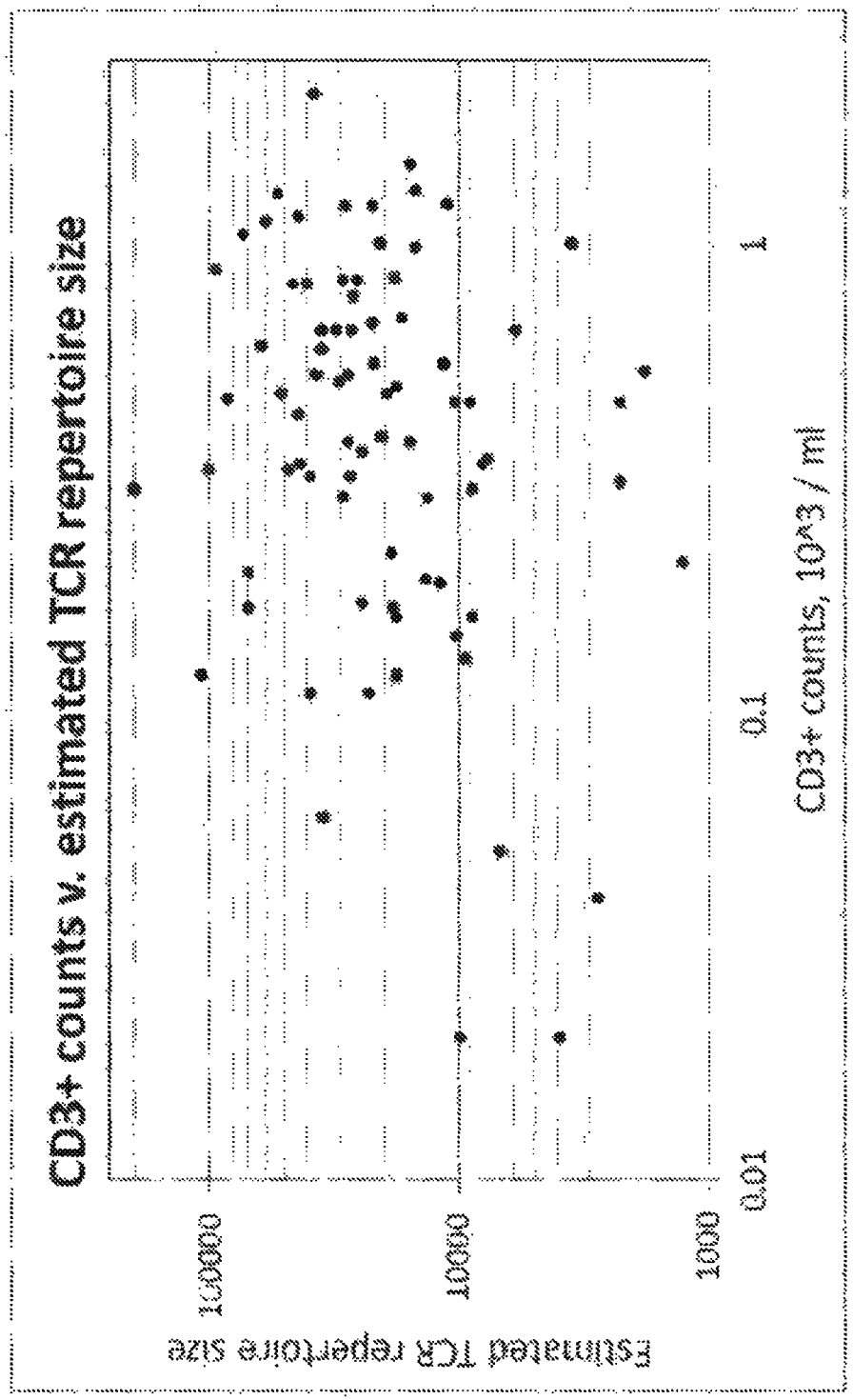
FIG. 5 shows a comparison of CD3+ counts and estimated TCR repertoire size. CD3+ counts (number of cells/mL) were compared to estimated TCR repertoire size for samples from all surviving patients from days 28, 56 and 100 for which both metrics were available. There was a weak correlation between CD3+ counts and repertoire size (r=0.06), indicating that an estimate on the lower bound of TCRβ diversity obtained through sequencing revealed information independent of the total density of circulating T cells.

Another major confounding factor in the correlation of TCR diversity measurements with clinical outcome was the recovery of total CD3+ cells. A correlation of TCR diversity with clinical outcome would be of limited utility if it simply reiterated a result obtained by counting total T cells in peripheral blood. The kinetics of T cell recovery as measured by the absolute CD3+ cells/µl were measured in the peripheral blood at the same time as the measurement of TCR diversity. FIG. 5 shows that absolute CD3+ count was very weakly correlated with estimated TCR repertoire diversity, indicating that these two metrics were essentially independent. This correlation was driven mostly by samples near the lower limit of absolute CD3+ cell counts, since substantially depressed total T-cell counts would necessarily result in determination of a TCR repertoire having low diversity. However, at higher absolute CD3+ counts, it remained possible that an oligoclonal T cell population would nonetheless have had very low TCR diversity and so would have failed to provide protection against opportunistic pathogens.

Table 3 summarizes the results obtained when analyzing CD3+ counts alongside the TCR diversity metric, using data from day 56 and 100 post-transplant. In Table 3, each sample was assigned to a high (at or above median) or low (below median) group for both metrics, and the number of eventual deaths from NRM falling into each category were compared (out of the six that survived until day 56). In addition, Table 3 presents the results of a one-tailed p-value for a Mann-Whitney U test of the hypothesis that patients dying from NRM tended to have lower values of absolute CD3+ counts or TCR diversity. The TCR diversity metric was a predictor of clinical outcome as early as day 56 post transplant while absolute CD3+ counts were uninformative at that time. Furthermore, diversity was more significantly correlated to clinical outcome than CD3+ counts at 100 days post-transplant. The repertoires of the six patients who died from relapse alone were also analyzed. Neither absolute CD3 count nor TCR repertoire diversity predicted death from relapse in this cohort.

TABLE 3

Comparison of CD3+ (total T-cell) counts and estimated TCR repertoire size at days 56 and 100 post-transplant.
Non-relapse mortalities, CD3+ counts v. TCR repertoire size

|  | High | Low | p-value |
|---|---|---|---|
| CD3+ cells/cm$^3$ | | | |
| 56 days post-transplant | 3/15 | 3/14 | 0.139 |
| 100 days post-transplant | 1/15 | 5/14 | 0.021 |
| Estimated TCR repertoire size | | | |
| 56 days post-transplant | 1/15 | 5/14 | 0.015 |
| 100 days post-transplant | 1/15 | 5/14 | 0.015 |

Numbers for each metric represent the number of non-relapse mortalities (n=6) that fall into the high (at or above median) or low (below median) categories. At right is shown the p-value of a one-tailed Mann-Whitney U test. Total T-cell counts were not predictive of clinical outcome at 56 days post-transplant, and were a weaker predictor of clinical outcome than estimated TCR repertoire size at 100 days post-transplant.

In addition to GVHD treatment and total CD3+ counts, the correlation of TCR diversity measurement with clinical outcome could also have been driven by any number of other variables. Table 3 presents a comparison of the 6 patients who lived to day 56 but eventually died of non-relapse causes versus the 25 other patients who were alive at day 56. Several metrics were evaluated between these groups in the same fashion as the TCR diversity metric (Fisher's exact test was used for categorical data, and a Mann-Whitney U test for continuous data). None reached statistical significance in this cohort, with many appearing completely uncorrelated with NRM. The 6 NRM patients were somewhat older than the others (p=0.051), which can indicate a weak correlation to NRM with or without TCR diversity acting as an intermediary. These results indicated that in this cohort, in which TCR repertoire diversity was a statistically significant predictor of non-relapse mortality, non-relapse mortality could not be easily predicted by any of the other variables we examined.

This study used a direct TCR sequence-based measure of immune reconstitution that correlated with adverse clinical outcomes, particularly the increased risk of infectious complications in patients undergoing myeloablative cord blood transplantation. Recipients of CBT were at increased risk of delayed hematopoietic and immune recovery, and improvement in overall survival for these patients was dependent on strategies that can enhance the kinetics of neutrophil and immune system recovery. Direct measures of hematopoietic recovery are simple and well established by obtaining complete blood counts. However, a direct measure of immune system recovery, especially with respect to T cell function as opposed to T cell numbers, has been lacking prior to the present disclosure. Thus, there are standards of care regarding medications for the prevention and treatment of GVHD. However, not all patients are at equal risk of developing complications post transplant and not all patients will respond equally to medical interventions. Novel measurements of immune recovery, as described herein using the ImmunoSeg™ assay, permit tailoring the medical management of individual patients not only with respect to anti-microbial prophylaxis, but also with respect to managing IST if patients are identified as being at higher risk of NRM from infections. A direct measure of this risk would dramatically change medical management.

Here, a significant correlation was demonstrated between measurement of immune reconstitution using high-throughput T cell receptor sequencing and non-relapse mortalities in a cohort of 34 patients. Consistent with this result is the understanding that delayed immune reconstitution, as measured by low diversity of TCR rearrangements in circulating T cells, puts patients at high risk of complications from infectious disease. These results cannot be trivially replicated by CD3+ cell counts or by any of several other variables that were measured in the small cohort. The present results were obtained by analyzing the entire T cell compartment, while it is known that the kinetics and clinical implications of immune reconstitution differ between T cell subsets (e.g., CD4+ v. CD8+ T cells).[5] Hence, investigation of the reconstitution of T cell subsets using HTS can yield additional insights.

The present results demonstrated that high TCR diversity was associated with better outcomes in blood samples taken from patients undergoing myeloablative cord blood transplantation. As such, TCR diversity is a highly useful measure with which to stratify patients soon after transplant based on the risk of future infectious complications. Thus, if a patient has not met a threshold level of TCR diversity by two to three months post-transplant, that patient can benefit by coming off IST more rapidly as tolerated, and/or can be treated more aggressively with anti-microbial prophylaxis, and/or can be kept under observation for a longer period until immune reconstitution has reached adequate levels. Given that decreased TCR diversity preceded non-relapse mortality by several months in the present study, this measure should allow ample time for such prophylactic measures. In addition to identifying high-risk patients, however, the presently described robust measurement of immune reconstitution can also help determine when patients have achieved sufficient immune reconstitution to discontinue prophylactic treatment, rather than administering a regimen of the same duration to each patient.

Example 2: T Cell Receptor Repertoire Distribution as Predictor of Immunotherapy Responders T cell receptor diversity and distribution were determined as described above in blood and solid tumor samples, obtained prior to and after initiation of immunotherapy, from cancer patients who were candidates to receive either a CTLA-4 inhibitor or a PD-1 inhibitor. The efficacy of each immunotherapy agent was independently assessed by standard oncology clinical criteria (categorizing subjects as responders or non-responders) and the relative ability of each patient's adaptive immune system to respond beneficially to the immunotherapy was shown to be predicted by a modified entropy calculation of the distribution of the TCR repertoire prior to immunotherapy.

Before the initiation of immunotherapy (anti-CTLA-4 mAb), responders exhibited relatively higher TCR sequence diversity in lymphocytes present in blood and tumor samples, and higher TCR sequence distribution entropy, observed as a flatter TCR distribution profile, relative to non-responders.

Figure 6:
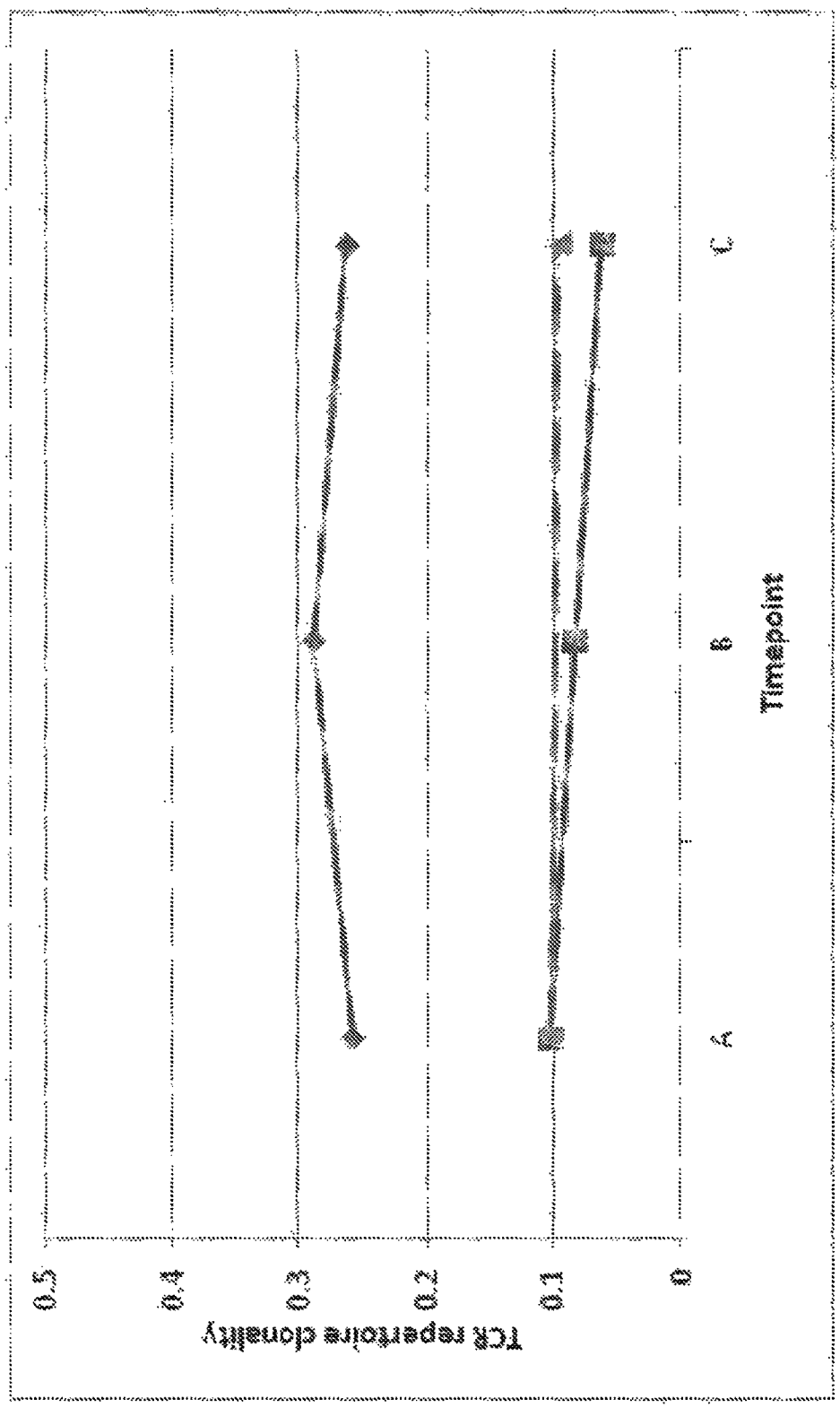
FIG. 6 shows TCR repertoire clonality in blood samples. In blood samples, low TCR repertoire clonality was a predictor of immunotherapy (treatment with ipilimumab (an anti-CTLA-4 mAb)) responder status and high TCR repertoire clonality was a predictor of immunotherapy non-responder status.

As shown in FIG. 6, the results of quantitatively sequencing TCR encoding DNA from blood samples show that low TCR repertoire clonality, indicative of higher TCR sequence diversity and higher TCR sequence distribution entropy, was a predictor of immunotherapy (anti-CTLA-4 mAb) responder status. FIG. 6 also shows that high TCR repertoire clonality, indicative of lower TCR sequence diversity and lower TCR sequence distribution entropy, was a predictor of immunotherapy non-responder status.

Figure 7:
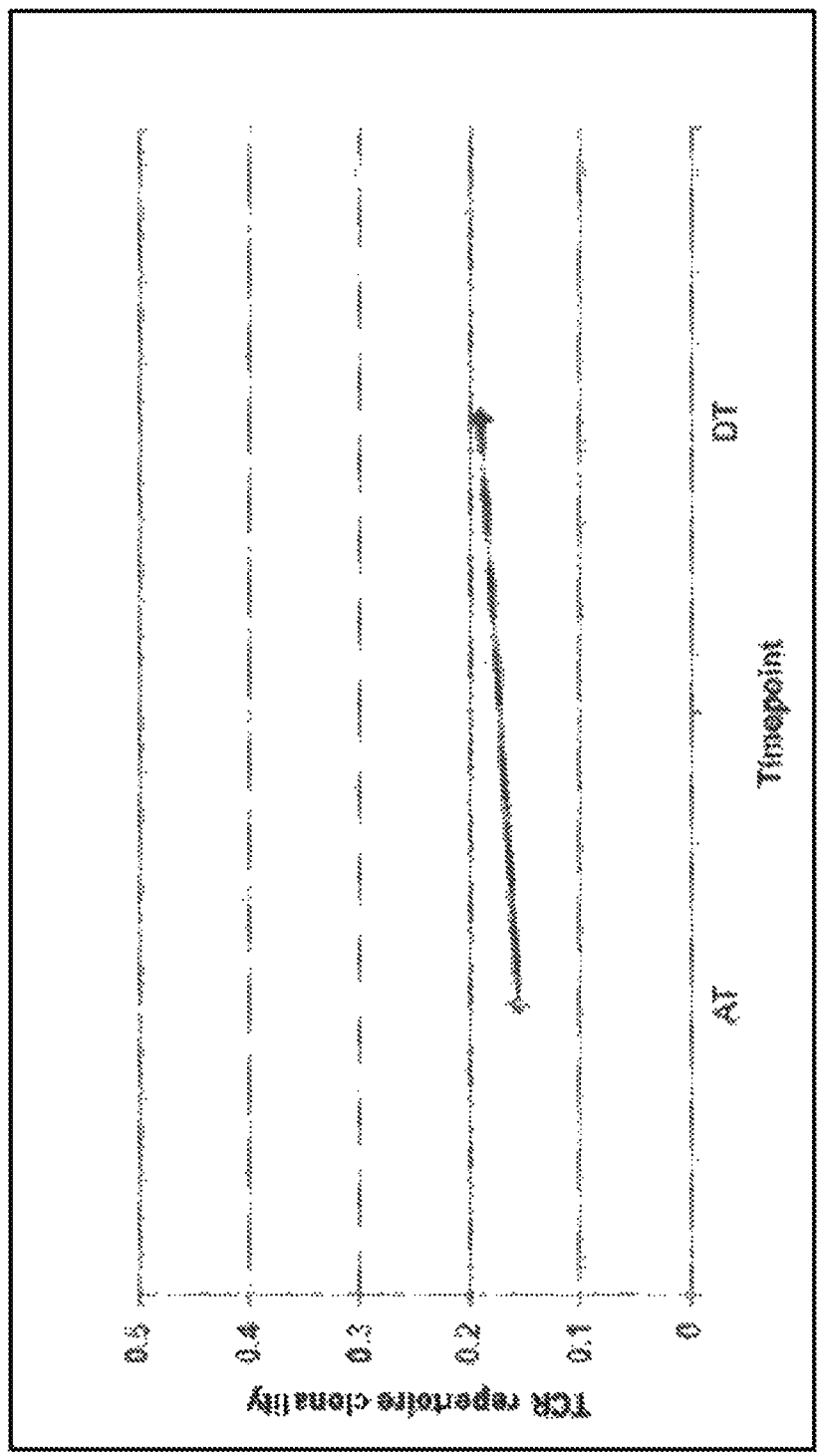
FIG. 7 shows results from quantitative sequencing of TCR encoding DNA from tumor tissue samples. The results show an increase in TCR clonality in lymphocytes present in solid tumor tissue samples obtained after administration of immunotherapy (treatment with ipilimumab (an anti-CTLA-4 mAb)) (DT) relative to the level of TCR clonality detected in tumor samples obtained prior to immunotherapy (AT).

FIG. 7 shows the results from quantitative sequencing of TCR encoding DNA from tumor tissue samples. FIG. 7 illustrates an increase in TCR clonality in lymphocytes present in solid tumor tissue samples obtained after administration of immunotherapy (anti-CTLA-4 mAb) (DT) relative to the level of TCR clonality detected in tumor samples obtained prior to immunotherapy (AT). The sample was obtained from a responder subject. FIG. 7 demonstrates that the immunotherapy treatment had a noticeable impact on the subject's T cell repertoire.

In FIG. 8, the dynamics of individual TCR clonal representations were investigated as a function of time in blood samples and in tumor samples obtained prior to immunotherapy (treatment with ipilimumab (an anti-CTLA-4 mAb)) and post immunotherapy. Timepoints A, B, and C are timepoints taken from blood samples. Timepoint A is before immunotherapy, and timepoints B and C are two timepoints after starting the immunotherapy regimen. Timepoints AT, BT, CT are paired tumor samples (AT is before immunotherapy, and timepoints BT and CT are two timepoints after starting the immunotherapy regimen). Each line of datapoints follows a single clone. The arrow at timepoint CT indicates a single clone that was unremarkable in its relative abundance prior to therapy, but that increased in relative frequency in tumor samples post-therapy, to account for 10% of the repertoire at timepoint CT. Two clones (X1 and X2) that each accounted for 7-9% of TCR sequences in blood at timepoints A and B subsequently declined significantly in relative abundance, while several T cell receptor sequences that initially had very low frequencies in blood increased significantly by timepoint C. The three most numerous clones in tumor samples at timepoint A decreased significantly in their subsequent relative representation, as determined at later timepoints.

In a separate study with the same immunotherapeutic agent used for FIGS. 6-8, TCR sequence diversity and distribution entropies were determined in blood samples obtained prior to (timepoint A) and after (timepoints B and C) initiation of immunotherapy. The results are summarized in FIG. 9, which shows dynamics of individual TCR clonal representations over time. The arrow indicates a single clone that was not highly represented prior to immunotherapy but that increased in preponderance post-therapy to account for greater than 10% of the repertoire at timepoint C.

As shown in FIGS. 8 and 9, a side effect of an immunotherapy treatment can be a proliferation of a single or few clones in the blood of a subject, such that the frequency of occurrence of the single or few clones is statistically significantly greater than the frequencies of occurrence of the other clones in the repertoire. In some embodiments, the frequency of occurrence of a single clone is determined to be greater than a predetermined threshold, such as greater than the top quartile of frequencies of occurrence of the clones in the repertoire. In FIGS. 8 and 9, the single clone that accounts for greater than 10% of the repertoire after immunotherapy treatment is statistically significantly different and is an indicator of poor response by the subject. For example, a clone frequency that is less than 1% in frequency of occurrence before immunotherapy and spikes in frequency to greater than 1% of frequency of occurrence in the repertoire is an indicator of poor outcome in the subject. This presents a situation of a expansion of a single clone (high clonality) and low diversity of the repertoire, leading to poor response and outcome. In situations where a single or few clones exhibit a statistically significantly greater frequency of occurrence compared to the repertoire, adjustments can be made to the treatment of the subject, including use of corticosteroids or immunosuppressants to decrease immune response (e.g., inflammation, etc.).

Example 3: T Cell Receptor Clonality as a Predictor of Immunotherapy Response

In another example, a study was performed using high-throughput sequencing of the TCRB gene locus to characterize the repertoire of tumor-infiltrating lymphocytes (TILs) in late-stage metastatic melanoma patients undergoing immunotherapy (treatment with an anti-PD-1 antibody). The goal of the study was to determine whether characterization of the intratumoral T cell repertoire by high-throughput sequencing is sufficient to predict clinical outcome (i.e., drug response) using immunological profiling (by TCRB sequencing) of a pre-treatment tumor biopsy.

T cell receptor diversity and distribution were determined as described above in solid tumor samples, obtained prior to initiation of immunotherapy, from metastatic melanoma patients who were candidates to receive a PD-1 inhibitor (Lambrolizumab). PD-1 (Programmed cell death protein 1) is a type 1 membrane protein, a member of the immunoglobulin superfamily, and thought to play a role in B cell differentiation.

The efficacy of the immunotherapy treatment was independently assessed by standard oncology clinical criteria. Subjects were characterized as follows: responders (separated into "partial response" indicating a reduction in patient tumor burden and "stable disease" indicating lack of progression without decreased tumor burden) or non-responders (continued disease progression). The relative ability of each patient's adaptive immune system to respond beneficially to the immunotherapy was shown to be predicted by a modified entropy calculation of the distribution of the TCR repertoire prior to immunotherapy.

A modified entropy calculation ("clonality") was used in which each tumor sample's TCR sequence distribution entropy was normalized to the range (0-1) by accounting for the number of unique TCR rearrangements observed in that tumor sample and inverted so that a high normalized entropy becomes a low clonality and vice versa. Before the initiation of immunotherapy, patients who would respond to the immunotherapy exhibited relatively higher TCR sequence distribution clonality in lymphocytes present in tumor biopsy samples, relative to non-responders.

Briefly, frozen tissue samples from malignant lesion biopsies were prepared for 12 patients before administration of an anti-PD-1 antibody (administered as an immunotherapeutic agent for patients with metastatic melanoma). Tissue samples (biopsies from melanoma lesions) were also collected during and after anti-PD-1 immunotherapy. Subsequently, genomic DNA was extracted from these tissue samples. Using the ImmunoSEQ platform for high-throughput TCRB sequencing, the repertoire of TILs in each sample was characterized to determine (1) the extent of intratumoral lymphocyte infiltration, and (2) the clonal structure of the intratumoral lympochyte repertoire.

Of the 12 patients studied, 8 responded to the treatment (stable disease or partial response), while 4 did not respond (disease progression). The results of quantitatively sequencing TCR encoding DNA from frozen tumor tissue biopsies are shown in FIG. 10A.

Figure 10A:
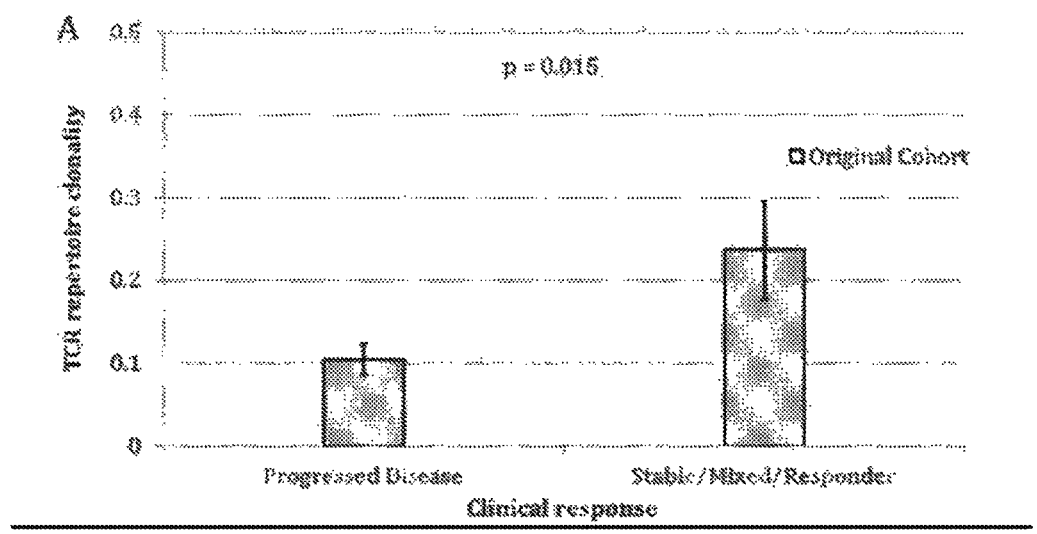
FIG. 10A shows measurements of TCR repertoire clonality from tissue samples from melanoma lesions obtained from late-stage metastatic melanoma patients before, during and after immunotherapy with anti-PD-1 antibody. The mean and standard deviation of TCR repertoire clonality (a modified metric based on TCR sequence distribution entropy normalized to the range (0-1) by accounting for the number of unique TCR sequences present in each sample) is shown according to response to immunotherapy. Of the 12 patients studied, 8 responded to the treatment (stable disease or partial response), while 4 did not respond (disease progression). TCR repertoire clonality was higher in the 8 patients who responded compared to the 4 patients who did not respond (p=0.015 by two-tailed unpaired t-test).

FIG. 10A shows that high intratumoral TCR repertoire clonality, indicative of a TCR repertoire characterized by a small number of highly-expanded T cell clones (low AIR sequence diversity), was a statistically-significant predictor of immunotherapy responder status in this retrospective study of a 12-patient cohort. The mean and standard deviation of TCR repertoire clonality (a modified metric based on TCR sequence distribution entropy normalized to the range (0-1) by accounting for the number of unique TCR sequences present in each sample) are presented according to response to immunotherapy. TCR sequence distribution clonality was significantly higher in the 8 patients who responded compared to the 4 patients who did not respond (p=0.015 by two-tailed unpaired t-test).

Figure 10B:
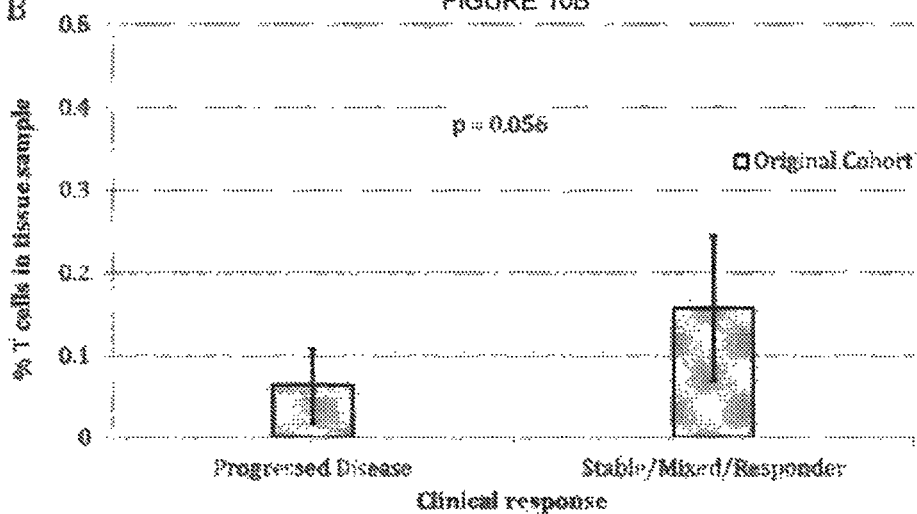
FIG. 10B shows the mean and standard deviation of T cell infiltration (measured as T cell receptor rearrangements per diploid genome) according to response to immunotherapy obtained from tissue samples of melanoma lesions obtained from a cohort of 12 late-stage metastatic melanoma patients. Measured by a two-tailed unpaired t-test, the levels of T lymphocyte infiltration were higher in the 8 patients who responded compared to the 4 patients who did not respond (p=0.056 by two-tailed unpaired t-test). Immunotherapy was treatment with an anti-PD-1 antibody.

In FIG. 10B, T cell infiltration was assessed in the cohort of 12 patients. The mean and standard deviation of T cell infiltration (measured as T cell receptor rearrangements per diploid genome) are presented according to response to immunotherapy. Levels of T lymphocyte infiltration were higher in the 8 patients who responded compared to the 4 patients who did not respond (p=0.056 by two-tailed unpaired t-test).

Data from the first cohort (12 patients with pre- and post-treatment tumor biopsies) suggested that two factors from pre-treatment tumor biopsies (low levels of T cell infiltration and a highly diverse infiltrating T cell repertoire) were associated with failure to respond to treatment (i.e., progressed as opposed to stable or improving disease state; FIGS. 10A, 10B).

Figure 11A:
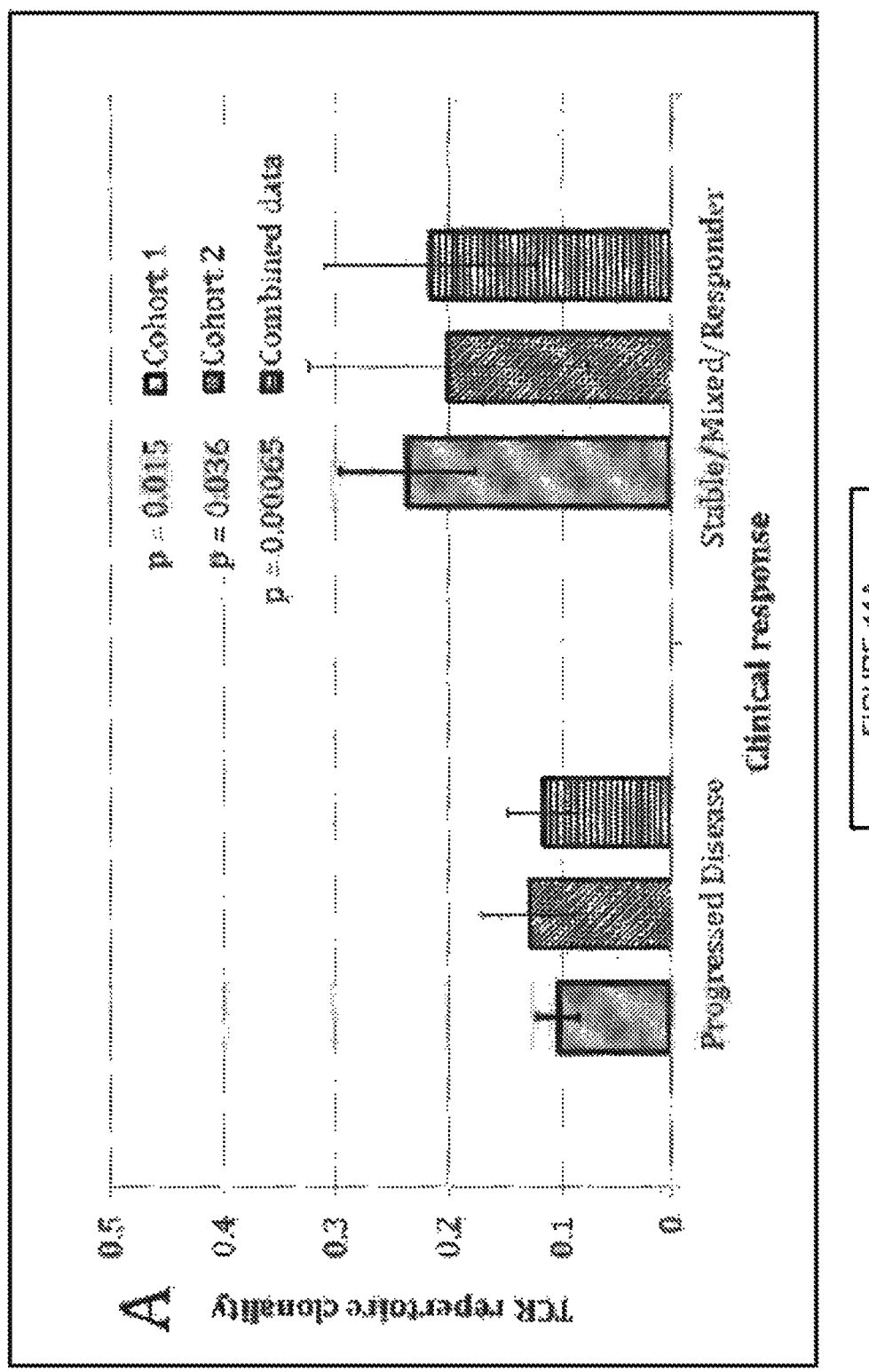
FIG. 11A shows measurements of TCR repertoire clonality and response to immunotherapy for cohort 1 (12 patients), cohort 2 (13 patients), and a combined cohort (obtained from tissue samples of melanoma lesions). Immunotherapy was treatment with an anti-PD-1 antibody. The mean and standard deviation of TCR repertoire clonality (a modified metric based on TCR sequence distribution entropy normalized to the range (0-1) by accounting for the number of unique TCR sequences present in each sample) is shown according to response to immunotherapy in cohort 1 (plain square), cohort 2 (slant striped square) and in the combined data (straight striped square). TCR sequence distribution clonality was higher in the patients who responded compared to the patients who did not respond (p=0.00065 in the combined data by a two-tailed unpaired t-test).

In a second study, a confirmatory cohort of 13 additional patients was assessed, in which only pre-treatment tumor biopsies were sequenced. In FIG. 11A, TCR repertoire clonality and response to immunotherapy were assessed for cohorts 1, 2 and the combined cohort. The mean and standard deviation of TCR repertoire clonality (a modified metric based on TCR sequence distribution entropy normalized to the range (0-1) by accounting for the number of unique TCR sequences present in each sample) is shown according to response to immunotherapy in cohort 1 (plain square), cohort 2 (slant striped square) and in the combined data (straight striped square). TCR sequence distribution clonality was higher in the patients who responded compared to the patients who did not respond (p=0.00065 in the combined data by a two-tailed unpaired t-test).

Figure 11B:
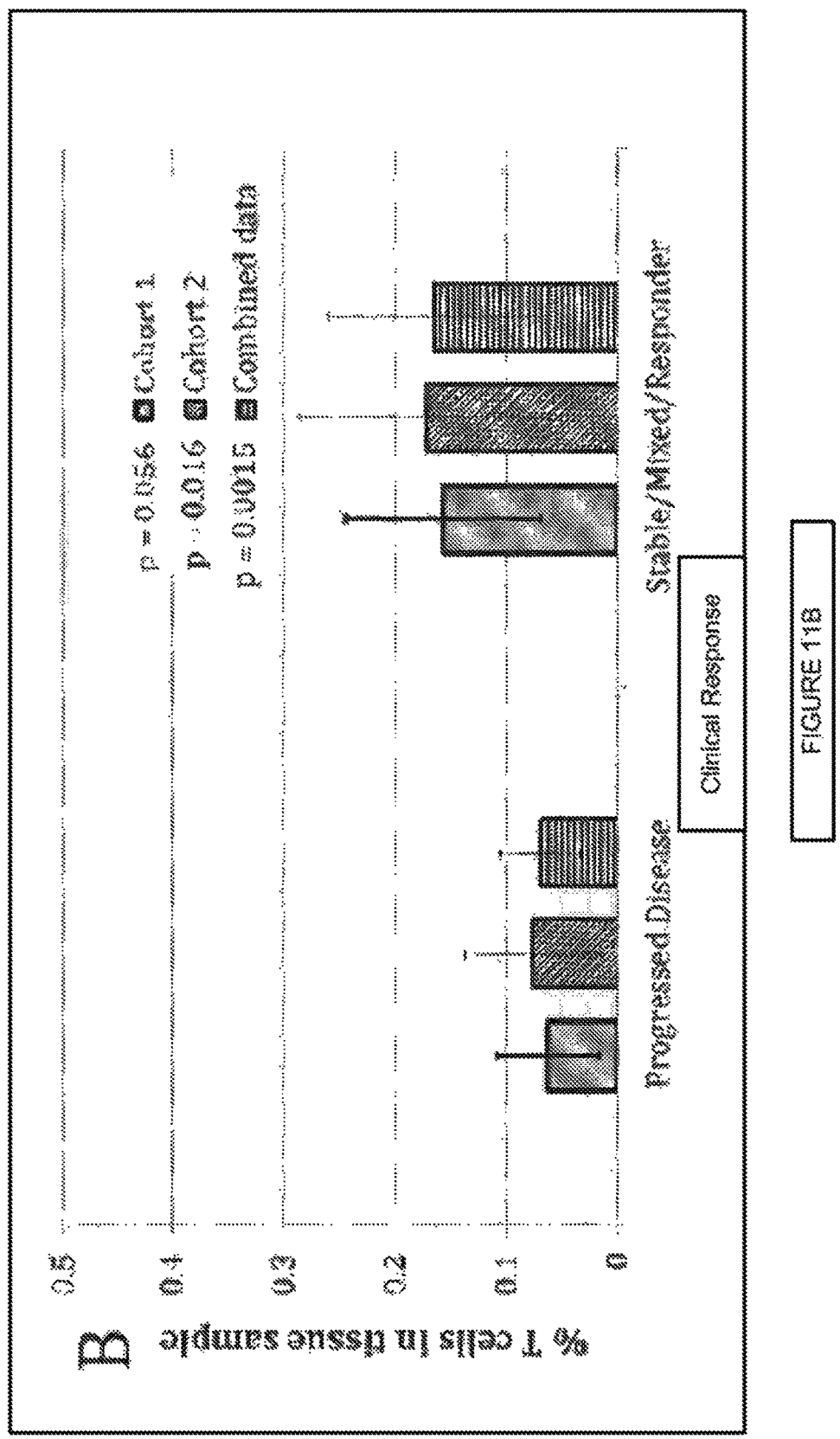
FIG. 11B shows the mean and standard deviation of T cell infiltration (measured as T cell receptor rearrangements per diploid genome) according to response to immunotherapy in cohort 1 (plain square), cohort 2 (slanted stripe square) and in the combined data (straight stripe square). T cells were obtained from tissue samples of melanoma lesions. Immunotherapy was treatment with an anti-PD-1 antibody. Levels of T lymphocyte infiltration are higher in the patients who responded compared to the patients who did not respond (p=0.0015 in the combined data by a two-tailed unpaired t-test).

In FIG. 11B, T cell infiltration was assessed in the patient groups. The mean and standard deviation of T cell infiltration (measured as T cell receptor rearrangements per diploid genome) is shown according to response to immunotherapy in cohort 1 (plain square), cohort 2 (slanted stripe square) and in the combined data (straight stripe square). Levels of T lymphocyte infiltration are higher in the patients who responded compared to the patients who did not respond (p=0.0015 in the combined data by a two-tailed unpaired t-test).

Figure 11C:
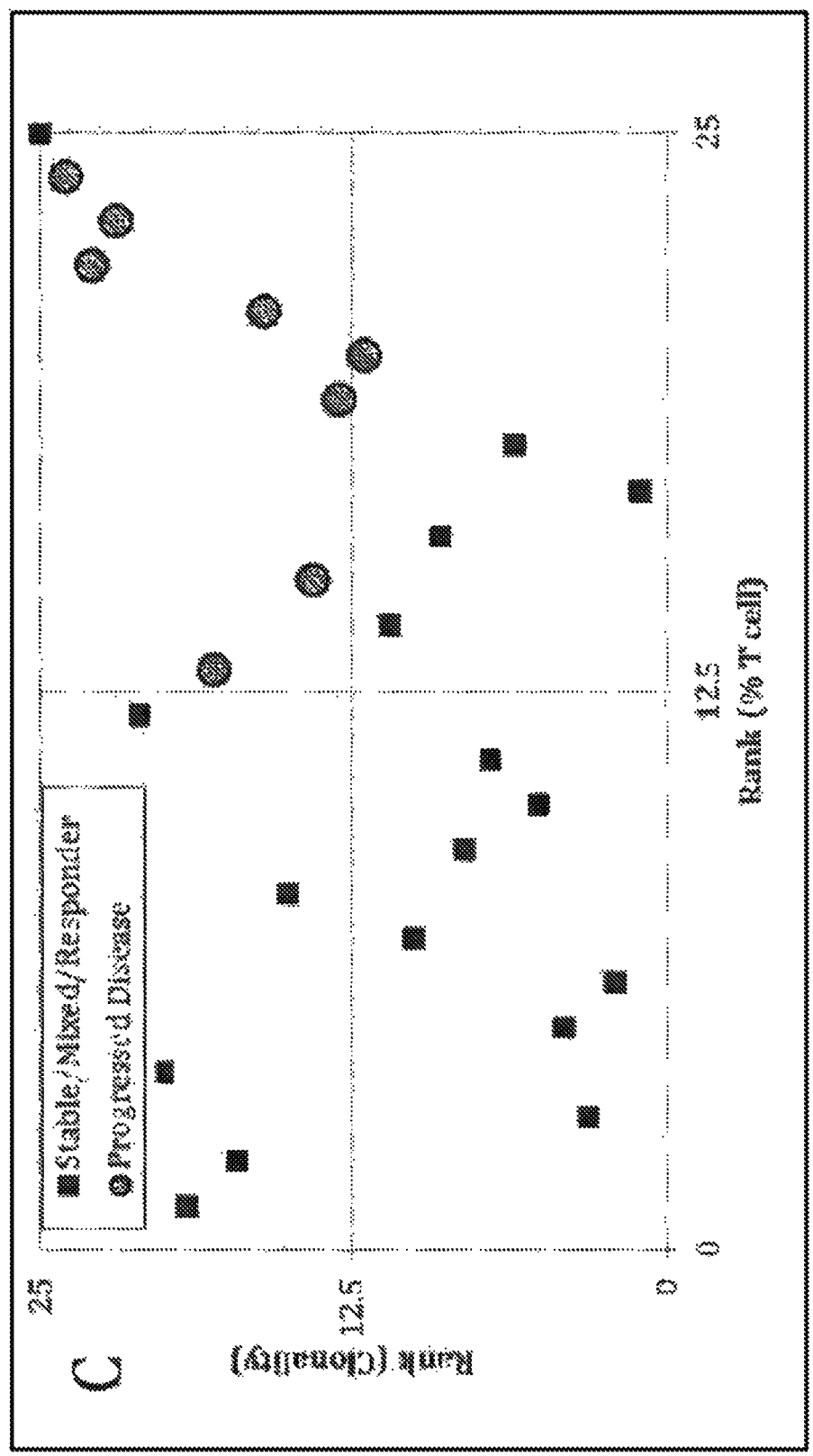
FIG. 11C shows a comparison of each patient's rank (in descending rank, out of 25 patients total) for level of T cell infiltration and TCR repertoire clonality. T cells were obtained from tissue samples of melanoma lesions. Immunotherapy was treatment with an anti-PD-1 antibody. Compared to responders (diamond), non-responders (circle) simultaneously tend toward low TCR repertoire clonality and low levels of infiltrating T lymphocytes.

FIG. 11C shows a comparison of each patient's rank (out of 25 patients total) for level of T cell infiltration and TCR repertoire clonality. Compared to responders (diamond), non-responders (circle) simultaneously tend toward low TCR repertoire clonality and low levels of infiltrating T lymphocytes.

The data from the second cohort of 13 patients were in near-perfect agreement with the initial data from the cohort of 12 patients (FIGS. 11A-C). However, these data together demonstrate that the results of sequencing T cell infiltrates in melanoma tumor biopsies before immunotherapy are highly correlated with patient response to immunotherapy, providing a potential biomarker to predict the effect of immunotherapy on a patient-by-patient basis.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

LIST OF REFERENCES

1. Laughlin M J, Eapen M, Rubinstein P. Outcomes after transplantation of cord blood or bone marrow from unrelated donors in adults with leukemia. *N Engl J Med.* 2004; 351:2265-2275.
2. Wagner J E, Barker J N, Defor T E, et al. Transplantation of unrelated donor umbilical cord blood in 102 patients with malignant and nonmalignant diseases:influence of CD34 cell dose and HLA disparity on treatment related-mortality and survival. *Blood* 2001; 100:1611-1618.
3. Rocha V, Cornish J, Sievers E L, et al. Comparison of outcomes of unrelated bone marrow and umbilical cord blood transplants in children with acute leukemia. *Blood* 2001; 97:2962-2971.
4. Grewal S S, Barker J N, Wagner J E, et al. Unrelated donor hematopoietic cell transplantation: marrow or umbilical cord blood? *Blood* 2003; 101:4233-4244.
5. Rocha V, Labopin M, Sanz G, et al. Transplants of umbilical-cord blood or bone marrow from unrelated donors in adults with acute leukemia. *N Engl J Med.* 2004; 351:2276-2285.
6. Thomson B G, Robertson K A, Gowan D, et al. Analysis of engraftment, graft-versus-host-disease, and immune recovery following unrelated donor cord blood transplantation. *Blood* 2000; 96:2703-2711.
7. Barker J N, Hough R E, van Burik J A, et al. Serious infections after unrelated donor transplantation in 136 children: impact of stem cell source. *Biol Blood Marrow Transplant.* 2005; 11:362-37.
8. Merindol N, Charrier E, Duval M, Soudeyns H. Complementary and contrasting roles of NK cells and T cells in paediatric umbilical cord blood transplantation. *J Leukocyte Biol.* Prepublished on Mar. 2, 2011.
9. Brunstein C G, Barker J N, Weisdorf D J, et al. Umbilical cord blood transplantation after nonmyeloablative conditioning: impact on transplantation outcomes in 110 adults with hematologic disease. *Blood.* 2007; 110(8): 3064-3070.
10. Cornetta K, Laughlin M, Carter S, et al. Umbilical cord blood transplantation in adults: results of the prospective Cord Blood Transplantation (COBLT). *Biology of Blood and Marrow Transplantation.* 2005; 11: 149-160.
11. Long G D, Laughlin M, Madan B, et al. Unrelated umbilical cord blood transplantation in adult patients. *Biology of Blood and Marrow Transplantation.* 2003; 9:772-780.

12. Brown J A, Boussiotis V A. Umbilical cord blood transplantation: basic biology and clinical challenges to immune reconstitution. *Clinical immunology.* 2008; 127: 286-297.
13. Sauter C, Abboud M, Barker J N, ey al. Serious infection risk and immune recovery after double-unit cord blood transplantation. *Biology of Blood and Marrow Transplantation.* 2011; 17: 1460-71.
14. Guérin-El Khourouj V, Dalle J H, Pédron B, et al. Quantitative and Qualitative CD4 T Cell Immune Responses Related to Adenovirus DNAemia in Hematopoietic Stem Cell Transplantation. *Biol Blood Marrow Transplant.* 2011; 17:476-85.
15. Tormo N, Solano C, Benet I, et al. Reconstitution of CMV pp65 and IE-1-specific IFN-γ CD8(+) and CD4(+) T-cell responses affording protection from CMV DNAemia following allogeneic hematopoietic SCT. *Bone Marrow Transplant.* Prepublished on Jan. 1, 2011.
16. Przepiorka D, Smith T L, Folloder J, et al. Risk factors for acute graft-versus-host disease after allogeneic blood stem cell transplantation. *Blood* 1999; 94: 1465-1470.
17. Mielcarek M, Storer B E, Boeckh M, et al. Initial therapy of acute graft-versus-host disease with low-dose prednisone does not compromise patient outcomes. *Blood* 2009; 113:2888-2894.
18. Nakamae H, Kirby K A, Sandmaier B M, et al. Effect of conditioning regimen intensity on CMV infection in allogeneic hematopoietic cell transplantation. *Biol Blood Marrow Transplant.* 2009; 15:694-703.

What is claimed is:

1. A method for treating cancer comprising administering an effective amount of one or more immunotherapy agents to a subject in need thereof that has been identified as having a tumor comprising infiltrating lymphocytes with a high clonality rating,
   wherein the clonality rating is determined by identifying and quantifying the number of unique rearranged adaptive immune receptor (AIR) sequences obtained from a sample comprising the tumor comprising infiltrating lymphocytes from the subject, and
   wherein the clonality rating is characterized as a high clonality rating if the combined frequency of occurrence of the observed rearranged AIR sequences is no more than 10% of the total number of rearranged AIR sequences present in the sample.
2. The method of claim 1, wherein the one or more immunotherapy agents is one or more of an immunotherapeutic antibody, a cytokine, a hematopoietic cell transplant, an immunosuppressive agent, or a vaccine.
3. The method of claim 1, wherein the one or more immunotherapy agents is one or more inhibitors of a negative regulator of an immune response.
4. The method of claim 3, wherein the negative regulator of the immune response is one or more of CTLA4/CD152, LAG3/CD223, and PD-1/CD279.
5. The method of claim 4, wherein the one or more inhibitors of the negative regulator of the immune response is an anti-CTLA-4 antibody or an anti PD-1 antibody.
6. The method of claim 1, wherein the one or more immunotherapy agents target a potentiator of an immune response.
7. The method of claim 6, wherein the potentiator of the immune response is 41BB/CD137.
8. The method of claim 1, wherein the Shannon entropy score is normalized to the range [0-1] by dividing by the logarithm of the number of unique adaptive immune receptors.
9. The method of claim 8, wherein a high clonality rating is indicative of specific clonal expansion.
10. The method of claim 1, wherein the tumor is a melanoma, a carcinoma or a sarcoma.
11. The method of claim 1, wherein the cancer is melanoma, small cell lung cancer, non-small cell lung cancer, renal cell carcinoma, pancreatic cancer, breast cancer, ovarian cancer or prostate cancer.
12. The method of claim 1, wherein the frequency of each unique rearranged adaptive immune receptor obtained from the sample comprising the tumor comprising infiltrating lymphocytes from the subject is determined by amplifying nucleic acid sequences from the sample comprising the tumor comprising infiltrating lymphocytes in a multiplex polymerase chain reaction (PCR) assay, using a plurality of AIR V-segment oligonucleotide primers and either a plurality of J segment oligonucleotide primers or a plurality of AIR C segment oligonucleotide primers to obtained a plurality of amplified rearranged DNA molecules.
13. The method of claim 12, further comprising sequencing the plurality of amplified rearranged DNA molecules.
14. The method of claim 12, wherein the plurality of rearranged DNA molecules is sufficient to quantify the full diversity of the adaptive immune receptors in said sample.
15. The method of claim 1, wherein the clonality rating is characterized as a high clonality rating if the sample comprises a low AIR sequence diversity.
16. The method of claim 1, wherein the unique rearranged AIR sequences identified and quantified are at a number that is needed to account for up to at least 50% of the total number of observed AIR sequences in the sample.

* * * * *